United States Patent [19]

Michelotti et al.

[11] Patent Number: 5,552,409

[45] Date of Patent: Sep. 3, 1996

[54] DIHYDROPYRIDAZINONES, PYRIDAZINONES AND RELATED COMPOUNDS AS FUNGICIDES

[75] Inventors: Enrique L. Michelotti; Anne R. Egan, both of Fort Washington; Ronald Ross, Jr., Jamison; Willie J. Wilson, Chalfont, all of Pa.

[73] Assignee: Rohm and Haas Company, Philadelphia, Pa.

[21] Appl. No.: 221,229

[22] Filed: Mar. 31, 1994

Related U.S. Application Data

[63] Continuation of Ser. No. 749,576, Aug. 28, 1991, abandoned, which is a continuation-in-part of Ser. No. 586,633, Sep. 21, 1990, abandoned.

[51] Int. Cl.[6] ............... C07D 285/13; C07D 231/20; A61K 31/415; A61K 31/425
[52] U.S. Cl. ............... 514/307; 544/8; 544/68; 544/238; 544/239; 544/229; 544/225; 544/234; 544/235; 544/224; 544/241; 544/233; 544/315; 514/314; 514/342; 514/343; 514/340; 514/341; 514/361; 514/404; 514/424; 514/369; 514/376; 546/144; 546/4; 546/167; 546/14; 546/288; 546/290; 546/278.4; 546/268.7; 546/276.1; 546/270.4; 548/544; 548/220; 548/136; 548/144; 548/101; 548/365.7; 548/364.4; 548/110; 540/492
[58] Field of Search ............... 548/544, 229, 548/136, 144, 363; 546/144, 167, 275, 276, 277; 514/376, 369, 424, 404, 361, 340, 341, 363, 307, 314, 342, 343

[56] References Cited

U.S. PATENT DOCUMENTS

| 2,015,429 | 11/1934 | Kracker et al. | 260/87 |
|---|---|---|---|
| 3,770,448 | 11/1973 | Poot et al. | 96/114.1 |
| 3,931,176 | 1/1976 | Houlihan | 260/250 A |
| 3,957,814 | 5/1976 | Möller et al. | 260/310 A |
| 4,081,597 | 3/1978 | Fleming et al. | 548/363 |
| 4,246,403 | 1/1981 | Prossel et al. | 542/432 |
| 4,404,203 | 9/1983 | Sircar | 544/239 |
| 4,670,450 | 6/1987 | Schenttler et al. | 514/341 |
| 4,738,961 | 4/1988 | Jojima et al. | 514/227 |
| 4,806,535 | 2/1989 | Faith et al. | 514/248 |
| 4,906,628 | 3/1990 | Coates | 514/252 |
| 4,943,583 | 7/1990 | Lüthy | 514/364 |
| 4,954,499 | 9/1990 | Prücher | 514/247 |
| 5,064,845 | 11/1991 | Hsu et al. | 514/364 |
| 5,292,762 | 3/1994 | Hsu | 514/363 |

FOREIGN PATENT DOCUMENTS

| 2092719 | 1/1972 | France . |
| 1533010 | 9/1976 | United Kingdom . |

OTHER PUBLICATIONS

Takahiro Haga et al, "Bactericides and Fungicides Containing Pyrazolones," Chemical Abstracts, vol. 114, No. 11, 114:95,150h, Mar. 1991.

Tetsuya Aono et al, "Preparation of Pyrazolones and Peroxylipid Formation Inhibitors and Collagenase Inhibitors Containing Them," vol. 114, No. 7, 114:62092n, Feb. 1991.

Primary Examiner—Mukund J. Shah
Assistant Examiner—Matthew V. Grumbling
Attorney, Agent, or Firm—Joseph F. Leightner

[57] ABSTRACT

This invention relates to substituted dihydropyridazinones, pyridazinones and related compounds, of the formula

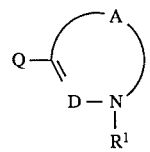

wherein A, Q, D and $R^1$ are as defined within, compositions containing these compounds and methods of controlling agricultural and mammalian fungal diseases.

1 Claim, No Drawings

DIHYDROPYRIDAZINONES, PYRIDAZINONES AND RELATED COMPOUNDS AS FUNGICIDES

STATUS OF RELATED APPLICATIONS

This application is a continuation of U.S. patent application Ser. No. 07/749,576 filed Aug. 28, 1991, abandoned; which is a continuation-in-part of U.S. patent application Ser. No. 07/586,633 filed Sep. 21, 1990, abandoned.

This invention relates to substituted dihydropyridazinones, pyridazinones and related compounds, compositions containing these compounds and a method of controlling fungi by the use of a fungitoxic amount of these compounds.

Although many different types of compounds are known for use as fungicides, and, in particular, for use as agricultural fungicides, there is a continuous demand for new agricultural fungicides. In particular, there is a continuous demand for agricultural fungicides which are active against fungal diseases of rice. Accordingly, this invention relates to the use of a class of pyridazinones and dihydropyridazinones and related compounds in the control of agricultural fungal diseases, particularly in rice.

Further, although different types of compounds are known for use as human fungicides, there remains a need for additional non-toxic, pathogenically selective compounds useful to control fungal diseases in humans. Accordingly, this invention also relates to the use of the compounds of the invention to control fungal diseases in humans.

The compounds used in the present invention are pyridazinone-related compounds of the formula

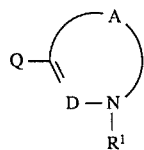

wherein

A is $-(CHR^2)_n-CHR^7-Z-$;
$-CF_2-CF_2-Z-$;
$-(CHR^2)_n-O-Z-$;
$-(CHR^2)_n-S-Z-$;
$-O-CHR^7-Z-$;
$-CR^2=CR^7-Z-$;
$-CR^2=N-Z-$;
$CHR^2-CR^7=Y-$; or
$-CR^2=CR^2-Y=$;

D is $CR^8$ or nitrogen;

Q is an aromatic group selected from

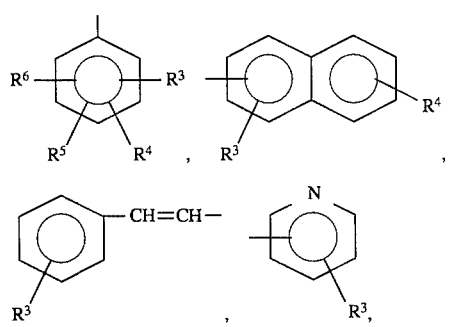

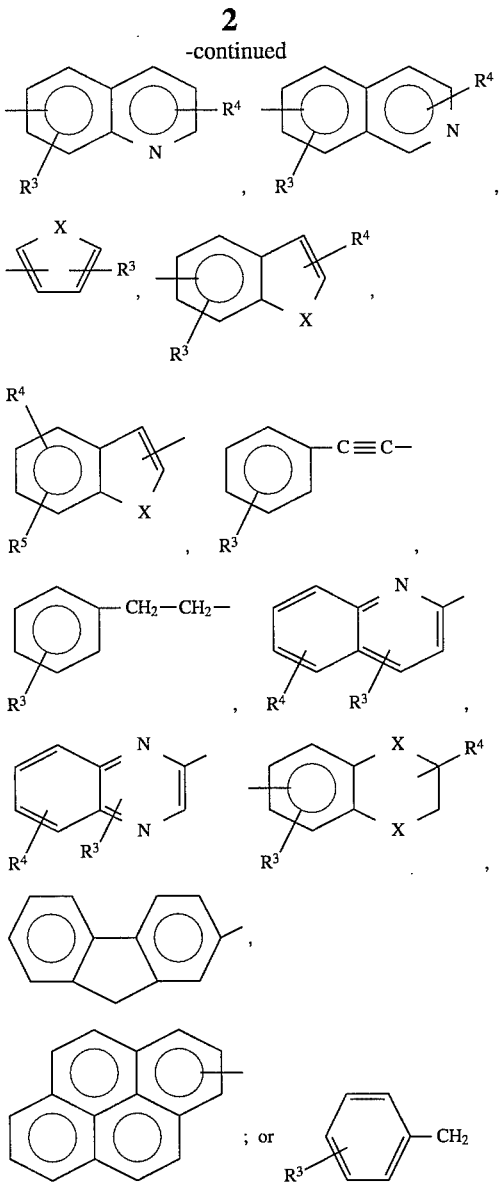

Z is carbonyl (C=O), or thiocarbonyl (C=S);

Y is carbon substituted by halo, alkoxy, alkynylthio or triazolyl;

wherein $R^1$ is alkyl, hydroxyalkyl, cyanoalkyl, hydrazidal and derivatives thereof, cycloalkylalkyl, heterocyclylalkyl, phenyl, phenylalkyl, phenylcarbonyl, alkenyl, haloalkenyl, phenylalkenyl, alkynylalkenyl, alkynyl, haloalkynyl, phenylalkynyl, heterocyclyl, heterocyclylalkynyl, cycloalkylalkynyl, alkenylalkynyl, hydroxyalkynyl, alkoxyalkynyl, alkanoyloxyalkynyl, formylalkynyl, trialkylsilylalkynyl, trialkyltinalkynyl, haloalkenylalkynyl, carboxyalkynyl, or alkoxy-carbonylalkynyl;

$R^2$ and $R^8$ are independently hydrogen, $(C_1-C_3)$alkyl, phenyl, cyano or halogen;

$R^7$ can be hydrogen, $(C_1-C_3)$alkyl, phenyl, cyano or halogen, alkynyl, alkynylalkenyl, dialkynyl, haloalkynyl, and alkenylalkynyl;

$R^3$ and $R^6$ are independently hydrogen, alkoxy or halogen;

$R^4$ is hydrogen, halogen, alkoxy or nitro;

$R^5$ is hydrogen, halogen, nitro, alkyl, alkoxy, alkylthio, haloalkyl, haloalkoxy, haloalkylthio, phenyl, phenoxy or cyano; or $R^2$ and $R^3$ together form a $(C_1-C_3)$alkyl, $(C_2-C_3)$alkylene or carbonyl link; or $R^2$ and $R^7$ together form a fused phenyl or $(C_1-C_3)$ cycloalkyl ring;

X is oxygen (O) or sulfur (S);

n is 0, 1 or 2; and agronomically acceptable salts thereof.

Halo is bromo, fluoro, chloro, and iodo.

Alkyl is, for example, $(C_1-C_6)$ straight or branched alkyl, such as methyl, ethyl, n-butyl or t-butyl. Hydroxyalkyl is, for example, hydroxy$(C_1-C_6)$alkyl such as 1-hydroxypropyl or 3-hydroxybutyl. Cyanoalkyl is, for example, cyano$(C_1-C_6)$alkyl such as cyanomethyl. The hydrazidal moiety is, for example, terminal alkylhydride, such as acetylhydrazide, such that, for example, an embodied compound having this $R^1$ substituent can be 6-halophenyl-2-acetylhydrazide 4,5-dihydropyridazinone. A non-terminal alkyl hydride can have organic groups attached such as, for example, 6-halophenyl-2-[N-acetyhydrazide-(N'-2,4-pentanedione-hydrazone)]-4,5-pyridazinone or, for example, 6-halophenyl-2-[N-acetylhydrazide- (N'-halophenylhydrazone)]-4,5-dihydroazinone. Further embodiments can include cyclicyzed forms such as 6-halophenyl-2-(alkyl-1-pyrazoylmethylene)-4,5-dihydropyridazinone; 6-halophenyl-2-( 1,3,4-oxadiazin-2-one-5-yl-methylene)-4,5-dihydropyridazinone; or 6-halophenyl-2-[2,3,4-oxadiazin-2-one-3-(2'-alkynyl)-5-yl-methylene]-4,5- dihydropyridazinone. Alkynyl substituents to such cyclic compounds can include 2-pentynyl, 2-butynyl and 3-halo-2-propynyl. One example can be 6-(4-chlorophenyl)-2-(1,3,4-oxodiazin-2-one-3-(3'-iodopropargyl)- 5-yl-methylene]-4,5-dihydropyridazinone.

An example of a heterocycyl alkyl is 6-halophenyl-2-(alkyl-4-isoxolylalkyl)-4,5-dihydropyridazinone.

Cycloalkylalkyl is, for example, $(C_3-C_6)$cycloalkyl-$(C_1-C_6)$alkyl such as cyclopropylmethyl. Heterocyclylalkyl is, for example, heterocyclyl$(C_1-C_6)$alkyl such as 2,3-epoxypropyl or alkyl-2-furanylmethylene. Phenylalkyl is, for example, phenyl$(C_1-C_6)$alkyl such as benzyl or 3-chlorobenzyl. Alkenyl is, for example, $(C_3-C_6)$alkenyl such as 2-butenyl, 3-methyl-2-butenyl or allenyl. Haloalkenyl is, for example, halo$(C_3-C_6)$alkenyl such as 3-bromo-2-propenyl, 3,3-dibromo-2-propenyl or 4-bromo-2-butenyl. Phenylalkenyl is, for example, phenyl$(C_3-C_6)$alkenyl such as 3-phenyl-2-propenyl. Alkynylalkenyl is, for example, $(C_3-C_6)$alkynyl$(C_2-C_6)$alkenyl such as 3-(3-methyl-2-propynyl)-2-propenyl or 3-acetylenyl-2-propenyl. Alkynyl is, for example, $(C_3-C_{10})$alkynyl or dialkynyl such as 2-propynyl, 2-butynyl, 1-methyl-2-butynyl, 2-pentynyl, 1-methyl-2-pentynyl, 3-vinyl-2-propynyl, 3-pentynyl, 4-methyl-2-pentynyl, 5,5-dimethyl-2-pentynyl, 2-hexynyl, penta-2,4-diynyl, 2-octynyl or 2-decynyl. Haloalkynyl is for example, halo$(C_3-C_6)$alkynyl such as 3-iodo-2-propynyl, 4-chloro-2-butynyl, 4-bromo-2-butynyl, 4-fluoro-2-butynyl, 4,4-difluoro-2-butynyl, 5-fluoro-2-pentynyl or 4-fluoro-2-pentynyl. Phenylalkynyl is, for example, phenyl$(C_3-C_6)$ alkynyl such as 3-phenyl-2-propynyl or 3-(4-chlorophenyl)-2-propynyl. Heterocyclylalkynyl is, for example, heterocyclyl $(C_3-C_6)$ alkynyl such as 3-(2-thienyl)-2-propynyl. Cycloalkylalkynyl is, for example, 3-cyclohexyl-2-propynyl or 4-cyclohexyl-2-butynyl. Alkenylalkynyl is, for example, $(C_3-C_6)$alkenyl$(C_3-C_6)$alkynyl such as 3-(vinyl)-2-propynyl, 3-(2-methylvinyl)-2-propynyl or 3-(2-propenyl)-2-propynyl. Hydroxyalkynyl is, for example, hydroxy$(C_3-C_6)$alkynyl such as 5-hydroxy-2-pentynyl or 4-hydroxy-2-pentynyl. Alkoxyalkynyl is, for example, $(C_1-C_6)$alkoxy$(C_3-C_6)$alkynyl such as 4-methoxy-2-pentynyl or 4,4-diethoxy-2-butynyl. Alkanoyloxyalkynyl is, for example, $(C_1-C_6)$alkanoyloxy$(C_3-C_6)$alkynyl such as 4-acetyloxy-2-pentynyl. Formyalkynyl is, for example, formyl$(C_3-C_6)$alkynyl such as 3-formyl-2-propynyl. Trialkylsilylalkynyl is, for example tri$(C_1-C_6)$alkylsilyl$(C_3-C_6)$ alkynyl such as 3-trimethylsilyl-2-propynyl. Trialkyltinalkynyl is, for example, tri$(C_1-C_6)$alkyltin$(C_3-C_6)$alkynyl such as 3-(tri-n-butyltin)-2-propynyl. Haloalkenylalkynyl is, for example, halo$(C_3-C_6)$alkenyl$(C_3-C_6)$alkynyl such as 3-(1,2,2-trifluorovinyl)-2-propynyl. Carboxyalkynyl is, for example, carboxy$(C_3-C_6)$alkynyl such as 3-carboxy-2-propynyl. Alkoxycarbonylalkynyl is, for example, $(C_1-C_6)$alkoxycarbonyl-$(C_3-C_6)$alkynyl such as 3-(methoxycarbonyl)-2-propynyl and the like.

$R^2$ and $R^3$ can be linked together to form a $(C_1-C_3)$alkyl, $(C_2-C_3)$alkylene or carbonyl link which can be, for example, a relatively simple linear chain link, such as in 4,4a,5,6-tetrahydro-8-halo[h]-cinnolin-2-$R^1$-3-one or the 5,6-dihydro form thereof. $R^2$ and $R^3$ can be linked together in a $(C_1-C_3)$alkyl, $(C_2-C_3)$alkylene or carbonyl link other than a simple linear chain, such as the fused ring structure exemplified by 8-R'-acenaphtho-[1,2c]pyridazin-9-one.

$R^2$ and $R^7$ can be linked together to form a fused phenyl ring.

The term "heterocyclyl" includes five- and six-membered aromatic, partially saturated or saturated rings or bicyclic ring systems containing up to 10 atoms containing one hetero atom selected from the group of oxygen, sulfur, or nitrogen. Examples include thienyl, epoxy, benzothienyl, pyridyl, quinolyl and the like.

Further, in accordance with the present invention, there are provided compositions containing the above described compounds of the instant invention. In addition, many of the compounds useful in this invention are novel. The compounds which are new include compounds wherein $R^1$ is alkynyl or substituted alkynyl.

In an embodiment of the invention the compounds which are useful have the structure

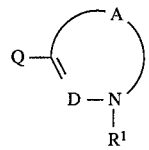

I wherein

A is —$(CHR^2)_n$—$CHR^7$—Z—;

—$CR^2$=$CR^7$—Z—;

—$CR^2$=N—Z—;

—$CHR^2$—$CR^7$=Y—; or

—$CR^2$=$CR^2$—Y=;

D is $CR^8$ or nitrogen;

Q is an aromatic group selected from

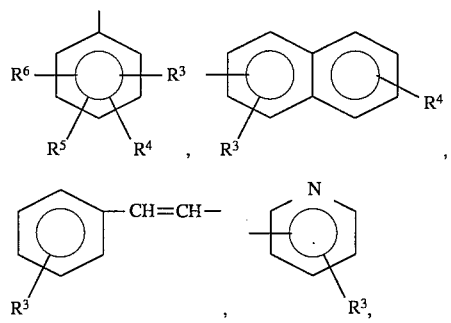

-continued

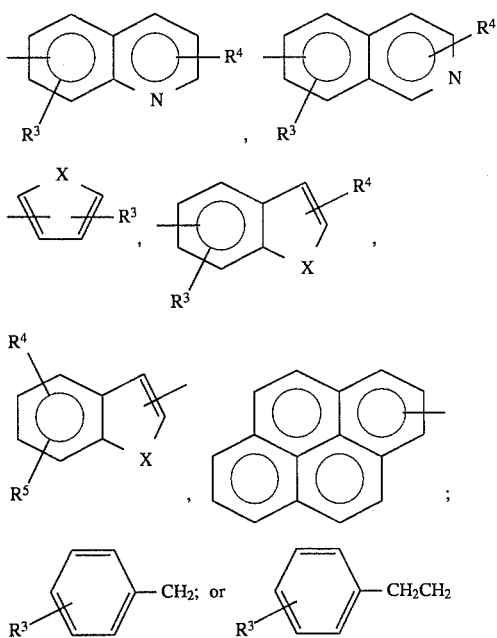

Z is carbonyl (C=O) or thiocarbonyl (C=S);

Y is carbon substituted by halo, $(C_1–C_6)$alkoxy, $(C_3–C_6)$alkynylthio or triazolyl;
wherein
$R^1$ is $(C_1–C_6)$ straight or branched alkyl, hydroxy$(C_1–C_6)$alkyl, cyano$(C_1–C_6)$alkyl, $(C_3–C_6)$cycloalkylalkyl, $(C_1–C_6)$alkyl, heterocyclyl$(C_1–C_6)$alkyl, phenyl, phenyl$(C_1–C_6)$alkyl, $(C_3–C_6)$alkenyl, halo$(C_3–C_6)$alkenyl, phenyl$(C_3–C_6)$alkenyl, $(C_3–C_6)$alkynyl$(C_2–C_6)$alkenyl, $(C_3–C_{10})$ alkynyl, $(C_4–C_{20})$dialkynyl, halo$(C_3–C_6)$alkynyl, phenyl$(C_3–C_6)$alkynyl, heterocyclyl$(C_3–C_6)$alkynyl, $(C_3–C_6)$cycloalkyl$(C_3–C_6)$alkynyl, $(C_3–C_6)$alkenyl$(C_3–C_6)$alkynyl, hydroxy$(C_3–C_6)$alkynyl, $(C_1–C_6)$alkoxy $(C_3–C_6)$alkynyl, $(C_1–C_6)$alkanoyloxy $(C_3–C_6)$alkynyl, formyl$(C_3–C_6)$alkynyl, tri-$(C_1–C_6)$alkylsilyl $(C_3–C_6)$alkynyl, tri$(C_1–C_6)$alkyltin $(C_3–C_6)$alkynyl, halo$(C_3–C_6)$alkenyl $(C_3–C_6)$alkynyl, carboxy$(C_3–C_6)$alkynyl, or $(C_1–C_6)$alkoxycarbonyl$(C_3–C_6)$alkynyl.

$R^7$ can be hydrogen, $(C_1–C_3)$alkyl, phenyl, cyano, halogen, $(C_3–C_{10})$alkynyl, $(C_3–C_6)$alkynyl$(C_2–C_6)$alkenyl, $(C_4–C_{20})$dialkynyl, halo$(C_3–C_6)$alkynyl, or $(C_3–C_6)$alkenyl$(C_3–C_6)$alkynyl;

$R^8$ is hydrogen, $(C_1–C_3)$alkyl, phenyl, cyano or halogen;
$R^3$ and $R^6$ are independently hydrogen, or halogen
$R^4$ is hydrogen, halogen, $(C_1–C_6)$alkoxy or nitro;
$R^5$ is hydrogen, halogen, nitro, $(C_1–C_6)$alkyl, $(C_1–C_6)$alkoxy, $(C_1–C_6)$ alkylthio, halo$(C_1–C_6)$alkyl, halo$(C_1–C_6)$alkoxy, halo$(C_1–C_6)$alkylthio, phenyl, phenoxy or cyano; or $R^2$ and $R^3$ together form a $(C_1–C_3)$alkyl, $(C_2–C_3)$alkylene or carbonyl link; or $R^2$ and $R^7$ together form a fused phenyl ring;
X is oxygen (O) or sulfur (S); and
n is 0, 1 or 2; and
agronomically acceptable salts thereof.

In a more preferred embodiment of the invention the compounds used have the formula

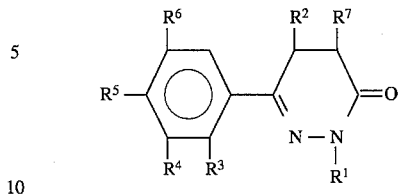

wherein
$R^1$ is $(C_1–C_6)$ straight or branched alkyl, hydroxy$(C_1–C_6)$alkyl, cyano$(C_1–C_6)$alkyl, $(C_3–C_6)$cycloalkyl $(C_1–C_6)$alkyl, heterocyclyl $(C_1–C_6)$alkyl, phenyl, phenyl$(C_1–C_6)$alkyl, $(C_3–C_6)$alkenyl, halo$(C_3–C_6)$alkenyl, phenyl$(C_3–C_6)$alkenyl, $(C_3–C_6)$alkynyl$(C_2–C_6)$alkenyl, $(C_3–C_{10})$alkynyl, $(C_4–C_{20})$dialkynyl, halo$(C_3–C_6)$alkynyl, phenyl$(C_3–C_6)$alkynyl, heterocyclyl$(C_3–C_6)$alkynyl, $(C_3–C_6)$cycloalkyl $(C_3–C_6)$alkynyl, $(C_3–C_6)$alkenyl$(C_3–C_6)$alkynyl, hydroxy$(C_3–C_6)$alkynyl, $(C_1–C_6)$alkoxy $(C_3–C_6)$alkynyl, $(C_1–C_6)$alkanoyloxy $(C_3–C_6)$alkynyl, formyl$(C_3–C_6)$alkynyl, tri$(C_1–C_6)$alkylsilyl $(C_3–C_6)$alkynyl, tri$(C_1–C_6)$alkyltin$(C_3–C_6)$ alkynyl, halo$(C_3–C_6)$alkenyl $(C_3–C_6)$alkynyl, carboxy$(C_3–C_6)$alkynyl, or $(C_1–C_6)$alkoxycarbonyl$(C_3–C_6)$alkynyl. $R^2$ is hydrogen or $(C_1–C_6)$alkyl;
$R^3$ is hydrogen, halogen, $(C_1–C_6)$alkyl, or $(C_1–C_6)$alkoxy;
or
$R^2$ and $R^3$ together form a $(C_1–C_3)$alkyl, $(C_2–C_3)$alkenyl or carbonyl link;
$R^4$ is hydrogen, $(C_1–C_6)$alkyl, halogen or nitro;
$R^5$ is hydrogen, $(C_1–C_6)$alkyl, $(C_1–C_6)$alkoxy, phenoxy, halo$(C_1–C_6)$alkyl, $(C_1–C_6)$alkylthio, cyano, phenyl, halo$(C_1–C_6)$alkoxy or halogen;
$R^6$ is hydrogen or halogen; and
$R^7$ is hydrogen, $(C_1–C_6)$alkyl, phenyl or halogen, $(C_3–C_{10})$alkynyl, $(C_3–C_6)$alkynyl$(C_2–C_6)$alkenyl, $(C_4–C_{20})$dialkynyl, halo$(C_3–C_6)$alkynyl, or $(C_3–C_6)$alkenyl$(C_3–C_6)$alkynyl;
and agronomically acceptable salts thereof.

More preferred are compounds wherein
$R^1$ is $(C_3–C_{10})$alkynyl, $(C_3–C_6)$alkenyl, $(C_3–C_6)$alkenyl$(C_3–C_6)$alkynyl or $(C_3–C_6)$alkynyl$(C_3–C_6)$alkenyl;
$R^2$ is hydrogen or $(C_1–C_6)$alkyl;
$R^3$ is hydrogen, halo or $(C_1–C_6)$alkoxy;
$R^2$ and $R^3$ together form a $(C_1–C_3)$alkyl, $(C_2–C_3)$alkenyl or carbonyl link;
$R^4$ is hydrogen, halo or $(C_1–C_6)$alkyl;
$R^5$ is hydrogen, halo or halo$(C_1–C_6)$alkoxy;
$R^6$ is hydrogen or fluoro; and
$R^7$ is hydrogen.

Even more preferred compounds of this embodiment are compounds wherein $R^1$ is 2-pentynyl, 2-hexynyl, 3-vinyl-2-propynyl, 4-fluoro-2-pentynyl, 5-fluoro-2-pentynyl, or 3-(1-propenyl)-2-propynyl, $R^2$ is hydrogen, $R^3$ is hydrogen, $R^2$ and $R^3$ can together form a $(C_1–C_3)$alkyl link;

$R^4$ is hydrogen, methyl, chloro or fluoro, $R^5$ is chloro, fluoro, bromo or trifluoromethoxy, $R^6$ is hydrogen or fluoro and $R^7$ is hydrogen.

Preferred compounds where $R^1$ is 2-pentynyl are those in which $R^2$, $R^3$, $R^6$ and $R^7$ are hydrogen, $R^5$ is chloro and $R^4$ is hydrogen or fluoro.

In a second preferred embodiment are compounds of the structure $$\text{R}^5 \underset{\text{R}^4}{\overset{\text{R}^6}{\diagdown}} \diagup \diagdown \diagup \overset{\text{R}^2 \quad \text{R}^7}{\diagup \diagdown} =\text{O}$$
(with N—N—R$^1$ ring)

wherein
$R^1$ is $(C_3-C_6)$alkynyl, $(C_2-C_6)$alkynyl$(C_3-C_6)$alkynyl, halo$(C_3-C_6)$ alkynyl, $(C_2-C_6)$alkenyl$(C_3-C_6)$alkynyl or tri-$((C_1-C_6)$alkyl)in$(C_3-C_6)$-alkynyl;
$R^2$ is hydrogen or halogen;
$R^3$ is hydrogen or $(C_1-C_6)$alkyl; or
$R^2$ and $R^3$ together form a $(C_1-C_3)$alkyl, $(C_2-C_3)$alkenyl or carbonyl link;
$R^4$ is hydrogen, halogen or $(C_1-C_6)$alkyl;
$R^5$ is hydrogen, halogen, $(C_1-C_6)$alkyl; or $(C-C_6)$alkoxy;
$R^6$ is hydrogen or halogen; and
$R^7$ is hydrogen or halogen; and
agronomically acceptable salts thereof.

More preferred compounds of this embodiment are compounds wherein $R^1$ is $(C_3-C_6)$alkynyl;
$R^2$ is hydrogen or halo;
$R^2$ and $R^3$ together form a $(C_1-C_3)$alkyl link;
$R^3$ is hydrogen or $(C_1-C_6)$alkyl;
$R^4$ is hydrogen, halo or $(C_1-C_6)$alkyl;
$R^5$ is hydrogen, halo, $(C_1-C_6)$alkyl, or $(C_1-C_6)$alkoxy;
$R^6$ is hydrogen or fluoro; and
$R^7$ is hydrogen or fluoro.

Even more preferred are compounds wherein $R^1$ is 2-pentynyl, 4-fluoro-2-pentynyl, 3-vinyl-2-propynyl, or 5-fluoro-2-pentynyl, $R^2$ is hydrogen, $R^3$ is hydrogen, $R^2$ and $R^3$ together form a $(C_1-C_3)$alkyl link; $R^4$ is hydrogen, fluoro or chloro, $R^5$ is fluoro, chloro or bromo, $R^6$ is hydrogen, and $R^7$ is hydrogen.

Preferred are compounds wherein $R^1$ is 2-pentynyl; $R^2$, $R^3$, $R^6$ and $R^7$ are hydrogen; $R^4$ is hydrogen or fluoro and $R^5$ is chloro.

Certain compounds which are useful in the method of the instant invention are known and commercially available. However, they have not previously been disclosed to be active against *Pyricularia oryzae* and thus they have not been disclosed to be active in the method of the instant invention. These compounds include compounds 1–5 listed in Table I below.

The dihydropyridazinones compounds of the instant invention are prepared, for example, by a two-step sequence starting from an arylketo acid or ester of the formula $$\underset{\text{Q}-\text{CCH}_2\text{CH}_2\text{COR}^a}{\overset{\text{O} \quad \text{O}}{\|\quad\|}}$$ 
II wherein Q is as defined in Formula I above and $R^a$ is hydrogen or alkyl. Compound II is reacted with about an equivalent of hydrazine or a substituted hydrazine having the formula $$\text{H}_2\text{NNHR}^b$$
III wherein $R^b$ is hydrogen to yield a compound having the formula $$\text{Q} - \diagup \diagdown \diagup =\text{O}$$
(with N—N—R$^b$ ring)
IV Examples of suitable solvents for this reaction include alcohols, such as ethanol, n-propanol or n-butanol. The reaction is generally carried out at about atmospheric pressure at a temperature of from about −10° C. to about 200° C. Preferably, the temperature employed is in the range of from about 25° C. to about 150° C., more preferably from about 50° C. to about 125° C.

The compound of Formula IV wherein $R^b$ is hydrogen is then alkylated using the appropriate alkylating agent, for example an alkynyl mesylate or alkynyl halide, by a standard N-alkylation procedure, for example, using sodium hydride in an aprotic polar solvent such as dimethylformamide (DMF) or by using a phase transfer catalyst such as tetrabutylammonium hydrogen sulfate to obtain the desired dihydro-pyridazinone (formula IV wherein $R^b$ is not hydrogen) of the instant invention. The reaction is generally carried out at a temperature of from about −10° C. to about 250° C. More preferably, the reaction is carried out at a temperature of from about 20° C. to about 100° C.

The dihydropyridazinone of Formula IV wherein $R^b$ is hydrogen can be converted to the corresponding pyridazinone of the invention, for example, by bromine oxidation. The reaction is generally carried out in an organic acid solvent such as acetic acid at a temperature of from about 0° C. to about 150° C. More preferably, the temperature ranges from about 20° C. to about 100° C., more particularly from about 50° C. to about 75° C.

The starting arylketoacids can be obtained from commercial sources or prepared by procedures known in the literature such as 1) Friedel-Crafts acylation of aromatic compounds with succinic anhydride, 2) a malonic ester condensation (the preparation of biso(di-t-butyl-carboxy-)ethylcarboxyethane from di-t-butylmalonate, acylation with an aromatic acyl chloride and decarboxylation of the ketotriester) or 3) a Claisen condensation.

Typically, the alkynyl mesylates and alkynyl halides used in the alkylation step of the procedure are prepared by means known in the art, for example:

a) from commercially available alcohols $$R^7-C\equiv CCH_2OH \xrightarrow{CH_3SO_2Cl}$$

$$R^7-C\equiv CCH_2OSO_2CH_3 \xrightarrow{LiBr} R^7-C\equiv CCH_2Br$$

b) from commercially available alkynes $$R^7-C\equiv CH \xrightarrow[\text{2) RCHO}]{\text{1) n-BuLi}}$$

$$R^7-C\equiv CCH(OH)R \longrightarrow \text{as in scheme a}$$

$$R^7-C\equiv CH + (CH_2O)_n \xrightarrow[Et_2O]{EtMgBr} R^7-C\equiv CCH_2OH$$

c) from propargyl chloride

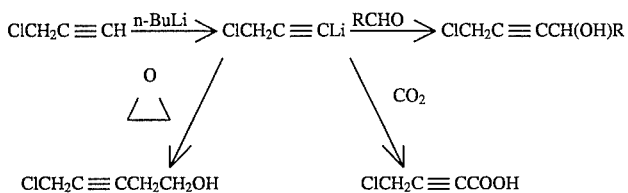

wherein $R^7$ is alkyl, cycloalkyl, etc. and R is, for example, alkyl.

Additionally, the alkynyl group can be modified after the alkylation step has taken place, for example by treatment with diethylaminosulfur trifluoride (DAST), acetic anhydride, alcohol/hydrogen chloride to add fluorine, acetyl or an alkoxy group to the carbon alpha to the alkynyl or treatment with a haloalkene in the presence of bis(triphenylphosphine)palladium dichloride, copper(I) iodide and triethylamine to add an alkenyl group to the alpha carbon of the alkyne:

a)

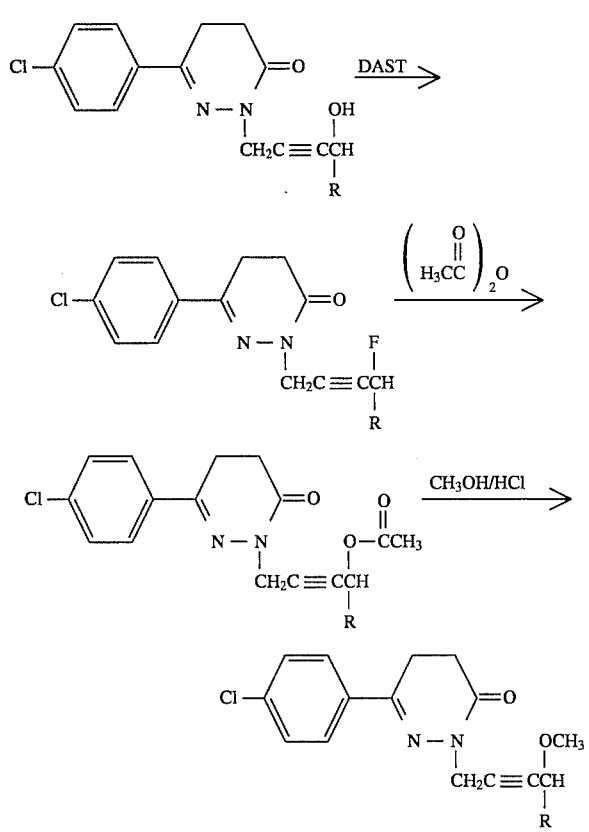

b)

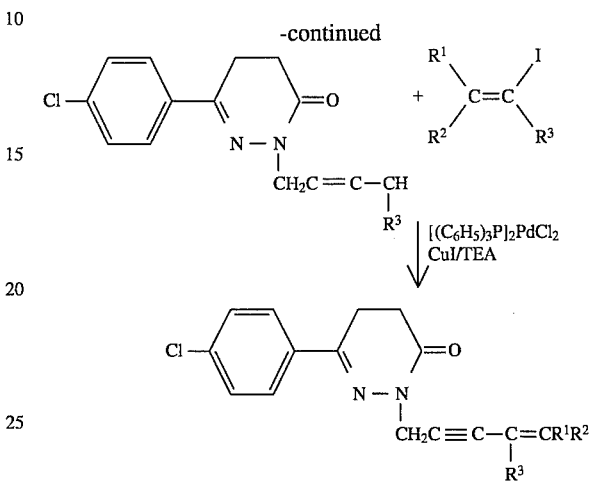

The pyridinones are prepared, for example, by cyclization of 2-aryldialkylamino propenals (V) and a cyanoacetamide (VI) in the presence of base to yield the corresponding 3-cyano-5-aryl-pyridinone (VII)

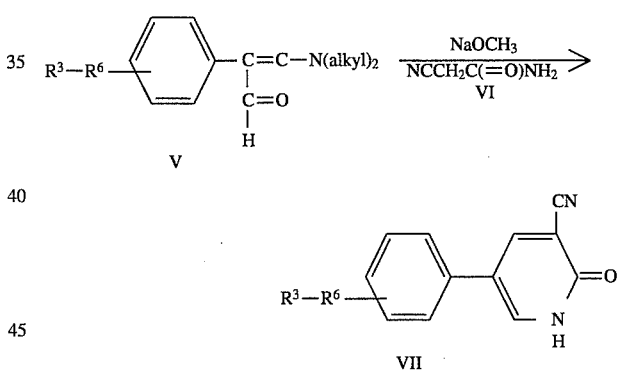

which is then hydrolyzed and decarboxylated to yield the pyridinone (VIII).

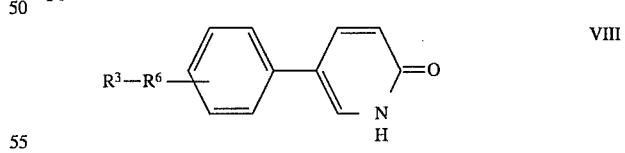

The pyridinone is alkylated as described above for the dihydropyridazinones to yield compounds of the invention.

Examples of suitable solvents for the cyclization reaction include alcohols, such as methanol or ethanol. Examples of suitable bases include sodium methoxide and sodium ethoxide. The reaction is generally carried out at about atmospheric pressure at a temperature of from about 25° C. to about 250° C. Preferably, the temperature employed is in the range of from about 50° C. to about 200° C., more preferably from about 100° C. to about 150° C.

The hydrolysis and decarboxylation step is typically carried out in a strong acid such as 85% $H_3PO_4$ or concentrated sulfuric acid at atmospheric pressure at temperatures between 50° and 200° C., preferably between 100°–150° C.

The starting pyrimidinones (IX) of the invention can be made by

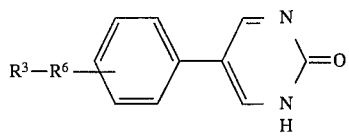

cyclizing 2-aryl dialkylamino propenals (V) with urea in the presence of acid. Preferred acids are mineral acids such as hydrochloric acid. Preferred solvents are polar solvents, for example alcohols such as ethanol. The reaction is preferably carried out at atmospheric pressure at a temperature between 20° and 200° C., more preferably between 50° and 150° C. The alkylation is then carried out as described above for the dihydropyridazinones.

The starting oxadiazin-2-ones (X) of the invention can be prepared

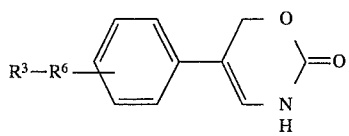

by reacting an α-hydroxy acetophenone (XI) with ethyl carbazate (XII) in

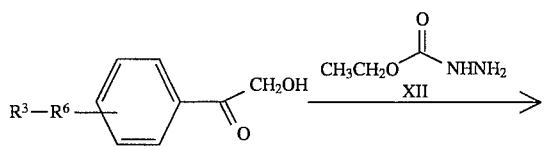

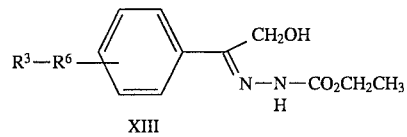

a polar solvent, for example, an alcohol such as ethanol preferably at a temperature between 0° and 150° C., more preferably between 15° and 70° C. to obtain compound XIII which is then cyclized in a polar solvent, for example, an alcohol such as ethanol, in the presence of base such as sodium hydride to yield the oxadiazin-2-one (X). Alkylation as described above for the dihydropyridazinones yields compounds of the instant invention.

The starting oxadiazin-5-ones (XIV) can be prepared by reacting a

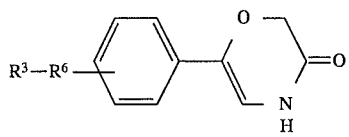

substituted benzoic hydrazide (XV) with a haloacetyl chloride (XVI) in

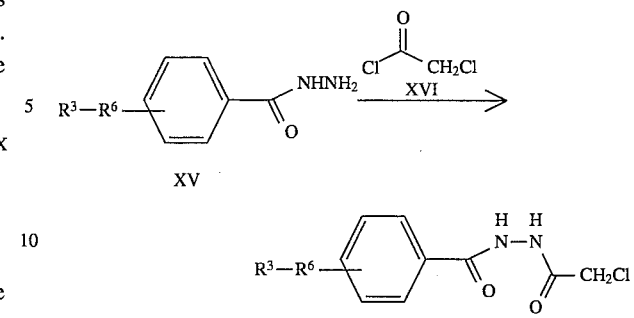

an aprotic solvent such as dioxane, tetrahydrofuran, glyme or other poylether, preferably at a temperature between 0° and 150° C., more preferably between 50° and 100° C. to obtain compound XVII which is subsequently cyclized in the presence of a base such as sodium hydroxide to yield the oxadiazin-5-one (XIV). Alkylation as described above for the dihydropyridazinones yields compounds of the instant invention.

The starting thiadiazin-2-ones (XVIII) can be prepared by reacting a

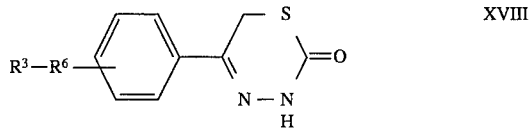

phenacyl halide (XIX), preferably a phenacyl bromide, with an alkoxythiocarbonyl hydrazine (XX) such as methyl thiocarbazate in a

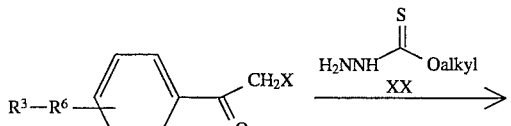

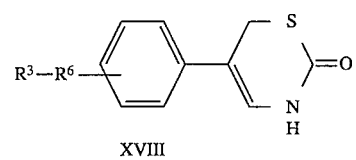

polar solvent such as acetonitrile, dimethylformamide or an alcohol, more preferably acetonitrile, preferably at a temperature between 0° and 150° C., more preferably between 50° and 100° C. to obtain compound XVIII. Alkylation as described above for the dihydropyridazinones yields compounds of the instant invention.

The starting indenopyridazinones (XXI), wherein $R^8$ is hydrogen or

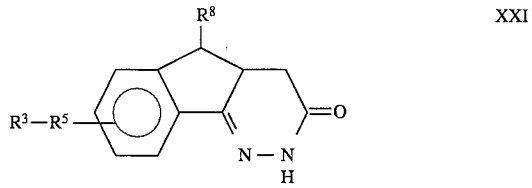

$(C_1-C_6)$alkyl, can be prepared by carboxymethylating the appropriate indanone (XXII) using an agent such as dimethylcarbonate in the presence of base such as sodium hydride and an aprotic solvent such as dimethoxyethane, followed by alkylation with an agent such as ethyl bromoacetate in the presence of base such as sodium hydride and an aprotic solvent such as dimethylformamide to obtain the diester (XXIII).

The diester is subsequently decarboxylated and hydrolyzed using standard procedures, preferably heating in a aqueous acid solution, more preferably, refluxing in aqueous hydrochloric acid to obtain the corresponding ketoacid (XXIV) which is cyclized and alkylated as described above

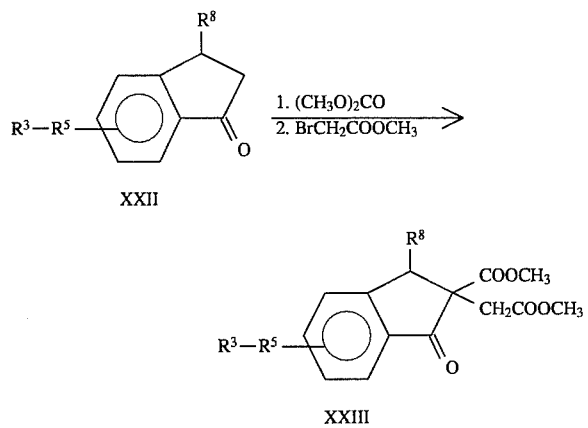

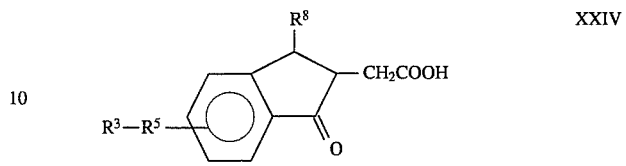

for the dihydropyridazinones to yield compounds of the instant invention.

The following examples will further illustrate this invention, but are not intended to limit it in any way. In Tables I to III examples of compounds of the invention are listed. For compounds that are new, elemental analyses are listed in Table IV or proton NMR data is listed in Table V. Specific illustrative preparations of the compounds are described after Table V.

TABLE I

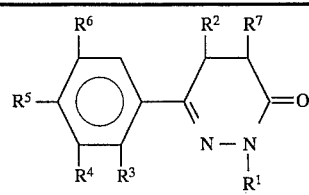

| Compound Number | $R^1$ | $R^2$ | $R^3$ | $R^4$ | $R^5$ | $R^6$ | $R^7$ |
|---|---|---|---|---|---|---|---|
| 1. | $CH_2C \equiv CCH_3$ | H | H | H | Cl | H | H |
| 2. | $(CH_2)_3OH$ | H | H | H | $OCH_3$ | H | H |
| 3. | $CH_2CH(OH)CH_2CH_3$ | H | H | Cl | Cl | H | H |
| 4. | $CH_2CH(OH)CH_2CH_3$ | H | H | H | Cl | H | H |
| 5. | $(CH_2)_3OH$ | H | H | Cl | Cl | H | H |
| 6. | $CH_2C \equiv CH$ | H | H | H | Cl | H | H |
| 7. | $(CH_2)_3CH_3$ | H | H | H | Cl | H | H |
| 8. | $CH_2CH = CHCH_3$ | H | H | H | Cl | H | H |
| 9. | $CH_2C \equiv CCH_3$ | H | H | H | H | H | H |
| 10. | $CH_2C_6H_5$ | H | H | H | Cl | H | H |
| 11. | $CH_2C \equiv CCH_3$ | H | H | H | $OCH_3$ | H | H |
| 12. | $CH_2C \equiv CCH_2CH_3$ | H | H | H | Cl | H | H |
| 13. | $CH_2C \equiv CCH_3$ | H | H | H | F | H | H |
| 14. | $C_6H_5$ | H | H | H | Cl | H | H |
| 15. | $C(CH_3)_3$ | H | H | H | Cl | H | H |
| 16. | $C(=O)C_6H_5$ | H | H | H | Cl | H | H |
| 17. | $CH_2C \equiv CC_6H_5$ | H | H | H | Cl | H | H |
| 18. | $CH_2C \equiv CCH_3$ | H | H | H | $CH_3$ | H | H |
| 19. | $CH_2C \equiv CCH_3$ | H | Cl | H | Cl | H | H |
| 20. | $CH_2C \equiv CCH_3$ | H | H | F | $OCH_3$ | H | H |
| 21. | $CH_2CH_2C \equiv CCH_3$ | H | H | H | Cl | H | H |
| 22. | $CH(CH_3)C \equiv CCH_3$ | H | H | H | Cl | H | H |
| 23. | $CH_2C \equiv CCH_3$ | H | H | Cl | Cl | H | H |
| 25. | $CH_2$-cyclopropyl | H | H | H | Cl | H | H |

TABLE I-continued

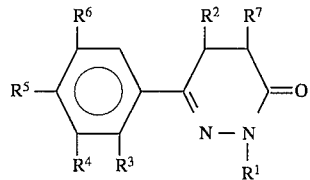

| Compound Number | R¹ | R² | R³ | R⁴ | R⁵ | R⁶ | R⁷ |
|---|---|---|---|---|---|---|---|
| 26. | $CH_2C\equiv CCH_3$ | $CH_3$ | H | H | Cl | H | H |
| 27. | $CH_2C\equiv CCH_3$ | H | H | H | Cl | H | $CH_3$ |
| 28. | $CH_2C\equiv CCH_2CH_3$ | H | H | Cl | Cl | H | H |
| 29. | $CH_2C\equiv CCH_2CH_2CH_3$ | H | H | H | Cl | H | H |
| 30. | $CH_2C\equiv CCH_3$ | H | H | H | H | H | $C_6H_5$ |
| 31. | $CH_2C\equiv CCH_3$ | H | H | H | Br | H | H |
| 32. | $CH_2CH=C(CH_3)_2$ | H | H | H | Cl | H | H |
| 33. | $CH_2C\equiv CCH_3$ | H | H | H | $OC_6H_5$ | H | H |
| 34. | $CH_2C\equiv CCH(CH_3)_2$ | H | H | H | Cl | H | H |
| 35. | $CH_2CN$ | H | H | H | Cl | H | H |
| 36. | 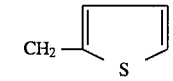 | H | H | H | Cl | H | H |
| 37. | $CH_2C\equiv CCH_3$ | H | H | Cl | H | H | H |
| 38. | $CH_2C\equiv CCH_3$ | H | H | Cl | H | Cl | H |
| 39. | $CH_2C\equiv CCH_3$ | H | H | $NO_2$ | Cl | H | H |
| 40. | $CH_2C\equiv CCH_2CH_3$ | H | H | $NO_2$ | Cl | H | H |
| 41. | $CH_2C\equiv CCH_2CH_3$ | H | H | H | $CF_3$ | H | H |
| 42. | $CH_2C\equiv CCH_3$ | H | H | H | $CF_3$ | H | H |
| 43. | $CH_2C\equiv CCH_2CH_3$ | H | Cl | Cl | $CH_3$ | Cl | H |
| 44. | $CH_2C\equiv CCH_2CH_3$ | H | H | Cl | $CH_3$ | Cl | H |
| 45. | $CH_2C\equiv CC(CH_3)=CH_2$ | H | H | H | Cl | H | H |
| 46. | $CH_2C\equiv CC(CH_3)_3$ | H | H | H | Cl | H | H |
| 47. | $CH_2C\equiv CCH(CH_3)OH$ | H | H | H | Cl | H | H |
| 48. | $CH_2C\equiv CCH(CH_3)OCH_3$ | H | H | H | Cl | H | H |
| 49. | $CH_2C\equiv CCH(CH_3)OC(=O)CH_3$ | H | H | H | Cl | H | H |
| 50. | $CH_2C\equiv CCH_2OH$ | H | H | H | Cl | H | H |
| 51. | $CH_2C\equiv CCH_2F$ | H | H | H | F | H | H |
| 52. | $CH=C=CH_2$ | H | H | H | Cl | H | H |
| 53. | $CH_2C\equiv CCHFCH_3$ | H | H | H | Cl | H | H |
| 54. | $CH_2C\equiv CCOOH$ | H | H | H | Cl | H | H |
| 55. | $CH_2C\equiv CCOOCH_3$ | H | H | H | Cl | H | H |
| 56. | $CH_2C\equiv CCH=CH_2$ | H | H | H | Cl | H | H |
| 57. | $CH_2C\equiv CCH_2CH_3$ | H | H | H | $C(CH_3)_3$ | H | H |
| 58. | $CH_2C\equiv CCH_3$ | H | H | H | $CH_2CH_3$ | H | H |
| 59. | $CH_2C\equiv CCH_2CH_3$ | H | H | H | $CH_2CH_3$ | H | H |

TABLE I-continued

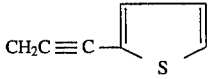

| Compound Number | R¹ | R² | R³ | R⁴ | R⁵ | R⁶ | R⁷ |
|---|---|---|---|---|---|---|---|
| 60. | CH₂C≡CCl | H | H | H | Cl | H | H |
| 61. | CH₂C≡CCH₂CH₃ | H | H | H | SCH₃ | H | H |
| 62. | CH₂C≡CCH₂CH₃ | H | H | CH₃ | Cl | H | H |
| 63. | CH₂C≡CCH₃ | H | H | CH₃ | Cl | H | H |
| 64. | CH₂C≡CCH₂CH₃ | H | H | H | CN | H | H |
| 65. | CH₂C≡CCH₂CH₃ | H | H | H | NO₂ | H | H |
| 66. | CH₂C≡CCH₂CH₃ | H | H | H | OCH₂CH₃ | H | H |
| 67. |  | | | | | | |
| 68. | CH₂C≡CC₆H₄-4-Cl | H | H | H | Cl | H | H |
| 69. | CH₂CH=CHBr | H | H | H | Cl | H | H |
| 70. | CH₂CH=CHC≡CCH(CH₃)₂ | H | H | H | Cl | H | H |
| 71. | CH₂C≡CCH₂Br | H | H | H | Cl | H | H |
| 72. | CH₂C≡CCH₂Cl | H | H | H | Cl | H | H |
| 73. | CH₂C≡CCH₂CH₃ | H | F | H | Cl | H | H |
| 74. | CH₂C≡CCH₂CH₃ | H | H | F | Cl | H | H |
| 75. | CH₂CH=C(Br)CH₂Br | H | H | H | Cl | H | H |
| 76. | CH₂C≡CCH₂F | H | H | H | Cl | H | H |
| 77. | CH₂C≡C—⟨epoxide⟩ | H | H | H | Cl | H | H |
| 78. | CH₂C≡CCF—CF₂ | H | H | H | Cl | H | H |
| 79. | CH₂C≡CCH₂CH₃ | H | H | H | C₆H₅ | H | H |
| 80. | CH₂C≡CCH₂CH₃ | H | H | H | CH₃ | H | H |
| 81. | CH₂C≡CCH₂CH₃ | H | H | H | OCH₃ | H | H |
| 82. | CH₂C≡CCH₂CH₃ | H | H | H | F | H | H |
| 83. | CH₂C≡CCH₃ | H | H | F | Cl | H | H |
| 84. | CH₂CH=CHC≡CH | H | H | H | Cl | H | H |
| 85. | CH₂C≡C(CH₂)₆CH₃ | H | H | H | Cl | H | H |
| 86. | CH₂C≡CSi(CH₃)₃ | H | H | H | Cl | H | H |
| 87. | CH₂C≡CCH(OCH₂CH₃)₂ | H | H | H | Cl | H | H |
| 88. | CH₂C≡CCHO | H | H | H | Cl | H | H |
| 89. | CH₂C≡CCHF₂ | H | H | H | Cl | H | H |
| 90. | CH₂C≡CCH₂CH₃ | H | H | F | Cl | H | H |
| 91. | CH₂C≡CCH₂CH₃ | H | H | H | Br | H | H |
| 92. | CH₂C≡CCH₂CH₃ | H | H | F | OCF₃ | H | H |

TABLE I-continued

[Structure: phenyl ring with R⁴, R³, R⁵, R⁶ substituents connected to a pyridazinone ring bearing R², R⁷, and N-R¹, with C=O]

| Compound Number | R¹ | R² | R³ | R⁴ | R⁵ | R⁶ | R⁷ |
|---|---|---|---|---|---|---|---|
| 93. | CH₂C≡CC≡CH | H | H | H | Cl | H | H |
| 94. | CH₂C≡C-cyclohexyl | H | H | H | Cl | H | H |
| 95. | CH₂C≡CCH₂-cyclohexyl | H | H | H | Cl | H | H |
| 96. | CH₂C≡C(CH₂)₄CH₃ | H | H | H | Cl | H | H |
| 97. | CH₂C≡CCH₂CH₃ | H | H | F | Br | H | H |
| 98. | CH₂C≡CCH₂CH₃ | H | H | F | H | F | H |
| 99. | CH₂C≡CCH₂CH₃ | H | OCH₃ | H | Cl | H | H |
| 100. | CH₂C≡CCH=CH₂ | H | H | F | Cl | H | H |
| 101. | CH₂C≡CCH=CHCH₃ | H | H | H | Cl | H | H |
| 102. | CH₂C≡CCH=CHCH₃(cis) | H | H | H | Cl | H | H |
| 103. | CH₂C≡CCH=CHCH₃(trans) | H | H | H | Cl | H | H |
| 104. | CH₂C≡CCH₂CH₃ | H | H | Cl | F | H | H |
| 105. | CH₂C₆H₅—3Cl | H | H | H | Cl | H | H |
| 201 | CH₃ | H | H | H | Cl | H | H |
| 203 | CH₃ | H | H | H | Cl | H | CH₂C≡CH₂CH₃ |
| 207 | CH₂C≡CCH₂CH₃ | H | H | H | O···CH₂···O | | H |
| 208 | CH(CH₃)C≡CCH₂CH₃ | H | H | H | Cl | H | H |
| 209 | CH₂C≡CCH₂CH₃ | H | F | H | H | H | H |
| 210 | CH₂C≡CCH₂CH₃ | H | CH₃ | H | H | H | H |
| 211 | CH₂C≡CCH₂CH₃ | H | Cl | H | H | H | H |
| 212 | CH₂C≡CCH₂CH₃ | H | OCH₃ | H | H | H | H |
| 213 | CH₂C≡CCH₂CH₃ | H | H | CF₃ | H | H | H |
| 214 | CH₂C≡CCH₂CH₃ | H | H | F | H | H | H |
| 215 | CH₂C≡CCH₂CH₃ | H | H | CH₃ | H | H | H |
| 216 | CH₂C≡CCH₂CH₃ | H | H | Cl | H | H | H |
| 217 | CH₂C≡CCH₂CH₃ | H | H | CN | H | H | H |
| 218 | CH₂C≡CCH₂CH₃ | H | H | CF₃ | H | H | H |
| 219 | CH₂C≡CCH₂CH₃ | H | H | OCH₃ | H | H | H |
| 220 | CH₂C≡CCH₂CH₃ | H | H | OCH₃ | CH₃ | H | H |
| 221 | CH₂C≡CCH₂CH₃ | H | H | Cl | OCH₃ | H | H |
| 222 | CH₂C≡CCH₂CH₃ | H | H | Br | F | H | H |

TABLE I-continued
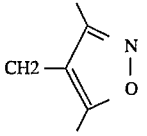
| Compound Number | R¹ | R² | R³ | R⁴ | R⁵ | R⁶ | R⁷ |
|---|---|---|---|---|---|---|---|
| 223 | CH₂C≡CCH₂CH₃ | H | H | NO2 | OCH₃ | H | H |
| 224 | CH₂C≡CCH₂CH₃ | H | H | F | F | H | H |
| 225 | CH₂C≡CCH₂CH₃ | H | H | F | CH₃ | H | H |
| 226 | CH₂C≡CCH₂CH₃ | H | H | CH₃ | OCH₃ | H | H |
| 231 | 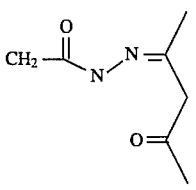 | H | H | H | Cl | H | H |
| 233 | CH₂CONHNH₂ | H | H | H | Cl | H | H |
| 234 | 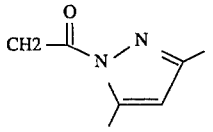 | H | H | H | Cl | H | H |
| 237 | 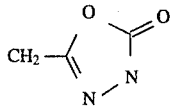 | H | H | H | Cl | H | H |
| 238 | 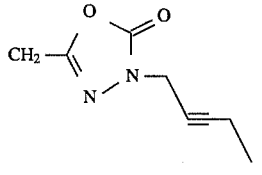 | H | H | H | Cl | H | H |
| 239 | 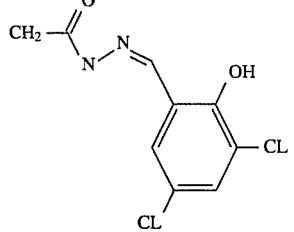 | H | H | H | Cl | H | H |
| 240 |  | H | H | H | Cl | H | H |

TABLE I-continued

[Structure: phenyl ring with R³, R⁴, R⁵, R⁶ substituents connected to a ring containing R², R⁷, C=O, N—N—R¹]

| Compound Number | R¹ | R² | R³ | R⁴ | R⁵ | R⁶ | R⁷ |
|---|---|---|---|---|---|---|---|
| 241 | [structure: CH₂—C(=CH₂)—C(=O)—O—N(—N=)—CH₂C≡C—I] | H | H | H | Cl | H | H |

TABLE II

[Structure: phenyl ring with R³, R⁴, R⁵, R⁶ substituents connected to a ring containing R², R⁷ with a double bond, C=O, N—N—R¹]

| Compound Number | R¹ | R² | R³ | R⁴ | R⁵ | R⁶ | R⁷ |
|---|---|---|---|---|---|---|---|
| 108. | $CH_2C \equiv CCH_3$ | H | H | H | Cl | H | H |
| 109. | $CH_2C \equiv CCH_2CH_3$ | H | H | H | Cl | H | H |
| 110. | $CH_2C \equiv CCH_2CH_3$ | H | H | H | $CH_2CH_3$ | H | H |
| 111. | $CH_2C \equiv CCH_2CH_3$ | H | H | H | $C(CH_3)_3$ | H | H |
| 112. | $CH_2C \equiv CCH_2CH_3$ | H | H | Cl | Cl | H | H |
| 113. | $CH_2C \equiv CCH_2CH_3$ | H | H | $CH_3$ | Cl | H | H |
| 114. | $CH_2C \equiv CCH_3$ | H | H | $CH_3$ | Cl | H | H |
| 115. | $CH_2C \equiv CCH_2CH_3$ | H | $CH_3$ | H | Cl | H | H |
| 116. | $CH_2C \equiv CCH_3$ | H | $CH_3$ | H | Cl | H | H |
| 117. | $CH_2C \equiv CCH_2CH_3$ | H | H | H | $OCH_2CH_3$ | H | H |
| 118. | $CH_2C \equiv CH$ | H | H | H | Cl | H | H |
| 119. | $CH_2C \equiv CCH=CH_2$ | H | H | H | Cl | H | H |
| 120. | $CH_2C \equiv CCH_2CH_3$ | H | H | F | Cl | H | H |
| 121. | $CH_2C \equiv CCH_2CH_3$ | H | H | H | Br | H | H |
| 122. | $CH_2C \equiv CCH_2CH_3$ | F | H | H | Cl | H | F |
| 123. | $CH_2C \equiv CCH_2CH_3$ | F | H | H | Cl | H | H |
| 124. | $CH_2C \equiv CSn(C_4H_9-n)_3$ | H | H | H | Cl | H | H |
| 125. | $CH_2C \equiv CC \equiv CH$ | H | H | H | Cl | H | H |
| 126. | $CH_2C \equiv CCH_2CH_3$ | H | H | F | H | F | H |
| 127. | $CH_2C \equiv CCH_2CH_3$ | H | H | F | Br | H | H |
| 128. | $CH_2C \equiv CCH=CH_2$ | H | H | F | Cl | H | H |
| 129. | $CH_2C \equiv CCH_2CH_3$ | H | H | Cl | F | H | H |
| 130. | $CH_2C \equiv CCHFCH_3$ | H | H | H | Cl | H | H |

TABLE II-continued

| Compound Number | R¹ | R² | R³ | R⁴ | R⁵ | R⁶ | R⁷ |
|---|---|---|---|---|---|---|---|
| 131. | $CH_2C{\equiv}CCH_2F$ | H | H | H | Cl | H | H |
| 204 | $CH_2$-(2,5-dimethylfuran) | H | H | H | Cl | H | H |
| 228 | $CH_2C{\equiv}CCH_2CH_3$ | phenyl | H | H | H | H | CN |

TABLE III 24. 4-chlorophenyl-CH=CH-pyridazinone, N-CH₂C≡CCH₃

106. 4-chlorophenyl, tetrafluoro-pyridazinone, N-CH₂C≡CCH₂CH₃

107. 4-tert-butylphenyl-CH=CH-pyridazinone, N-CH₂C≡CCH₃

132. 3-pyridyl-pyridazinone, N-CH₂C≡CCH₃

133. 4-pyridyl-pyridazinone, N-CH₂C≡CCH₃

134. 1-naphthyl-pyridazinone, N-CH₂C≡CCH₃

135. 2-naphthyl-pyridazinone, N-CH₂C≡CCH₃

136. 2-naphthyl-pyridazinone, N-CH₂C≡CCH₂CH₃

137. 6,7-dimethoxy-2-naphthyl-pyridazinone, N-CH₂C≡CCH₃

138. dimethoxynaphthyl-pyridazinone, N-CH₂C≡CCH₃

TABLE III-continued
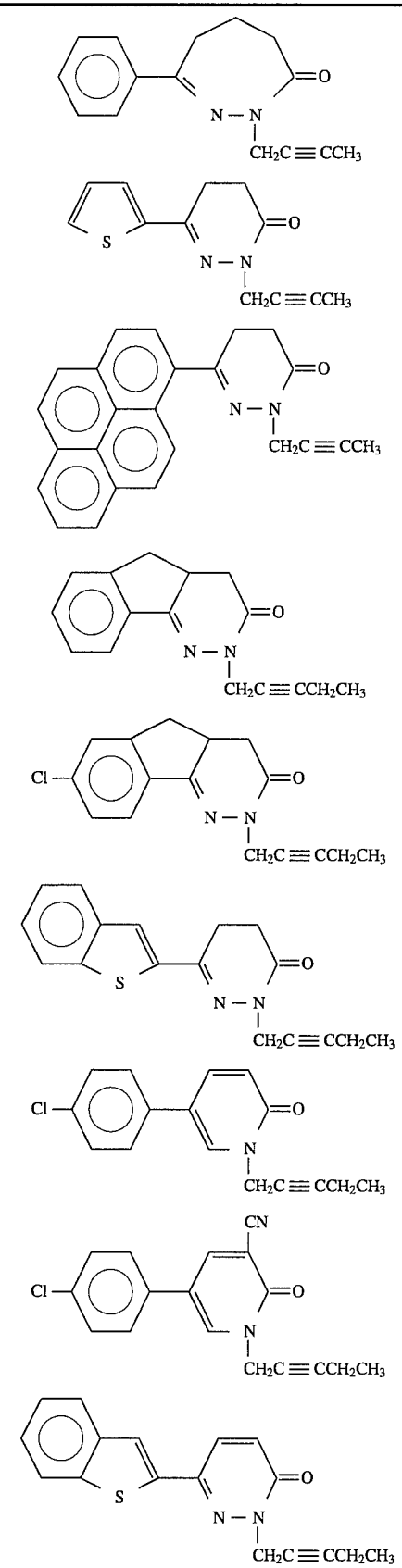

TABLE III-continued
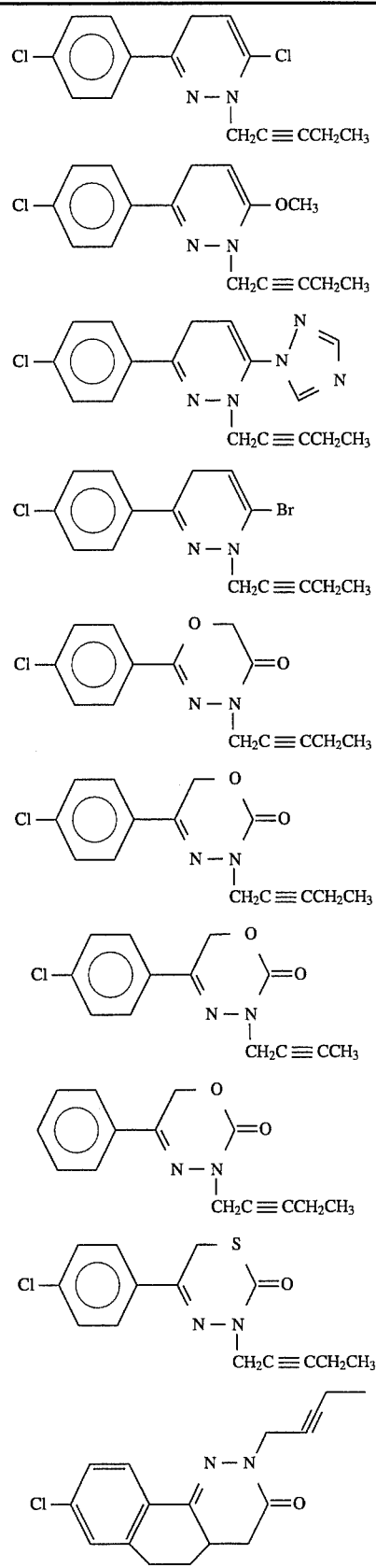
157.
158.
159.
160.
161.
162.
163.
164.
165.
200.
TABLE III-continued
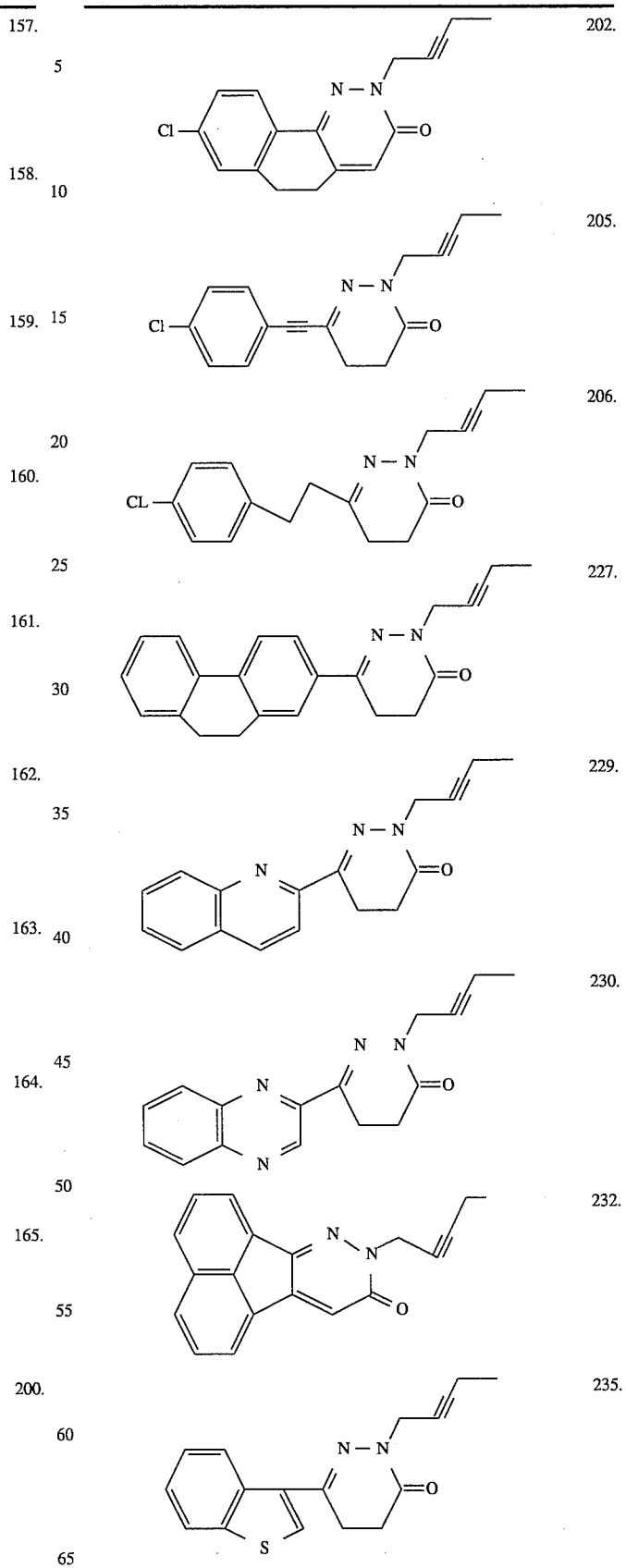
202.
205.
206.
227.
229.
230.
232.
235.

TABLE III-continued
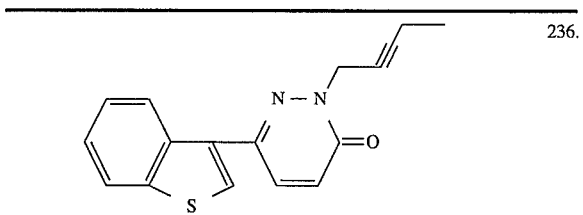
236.
TABLE IV
ELEMENTAL ANALYSES
| Cmpd No. | Calculated | | | Found | | |
|---|---|---|---|---|---|---|
| | % C | % H | % N | % C | % H | % N |
| 6. | 63.39 | 4.49 | 11.35 | 66.22 | 5.66 | 8.92 |
| 7. | 63.51 | 6.47 | 10.58 | 63.84 | 6.88 | 8.92 |
| 8. | 64.00 | 5.75 | 10.66 | 64.05 | 5.77 | 10.46 |
| 10. | 68.35 | 5.06 | 9.37 | 68.60 | 5.21 | 9.09 |
| 11. | 70.29 | 6.29 | 10.92 | 70.21 | 6.55 | 9.97 |
| 12. | 65.57 | 5.50 | 10.19 | 65.34 | 5.63 | 9.43 |
| 13. | 68.87 | 5.41 | 11.50 | 68.63 | 5.29 | 11.24 |
| 14. | 67.49 | 4.57 | 9.84 | 67.66 | 4.53 | 9.68 |
| 15. | 62.11 | 8.50 | 10.35 | 63.70 | 6.50 | 10.02 |
| 16. | 65.28 | 4.18 | 8.96 | 68.83 | 4.17 | 9.30 |
| 17. | 70.69 | 4.68 | 8.68 | 68.42 | 4.70 | 7.53 |
| 18. | 74.97 | 6.71 | 11.65 | 74.64 | 6.79 | 11.31 |
| 19. | 56.96 | 4.10 | 9.49 | 56.97 | 4.60 | 8.70 |
| 20. | 65.68 | 5.51 | 10.11 | 64.69 | 5.52 | 10.06 |
| 21. | 65.57 | 5.50 | 10.20 | 65.29 | 5.30 | 10.36 |
| 22. | 65.57 | 5.50 | 10.20 | 65.25 | 5.22 | 10.16 |
| 23. | 56.95 | 4.07 | 9.45 | 57.19 | 4.18 | 9.16 |
| 24. | 77.92 | 7.79 | 9.09 | 75.12 | 7.67 | 8.85 |
| 25. | 64.00 | 5.75 | 10.66 | 63.75 | 5.67 | 10.96 |
| 26. | 65.57 | 5.50 | 10.20 | 63.70 | 5.47 | 9.68 |
| 27. | 65.57 | 5.50 | 10.20 | 63.37 | 5.32 | 9.96 |
| 28. | 58.27 | 4.56 | 9.06 | 58.58 | 4.55 | 8.82 |
| 29. | 66.51 | 5.96 | 9.71 | 67.73 | 6.57 | 8.77 |
| 31. | 55.00 | 4.26 | 9.18 | 57.92 | 5.39 | 8.05 |
| 32. | 65.10 | 5.79 | 10.13 | 64.07 | 6.13 | 9.70 |
| 33. | 75.45 | 5.69 | 8.80 | 74.64 | 5.59 | 8.77 |
| 34. | 66.54 | 5.93 | 9.70 | 66.36 | 5.89 | 9.59 |
| 35. | 58.19 | 4.07 | 16.96 | 58.05 | 4.15 | 16.68 |
| 36. | 59.11 | 4.30 | 9.19 | 58.88 | 4.16 | 8.80 |
| 37. | 64.50 | 5.02 | 10.74 | 64.06 | 4.93 | 10.60 |
| 38. | 56.50 | 4.14 | 9.52 | 56.73 | 4.06 | 9.34 |
| 39. | 54.99 | 3.93 | 9.17 | 55.70 | 3.90 | 14.03 |
| 40. | 56.34 | 4.38 | 8.76 | 56.70 | 4.38 | 13.85 |
| 41. | 62.34 | 4.87 | 9.09 | 62.35 | 4.84 | 9.06 |
| 42. | 61.22 | 4.42 | 9.52 | 60.48 | 4.40 | 9.55 |
| 43. | 53.71 | 4.20 | 7.83 | 52.45 | 4.11 | 7.56 |
| 44. | 59.44 | 4.95 | 8.67 | 57.67 | 4.82 | 7.94 |
| 45. | 67.01 | 5.27 | 9.76 | 67.32 | 5.37 | 8.94 |
| 46. | 67.43 | 6.32 | 9.25 | 67.26 | 6.52 | 9.19 |
| 47. | 61.96 | 5.20 | 9.63 | 61.93 | 5.56 | 8.67 |
| 48. | 63.05 | 5.62 | 9.19 | 59.33 | 5.40 | 8.33 |
| 49. | 64.45 | 5.41 | 8.84 | 59.73 | 5.27 | 7.73 |
| 52. | 63.81 | 3.71 | 11.44 | 60.31 | 4.04 | 10.66 |
| 54. | 57.84 | 3.81 | 9.63 | 56.10 | 3.90 | 8.42 |
| 56. | 66.06 | 4.80 | 10.27 | 64.52 | 4.79 | 10.15 |
| 57. | 77.03 | 8.11 | 9.46 | 76.30 | 8.12 | 9.59 |
| 58. | 75.59 | 7.09 | 11.02 | 70.90 | 6.86 | 10.60 |
| 59. | 76.12 | 7.46 | 10.45 | 75.89 | 8.07 | 8.78 |
| 60. | 41.88 | 2.68 | 7.52 | 32.86 | 2.39 | 6.25 |
| 61. | 67.13 | 6.29 | 9.79 | 66.96 | 6.39 | 9.51 |
| 63. | 65.57 | 5.46 | 10.20 | 67.67 | 6.35 | 9.11 |
| 64. | 72.45 | 5.66 | 15.85 | 72.68 | 5.92 | 15.55 |
| 65. | 71.83 | 7.04 | 9.86 | 64.59 | 6.20 | 12.98 |
| 66. | 71.83 | 7.04 | 9.86 | 71.56 | 7.01 | 9.81 |
| 67. | 62.09 | 3.98 | 8.52 | 61.21 | 3.95 | 8.47 |
| 68. | 63.81 | 3.95 | 7.84 | 63.70 | 3.88 | 7.55 |
| 69. | 47.66 | 3.69 | 8.55 | 48.89 | 3.89 | 8.33 |
| 70. | 68.67 | 6.08 | 8.89 | 63.30 | 5.56 | 8.03 |
| 71. | 49.51 | 3.56 | 8.24 | 48.20 | 3.35 | 7.50 |
TABLE IV-continued
ELEMENTAL ANALYSES
| Cmpd No. | Calculated | | | Found | | |
|---|---|---|---|---|---|---|
| | % C | % H | % N | % C | % H | % N |
| 72. | 56.96 | 4.10 | 9.49 | 54.00 | 3.89 | 8.53 |
| 73. | 61.54 | 4.79 | 9.57 | 63.47 | 5.59 | 8.54 |
| 75. | 39.99 | 3.11 | 6.66 | 40.18 | 2.91 | 6.74 |
| 76. | 60.33 | 4.34 | 10.00 | 59.18 | 4.13 | 9.61 |
| 77. | 62.39 | 4.53 | 9.70 | 61.43 | 4.26 | 9.36 |
| 78. | 55.14 | 3.08 | 8.57 | 53.96 | 2.90 | 8.35 |
| 80. | 75.56 | 7.13 | 11.02 | 75.18 | 7.68 | 10.58 |
| 81. | 71.09 | 6.71 | 10.37 | 67.47 | 6.31 | 9.64 |
| 82. | 69.75 | 5.85 | 10.85 | 70.53 | 6.22 | 10.09 |
| 84. | 66.06 | 4.80 | 10.27 | 64.48 | 4.69 | 9.76 |
| 85. | 69.65 | 7.30 | 8.12 | 69.77 | 7.26 | 8.04 |
| 86. | 60.26 | 6.00 | 8.78 | 60.15 | 5.95 | 8.70 |
| 87. | 61.98 | 6.07 | 8.03 | 61.81 | 5.78 | 8.19 |
| 88. | 61.21 | 4.03 | 10.19 | 60.73 | 4.06 | 9.70 |
| 89. | 56.67 | 3.74 | 9.44 | 55.02 | 3.77 | 8.80 |
| 91. | 56.44 | 4.80 | 8.78 | 58.76 | 5.39 | 7.55 |
| 94. | 69.34 | 6.43 | 8.51 | 65.38 | 6.08 | 7.96 |
| 95. | 70.00 | 6.76 | 7.81 | 67.27 | 6.56 | 7.80 |
| 96. | 68.23 | 6.68 | 8.84 | 67.96 | 6.48 | 8.63 |
| 100. | 61.97 | 4.16 | 9.63 | 61.19 | 3.99 | 9.48 |
| 106. | 51.96 | 3.19 | 8.08 | 53.49 | 3.43 | 7.63 |
| 107. | 67.01 | 5.27 | 9.76 | 64.76 | 5.20 | 9.27 |
| 108. | 64.99 | 4.26 | 10.83 | 64.72 | 4.17 | 10.68 |
| 109. | 62.83 | 4.54 | 9.77 | 65.73 | 4.82 | 10.21 |
| 110. | 76.79 | 6.77 | 10.53 | 75.75 | 6.92 | 9.50 |
| 111. | 77.55 | 7.48 | 9.52 | 72.95 | 7.68 | 7.66 |
| 112. | 58.63 | 3.91 | 9.12 | 58.44 | 4.04 | 8.97 |
| 113. | 67.02 | 5.24 | 9.77 | 69.13 | 6.38 | 8.21 |
| 114. | 66.06 | 4.77 | 10.28 | 64.29 | 5.04 | 9.92 |
| 115. | 67.02 | 5.24 | 9.77 | 66.91 | 5.30 | 9.77 |
| 116. | 66.09 | 4.77 | 10.28 | 65.85 | 4.94 | 9.99 |
| 117. | 72.36 | 6.43 | 9.92 | 66.42 | 5.51 | 6.52 |
| 118. | 63.81 | 3.70 | 11.45 | 63.81 | 3.62 | 11.39 |
| 119. | 66.55 | 4.09 | 10.34 | 64.70 | 3.84 | 10.13 |
| 125. | 67.04 | 3.37 | 10.42 | 63.56 | 3.31 | 9.20 |
| 128. | 62.40 | 3.49 | 7.70 | 62.36 | 3.29 | 9.51 |
| 132. | 68.70 | 5.77 | 18.79 | 68.12 | 5.98 | 17.84 |
| 136. | 78.62 | 6.21 | 9.66 | 78.54 | 6.12 | 9.43 |
| 137. | 71.41 | 5.98 | 8.32 | 70.25 | 5.88 | 8.04 |
| 139. | 74.96 | 6.71 | 11.65 | 72.83 | 6.68 | 10.70 |
| 140. | 62.04 | 5.21 | 12.06 | 61.01 | 5.04 | 12.28 |
| 141. | 82.26 | 5.18 | 7.99 | 77.90 | 5.27 | 7.02 |
| 142. | 76.26 | 6.39 | 11.10 | 74.32 | 6.45 | 11.49 |
| 143. | 67.01 | 5.27 | 9.76 | 64.82 | 4.99 | 9.72 |
| 144. | 69.74 | 5.47 | 9.57 | 68.27 | 5.48 | 8.92 |
| 145. | 70.72 | 5.16 | 5.16 | 69.34 | 5.21 | 4.86 |
| 146. | 68.80 | 4.30 | 9.44 | 64.41 | 4.12 | 9.16 |
| 147. | 45.03 | 2.87 | 6.18 | 55.13 | 3.54 | 7.20 |
| 148. | 69.39 | 4.76 | 9.52 | 64.21 | 4.61 | 8.37 |
| 149. | 66.07 | 4.77 | 10.28 | 67.34 | 5.51 | 5.57 |
| 150. | 68.45 | 4.89 | 5.70 | 66.62 | 4.87 | 5.46 |
| 151. | 71.89 | 5.46 | 7.98 | 70.88 | 4.94 | 7.83 |
| 152. | 62.38 | 4.53 | 9.70 | 61.00 | 4.41 | 9.12 |
| 153. | 61.95 | 5.20 | 9.63 | 60.77 | 5.06 | 9.10 |
| 154. | 70.70 | 4.68 | 8.68 | 70.27 | 4.36 | 8.54 |
| 155. | 67.88 | 5.70 | 9.31 | 68.06 | 5.50 | 8.83 |
| 156. | 67.49 | 4.60 | 9.83 | 68.27 | 4.48 | 9.17 |
TABLE V
NMR DATA
| Ex. No. | Solvent | (200 MHz, delta scale in ppm, Tetramethylsilane (TMS) standard) |
|---|---|---|
| 9. | CDCl$_3$ | 1.9(s, 3H); 2.6(t, 2H); 3.0(t, 2H); 4.6(s, 2H); 7.4(m, 3H); 7.8(m, 2H) |
| 30. | CDCl$_3$ | 0.9(d, 2H); 4.7(s, 2H); 7–8(m, 10H) |
| 50. | CDCl$_3$ | 2.5(t, 2H); 2.65(t, 2H); 2.95(t, 2H); 4.6(s, 2H); 7.4(d, 2H); 7.75(d, 2H) |
| 51. | CDCl$_3$ | 2.5(t, 2H); 2.65(t, 2H); 2.95(t, 2H); |

TABLE V-continued

NMR DATA

| Ex. No. | Solvent | (200 MHz, delta scale in ppm, Tetramethylsilane (TMS) standard) |
|---|---|---|
| | | 3.69(m, 1H); 4.4(m, 1H); 4.6(s, 2H); 7.75(d, 2H) |
| 53. | CDCl₃ | 1.6(dd, 3H); 2.65(t, 2H); 2.95(t, 2H); 4.7(s, 2H); 5.75(m, 1H); 7.4(d, 2H); 7.75(d, 2H) |
| 55. | CDCl₃ | 2.65(t, 2H); 2.95(t, 2H); 3.75(s, 3H); 4.7(s, 2H); 7.4(d, 2H); 7.7(d, 2H) |
| 62. | CDCl₃ | 1.1(t, 3H); 2.2(q, 2H); 2.4(s, 3H); 2.6(t.3H); 2.95(t, 3H); 4.6(s, 2H); 7.4(d, 1H); 7.55(d, 1H); 7.7(s, 1H) |
| 74. | CDCl₃ | 1.1(t, H3); 2.2(q, 2H); 2.5(t, 2H); 2.95(t, 2H); 4.55(s, 2H); 7.3–7.7(m, 3H) |
| 79. | CDCl₃ | 1.1(m, 3H); 2.2(m, 2H); 2.65(t, 2H); 3.05(t, 2H); 4.65(bs, 2H); 7.4–8(m, 9H) |
| 90. | CDCl₃ | 1.1(t, 3H); 2.2(q, 2H); 2.6(t, 2H); 3.0(t, 2H); 4.6(s, 2H); 7.4(d, 2H) |
| 92. | CDCl₃ | 1.1(t, 3H); 2.15(q, 2H); 2.6(t, 2H); 2.95(t, 2H); 4.6(s, 2H); 6.6(t, 1H); 7.3(t, 1H); 7.5(d, 1H); 7.7(d, 1H) |
| 93. | CDCl₃ | 2.0(s, 1H); 2.6(t, 2H); 2.9(t, 2H); 4.6(s, 2H); 7.4(d, 2H); 7.8(d, 2H) |
| 97. | CDCl₃ | 1.1(t, 3H); 2.2(q, 2H); 2.6(t, 2H); 2.95(t, 2H); 4.5(s, 2H); 7.4–7.8(m, 3H) |
| 98. | CDCl₃ | 1.1(t, 3H); 2.2(q, 2H); 2.65(t, 2H), 2.95(s, 2H); 4.5(s, 2H); 6.8–7.3(m, 3H) |
| 99. | CDCl₃ | 1.1(t, 3H); 2.2(q, 2H); 2..5(t, 2H); 2.9(t, 2H); 3.9(s, 3H); 4.6(s, 2H); 7.0(d, 2H); 7.45(d, 2H) |
| 101. | CDCl₃ | 1.8(dd3H); 2.6(t, 2H); 2.9(t, 2H); 4.8(d, 2H); 5.5(m, 1H); 6.1(m, 1H); 7.4(d, 2H); 7.7(d, 2H) |
| 102. | CDCl₃ | 1.9(d, 3H); 2.6(t, 2H); 2.9(t, 2H); 4.8(s, 2H); 5.5(d, 1H); 6.0(m, 1H); 7.4(d, 2H); 7.7(d, 2H) |
| 103. | CDCl₃ | 1.8(d, 3); 2.6(t, 2); 2.9(t, 2); 4.7(s, 2); 5.5(d, 2); 6.2(m, 1); 7.4(d, 2); 7.7(d, 2) |
| 104. | acetone-d₆ | 1.1(t, 3H); 2.1(q, 2H); 2.65(t, 2H); 3.0(t, 2H); 4.5(s, 2H); 7.2–7.8(m, 3H) |
| 105. | CDCl₃ | 2.6(t, 2H); 3.0(t, 2H); 5.0(s, 2H); 7.4(m, 6H); 7.9(d, 2H) |
| 115. | CDCl₃ | 1.0(t, 2H); 1.2(t, 3H); 1.5(t, 3H); 2.2(m, 3H); 3.0(m, 3H); 4.2(q, 3H); 6.0(m, 2H); 7–7.6(m, 4H) |
| 120. | CDCl₃ | 1.1(t, 3H); 2.2(q, 2H); 5.0(s, 2H); 7.05(d, 1H); 7.5(d, 1H); 7.55(s, 1H); 7.6(d, 1H); 7.65(d, 1H) |
| 121. | CDCl₃ | 1.1(t, 3H); 2.2(q, 2H); 4.95(s, 2H); 7.05(d, 1H); 7.5–7.8(m, 5H) |
| 122. | CDCl₃ | 1.2(t, 3H); 2.2(q, 2H); 5.0(s, 2H); 7.5(d, 2H); 7.8(d, 2H) |
| 123. | CDCl₃ | 1.1(t, 3H); 2.2(m, 2H); 4.9(s, 2H); 7.1(s, 1H); 7.4(d, 2H); 7.8(d, 2H) |
| 124. | CDCl₃ | 0.9(t, 9H); 1.0(q, 6H); 1.2(q, 6H); 1.5(q, 6H); 5.0(s, 2H); 7.0(d, 1H); 7.4(d, 2H); 7.7(d, 2H); 7.8(d, 2H) |
| 126. | CDCl₃ | 1.1(t, 3H); 2.2(q, 2H); 5.0(s, 2H); 6.8–7.0(m, 1H); 7.37.5(m, 2H); 7.7(d, 1H) |
| 127. | acetone-d₆ | 1.1(t, 3H); 2.2(q, 2H); 4.9(s, 2H); 7.0(d, 1H), 7.7–7.9(m, 3H); 8.1(d, 1H) |
| 129. | CDCl₃ | 1.1(t, 3H); 2.2(q, 2H); 5.0(s, 2H); 7.0(d, 1H); 7.25(t, 1H); 7.7(dd, 2H); 8.0(d, 1H) |
| 130. | CDCl₃ | 1.6(dd, 3H); 5.1(m, 2H); 5.15(m, 1/2H), 5.4(m, 1/2H), 7.1(d, 1H), 7.5(d, 2H), 7.7(d, 1H), 7.8(d, 2H) |
| 131. | CDCl₃ | 2.65(m, 2H), 4.4(t, 1H); 4.6(t, 1H); 5(m, 2H); 7.0(d, 1H), 7.5(d, 1H), 7.7(d, 1H), 7.8(d, 2H) |
| 133. | CDCl₃ | 1.8(t, 3H); 2.7(t, 2H); 3.15(t, 2H); 4.6(s, 2H); 8.45(d, 2H); 9.3(d, 2H) |
| 134. | CDCl₃ | 1.9(s, 3H); 2.78(t, 2H); 3.18(t, 2H); 4.65(d, 2H); 7–8.3(m, 7H) |
| 135. | CDCl₃ | 1.9(s, 3H); 2.6(t, 2H); 3.25(t, 2H); 4.65(s, 2H); 7.8(m, 7H) |
| 138. | CDCl₃ | 1.8(t, 3H); 2.8(t, 2H); 3.25(t, 2H); 3.9(s, 2H); 3.95(s, 3H); 4.7(s, 2H); 7.1(m, 3H); 7.7(m, 2H) |
| 157. | CDCl₃ | 1.1(1, 3H); 2.2(m, 2H); 3.5(s, 2H); 4.7(s, 2H); 7.3(d, 2H) 7.8(d, 2H); 9.9(s, 1H) |
| 158. | CDCl₃ | 1.1(t, 3H); 2.2(m, 2H); 3.5(s, 2H); 4.1(s, 3H); 4.6(s, 2H); 7.4(d, 2H); 7.8 (d, 2H); 9.8(s, 1H) |
| 159. | CDCl₃ | 1.1(t, 3H); 2.1(m, 2H); 3.5(s, 2H); 4.4(s, 2H); 7.4(d, 2H); 7.8(d, 2H); 8.3(s, 1H); 8.5(s, 1H) |
| 160. | CDCl₃ | 1.1(t, 3H); 2.2(m, 2H); 3.5(s, 2H); 4.7(s, 2H); 7.4(d, 2H); 7.8(d, 2H); 9.8(s, 1H) |
| 161. | CDCl₃ | 1.1(t, 3H); 2.2(q, 2H); 4.5(s, 2H); 4.8(s, 2H); 7.4(d, 2H); 7.8(d, 2H) |
| 162. | CDCl₃ | 1.1(t, 3H); 2.2(q, 2H); 4.5(s, 2H); 5.2(s, 2H); 7.4(d, 2H); 7.6(d, 2H) |
| 163. | CDCl₃ | 1.6(t, 3H); 4.5(s, 2H); 5.2(s, 2H); 7.5(d, 2H); 7.7(d, 2H) |
| 164. | CDCl₃ | 1.1(t, 3H); 2.2(q, 2H); 4.6(s, 2H); 5.2(s, 2H); 7.5(bs, 3H); 7.7(d, 2H) |
| 165. | CDCl₃ | 1.1(t, 3H); 2.2(c, 2H); 3.95(s, 2H); 4.65(s, 2H); 7.45(d, 2H); 7.8(d, 2H) |
| 200. | CDCl₃ | 1.1(t, 3H); 1.6(m, 1H); 2.2(m, 3H); 2.8(m, 3H); 4.6(m, 2H); 7.2(m, 2H); 8.1(d, 1H) |
| 201. | CDCl₃ | 2.6(t, 2H); 2.9(t, 2H); 3.5(s, 3H); 7.4(d, 2H); 7.7(d, 2H) |
| 202. | CDCl₃ | 1.1(t, 3H); 2.2(m, 2H); 2.9(s, 4H); 4.9(s, 2H); 6.8(s, 1H); 7.3(m, 2H); 8.0(d, 1H) |
| 203. | CDCl₃ | 1.1(t, 3H); 2.2(m, 2H); 2.4–3.4(m, 5H); 3.5(s, 3H); 7.4(d, 2H); 7.8(d, 2H) |
| 204. | CDCl₃ | 2.3(s, 3H); 5.4(s, 2H); 5.9(m, 1H); 63(m, 1H); 7.0(d, 1H); 7.4(d, 2H); 7.6(d, 1H); 7.7(d, 2H) |
| 205. | CDCl₃ | 1.1(t, 3H); 2.2(m, 2H); 2.6(t, 2H); 2.8(t, 2H); 4.6(s, 2H); 6.9(dd, 2H); 7.5(dd, 4H) |
| 206. | CDCl₃ | 1.1(t, 3H); 2.2(m, 2H); 2.4(s, 4H); 2.65(t, 2H); 2.9(t, 2H); 4.5(s, 2H); 7.2(d, 2H); 7.3(d, 2H) |
| 207. | CDCl₃ | 1.1(t, 3H); 2.2(m, 2H); 2.6(t, 2H); 2.9(t, 2H); 4.6(s, 2H); 6.0(s, 2H); 6.9(d, 1H); 7.3(dd, 1H); 7.5(d, 1H) |
| 208. | CDCl₃ | 1.1(t, 3H); 1.5(d, 1H) 2.2(m, 2H); 2.6(t, 2H); 2.9(t, 2H); 5.7(m, 1H); 7.4(d, 2H); 7.8(d, 2H) |
| 209. | CDCl₃ | 1.1(t, 3H); 2.2(m, 2H); 2.6(t, 2H); 3.0(t, 2H); 4.6(m, 2H); 7.2(m, 2H); 7.4(m, 1H); 7.8(m, 1H) |
| 210. | CDCl₃ | 1.1(t, 3H); 2.2(m, 2H); 2.45(s, 3H); 2.6(t, 2H); 2.9(t, 2H); 4.6(m, 2H); 7.3(m, 4H) |
| 211. | CDCl₃ | 1.1(t, 3H); 2.2(m, 2H); 2.6(t, 2H); 2.9(t, 2H); 4.6(m, 2H); 7.4(m, 4H) |
| 212. | CDCl₃ | 1.1(t, 3H); 2.2(m, 2H); 2.5(t, 2H); 2.9(t, 2H); 3.8(s, 3H); 4.6(m, 2H); 7.0(m, 2H); 7.4(m, 1H); 7.6 (m, 1H) |
| 213. | CDCl₃ | 1.1(t, 3H); 2.2(m, 2H); 2.6(t, 2H); 3.0(t, 2H); 4.6(m, 2H); 7.6(m, 2H); 8.0(m, 2H) |
| 214. | CDCl₃ | 1.1(t, 3H); 2.2(m, 2H); 2.6(t, 2H); 2.9(t, 2H); 4.6(m, 2H); 7.1(m, 1H); 7.4(m, 1H); 7.6(m, 2H) |
| 215. | CDCl₃ | 1.1(t, 3H); 2.2(m, 2H); 2.4(s, 3H); 2.6(t, 2H); 2.9(t, 2H); 4.6(m, 2H); 7.3(m, 2H); 7.6(m, 2H) |
| 216. | CDCl₃ | 1.1(t, 3H); 2.2(m, 2H); 2.6(t, 2H); 3.0(t, 2H); 4.6(m, 2H); 7.4(m, 1H); 7.7(m, 1H); 7.9(s, 2H) |
| 217. | CDCl₃ | 1.1(t, 3H); 2.2(m, 2H); 2.6(t, 2H); 2.9(t, 2H); 4.6(m, 2H); 7.6(t, 1H); 7.7(d, 1H); 8.0(d, 1H); 8.1(s, 1H) |
| 218. | CDCl₃ | 1.1(t, 3H); 2.2(m, 2H); 2.7(t, 2H); 3.0(t, 2H); 4.6(m, 2H); 7.6(t, 1H); 8.3(dd, 2H); 8.7(s, 1H) |
| 219. | CDCl₃ | 1.1(t, 3H); 2.2(m, 2H); 2.6(t, 2H); 2.9(t, 2H); 3.8(s, 3H); 4.6(m, 2H); 6.9(m, 1H); 7.4(m, 3H) |
| 220. | CDCl₃ | 1.1(t, 3H); 2.2(m, 2H); 2.3(s, 3H); 2.6(t, 2H); 2.9(t.2H); 3.9(s, 3H); 4.6(m, 2H); 7.2(s, 2H); 7.4(s, 1H) |
| 221. | CDCl₃ | 1.1(t, 3H); 2.2(m, 2H); 2.6(t, 2H); 2.9(t, 2H); 3.9(s, 3H); 4.6(m, 2H); 6.9(d, 1H); 7.6(dd, 1H); 7.9(s, 1H) |
| 222. | CDCl₃ | 1.1(t, 3H); 2.2(m, 2H); 2.6(t, 2H); 2.9(t, 2H); 4.6(m, 2H); 4.6(m, 2H); 7.2(t, 1H); 7.7(m, 1H); 8.1(dd, 1H) |
| 223. | CDCl₃ | 1.1(t, 3H); 2.2(m, 2H); 2.6(t, 2H); 2.9(t, 2H); 4.0(s, 3H); 4.6(m, 2H); 7.2(d, 1H); 8.0(dd, 1H); 8.3(d, 1H) |
| 224. | CDCl₃ | 1.1(t, 3H); 2.2(m, 2H); 2.6(t, 2H); 2.9(t, 2H); 4.6(m, 2H); 7.2(q, 1H); 7.5(m, 1H); 7.7(m, 1H) |
| 225. | CDCl₃ | 1.1(t, 3H); 2.2(m, 2H); 2.3(s, 3H); 2.6(t, 2H); 2.9(t, 2H); 4.6(m, 2H); 7.2(m, 1H); 7.5(m, 2H) |
| 226. | CDCl₃ | 1.1(t, 3H); 2.2(m, 2H); 2.3(s, 3H); 2.6(t, 2H); |

TABLE V-continued

NMR DATA

| Ex. No. | Solvent | (200 MHz, delta scale in ppm, Tetramethylsilane (TMS) standard) |
|---|---|---|
| | | 2.9(t, 2H); 3.9(s, 3H); 4.6(m, 2H); 6.9(d, 1H); 7.6(m, 2H) |
| 227. | CDCl₃ | 1.1(t, 3H); 2.2(m, 2H); 2.6(t, 2H); 2.8(s, 4H); 2.9(t, 2H); 4.6(m, 2H); 7.3(m, 3H); 7.8(m, 4H) |
| 228. | CDCl₃ | 1.1(t, 3H); 2.2(m, 2H); 5.0(m, 2H); 7.0–7.5(m, 10H) |
| 229. | CDCl₃ | 1.1(t, 3H); 2.2(m, 2H); 2.6(t, 2H); 3.4(t, 2H); 4.7(m, 2H); 7.5–8.4(m, 6H) |
| 230. | CDCl₃ | 1.1(t, 3H); 2.2(m, 2H); 2.7(t, 2H); 3.4(t, 2H); 4.7(m, 2H); 7.8(m, 2H); 8.1(m, 2H); 9.7(s, 1H) |
| 231. | DMSOd6 | 2.2(s, 3H); 2.4(s, 3H); 2.5(t, 2H); 2.9(t, 2H); 4.7(s, 2H); 7.6(d, 2H); 7.8(d, 2H) |
| 232. | CDCl₃ | 1.1(t, 3H); 2.2(m, 2H); 5.0(m, 2H); 7.2(s, 1H); 7.7(m, 2H); 8.0(m, 4H) |
| 233. | DMSOd6 | 2.6(t, 2H); 2.9(t, 2H); 4.2(s, 2H); 4.3(s, 2H); 7.5(d, 2H); 7.8(d, 2H); 9.1(bs, 1H) |
| 234. | CDCl₃ | 1.8(s, 3H); 2.0(s, 3H); 2.2–2.4(m, 2H); 2.6(t, 2H); 3.0(t, 2H); 4.5(bs, 1H); 4.9(q, 2H); 7.3(d, 2H); 7.8(d, 2H) |
| 235. | CDCl₃ | 1.1(t, 3H); 2.2(m, 2H); 2.6(t, 2H); 2.9(t, 2H); 4.7(m, 2H); 7.4(m, 2H); 7.6(s, 1H); 7.9(d, 1H); 9.0(d, 1H) |
| 236. | CDCl₃ | 1.1(t, 3H); 2.2(m, 2H); 5.0(m, 2H); 7.0(d, 1H); 7.4(m, 2H); 7.5(d, 1H); 7.7(s, 1H); 7.9(d, 1H); 8.8(d, 1H) |
| 237. | CDCl₃ | 2.3(s, 3H); 2.5(s, 3H); 2.7(t, 2H); 3.0(t, 2H); 5.4(s, 2H); 6.0(s, 1H); 7.4(d, 2H); 7.7(d, 2H) |
| 238. | DMSOd6 | 2.7(t, 2H); 3.0(t, 2H); 5.0(s, 2H); 7.5(d, 2H); 7.8(d, 2H); 12.4(s, 1H) |
| 239. | CDCl₃ | 1.1(t, 3H); 2.2(m, 2H); 2.7(t, 2H); 3.0(t, 2H); 4.4(m, 2H); 5.0(s.2H); 7.4(d, 2H); 7.8(d, 2H) |
| 240. | DMSOd6 | 2.6(m, 2H); 3.0(m, 2H); 4.6(s, 2H); 7.6(m, 6H); 8.4(s, 1H); 12.2(bs, 1H) |
| 241. | CDCl₃ | 2.7(t, 2H); 3.0(t, 2H); 4.6(s, 2H); 5.0(s, 2H); 7.4(d, 2H); 7.8(d, 2H) |

EXAMPLES

Example 6:
6-(4-chlorophenyl)-2-propargyl-4,5-dihydropyridazinone a. 6-(4-chlorophenyl)-4,5-dihydropyridazinone To a mixture of 10 g of 3-(4-chlorobenzoyl)propionic acid and 100 ml of ethanol, 2.4 g of hydrazine monohydrate was added portionwise with stirring and the reaction was refluxed for 2 hours. Upon cooling a white crystalline solid was formed which was filtered off and dried to yield 9.7 g (99%) of the dihydropyridazinone.

b. 6-(4-chlorophenyl)-2-propargyl-4,5-dihydropyridazinone

A mixture of 0.17 g of sodium hydride (60% in oil) and 50 ml of dry dimethylformamide (DMF) was cooled to 5° C. and 0.8 g of the dihydropyridazinone from part a in 25 ml of dry DMF was added dropwise. The reaction was warmed to room temperature for 30 minutes and then cooled to 5° C. Propargyl chloride (0.31 g) was added dropwise and the reaction was stirred overnight at ambient temperature. The reaction was quenched with 100 ml of water and extracted with ethyl ether (3×100 ml). The organic fractions were combined, washed with water (2×100 ml) and saturated brine (1×100 ml). The ether extract was then dried over anhydrous magnesium sulfate, filtered, and evaporated in vacuo to yield 0.68 g (91%) of compound 6 as a tan solid.

Compounds 7–10, 13, 16, 18, 19, 20, 35, 69, 71, 80, 81, 133, 141, 142 and 154 were prepared following essentially the same procedure as described in Example 6b and using the appropriate starting dihydropyridazinone and substituting for propargyl chloride the appropriate alkyl halide chosen from butyl chloride, crotyl bromide, benzyl bromide, benzoyl chloride, chloromethylcyclopropane, bromoacetonitrile, 2-chloromethylthiophene, bromobutyne, 1,3-dibromo-1-propene, or 1,4-dibromo-2-butyne or a mesylate such as 2-butyn-1-yl-methanesulfonate or 2-pentyn-1-yl-methanesulfonate.

Compound 52 was isolated by chromatography (silica gel, 30:70 ethyl acetate/hexane) from an alkylation with propargyl chloride.

Compound 75 was isolated as an impurity from the preparation of compound 71.

Example 11:
6-(4-methoxyphenyl)-2-(2'-butynyl)-4,5-dihydropyridazinone a. 2-butyn-1-yl-methanesulfonate To a solution of 25 g of 2-butyn-1-ol in 200 ml of anhydrous diethyl ether, 72 g of triethylamine was added in one portion and the reaction mixture was cooled to 0° C. Methanesulfonyl chloride (40.8 g) was added dropwise maintaining the temperature below 5° C. Then the reaction was stirred for 2 hours at 0°–5° C. and the triethylamine salts were filtered off and washed with 100 ml of ether. The ether fractions were combined, washed with water (100 ml), brine (100 ml), dried over magnesium sulfate and evaporated in vacuo to yield 39.6 g of the mesylate as a yellow liquid.

b. 6-(4-methoxyphenyt)-2-(2'-butynyl)-4,5-dihydropyridazinone

The starting 6-(4-methoxyphenyl)-4,5-dihydropyridazinone was prepared following essentially the procedure described in Example 6a and alkylated with the mesylate from 11a following essentially the procedure described in 6b.

Compounds 17, 21, 22, 24, 25, 29, 84, 85, 107, 132 and 137 were prepared following essentially the same procedure, using the appropriate substituted dihydropyridazinone and preparing the appropriate mesylate using the appropriate alcohol chosen from 3-phenyl-2-propyn-1-ol, 3-pentyn-1-ol, 2-hexyn-1-ol, 3-methyl-2-butyn-1-ol, 3-t-butylpropyn-1-ol, 2-penten-4-yne-1-ol, 2-decyn-1-ol, or 2-butyn-1-ol.

Compound 138 was isolated from the reaction mixture during the preparation of Compound 137.

Example 12:
6-(4-chlorophenyl)-2-(2'-pentynyl)-4,5-dihydropyridazinone a. ethyl 3-bis(di-t-butylcarboxy)propionate To a solution of 12.5 g (0.11 mole) of potassium t-butoxide in 120 ml of t-butanol was added 20 g of di-t-butylmalonate dropwise at room temperature. A solid paste was formed that made stirring difficult. After 15 minutes at room temperature 16.7 g of ethyl bromoacetate was added dropwise and the resulting mixture stirred at room temperature overnight. The alcohol was removed in vacuo, the residue was taken up in 150 ml of water and the resulting mixture extracted with ether (3×80 ml). The combined ether layers were dried (magnesium sulfate, (MgSO₄)) and evaporated. The residue was distilled through a short Vigreux column. The fractions boiling at 125°–135° C./1 mm were collected to yield 14.2 g (51%) of the triester as a clear oil.

b. ethyl 3-(4-chlorophenyl)-bis(di-t-butylcarboxy)propionate

Sodium hydride (60% in mineral oil, 240 mg, 5 mmoles) was suspended in dry dimethylformamide (DMF) (20 ml) and cooled to 0° C. To the resulting mixture was added ethyl 3-bis(di-t-butylcarboxy)-propionate (1.51 g, 5 mmoles) dropwise. After 10 minutes at 0° C. 4-chlorobenzoyl chloride (0.88 g, 5 mmoles) was added dropwise and the resulting suspension was stirred at 0° C. during ½ hour. The reaction mixture was poured into saturated aqueous ammonium chloride (100 ml) and extracted with ether (3×80 ml), the combined organic layers were washed with brine (3×100 ml), dried and evaporated to yield ethyl 3-(4-chlorophenyl)-3-bis(di-t-butylcarboxy)propionate.

c. 3-(4-chlorobenzoyl)propionic acid

The compound obtained in part b was dissolved in 50 ml of toluene and 100 mg of p-toluenesulfonic acid was added and the resulting solution was heated 80°–85° C. overnight. After cooling at room temperature, the reaction mixture was extracted with 2% aqueous sodium bicarbonate, dried and evaporated to yield 3-(4-chlorobenzoyl)-propionic acid.

d. 6-(4-chlorophenyl)-4,5-dihydropyridazinone

To a solution of 3-(4-chlorobenzoyl)propionic acid (20 g) in absolute ethanol (200 ml) was added 5 g of hydrazine monohydrate. A thick solid was formed which dissolved after heating. The resulting solution was refluxed for 3 h, cooled and the solid formed filtered and dried to yield 16 g (80%) of 6-(4-chlorophenyl)-4,5-dihydropyridazinone.

e. 6-(4-chlorophenyl)-2-(2'-pentynyl)-4,5-dihydropyridazinone

Method i

To a suspension of sodium hydride (NaH) (210 mg 60% in mineral oil) in dry DMF at 0° C. was added 6-(4-chlorophenyl)-4,5-dihydropyridazinone (1.0 g) in DMF (30 ml) dropwise. The yellow mixture was stirred at 0° C. until gas evolution ceased. To the mixture was added 1-bromopent-2-yne (0.8 g) at 0° C. and kept at that temperature for ½ h. The reaction mixture was poured into saturated aqueous ammonium chloride (100 ml) and extracted with ether (3×100 ml). The combined organic layers were washed with brine (2×50 ml), dried and evaporated. Trituration of the oily residue with hexane yielded the product as a light yellow solid.

Method ii

To a stirred mixture of 1-bromopent-2-yne (1.4 g), 6-(4-chlorophenyl)-4,5-dihydropyridazinone (1.0 g), toluene (150 ml) and tetrabutylammonium hydrogen sulfate (100 mg) was added 50% aqueous NaOH (1.9 g) added dropwise. The reaction mixture was heated with continuous stirring at 50° C. for 4 h. The reaction mixture was cooled to room temperature and the layers separated. The organic layer was washed several times with water, dried and evaporated to yield 1.2 g (91%) of 6-(4-chlorophenyl)-2-(2'-pentynyl)-4,5-dihydropyridazinone as a white solid.

Using the same procedure as described for this example compounds 32, 40, 41, 42, 57–66, 73, 78, 79, 82, 90, 91, 96–99, 103, 104, 144, 147 and 148 were made starting from the appropriate benzoyl chloride and alkylating with the appropriate alkyl halide or mesylate.

Example 15:
6-(4-chlorophenyl)-4,5-dihydro-2-t-butylpyridazinone

To a solution of 4-chlorobenzoylpropionic acid (4.24 g) in n-butanol (150 ml) was added anhydrous sodium acetate (1.54 g) and t-butylhydrazine hydrochloride (2.75 g) portionwise at room temperature. The resulting mixture was refluxed for 9 hours distilling off 65 ml of n-butanol during that time. The resulting mixture was cooled and poured into water (500 ml) and extracted with methylene chloride (3×150 ml). The combined organic layers were washed with 2% aqueous sodium hydroxide (3×100 ml), water (2×100 ml), 2% aqueous hydrochloric acid (3×100 ml), and water (1×100 ml), dried and evaporated under vacuum yielding 1.71 g of the expected product.

Compound 14 was prepared using essentially the same procedure and using phenylhydrazine hydrochloride in place of t-butylhydrazine hydrochloride.

Example 26:
6-(4-chlorophenyl)-5-methyl-2-(2'-butynyl)-4,5-dihydropyridazinone a. 2-methyl-3-(4-chlorobenzoyl)propionic acid To a mixture of 11.4 g of methyl succinic anhydride and 38.7 g of chlorobenzene, 30 g of aluminum chloride was added below 35° C. Then the reaction mixture was warmed to 60°–70° C. for 2 hours, cooled and cautiously poured onto 500 g of ice. The mixture was extracted with ether (4×100 ml). The organic layers were combined, washed with water (2×100 ml) and brine (2×100 ml), then dried over magnesium sulfate and evaporated in vacuo to yield a viscous oil which crystallized on standing. The solid was filtered off to yield 12.1 g of 1-methyl-3-(4-chlorobenzoyl)propionic acid. The remainder of the noncrystalline material was identified as 2-methyl-3-(4-chlorobenzoyl)propionic acid.

b. 6-(4-chlorophenyl)-5-methyl-2-(2'-butynyl)-4,5-dihydropyridazinone

The 1-methyl-3-(4-chlorobenzoyl)propionic acid from part a was reacted essentially as described in Example 6 to yield Compound 26.

Compound 27 was prepared following essentially the same procedure and using the 2-methyl-3-(4-chlorobenzoyl)propionic acid from part a above.

Compound 106 was prepared following essentially the same procedure and using perfluorosuccinic anhydride in place of methyl succinic anhydride in part a.

Example 28:
6-(3,4-dichlorophenyl)-2-(2'-pentynyl)-4,5-dihydropyridazinone a. 3,4-dichlorobenzoylpropionic acid To a mixture of 1,2-dichlorobenzene (29.4 g) and succinic anhydride (10 g) was added anhydrous aluminum chloride (28.0 g) portionwise with stirring at room temperature. The resulting mixture was heated at 80° C. for 6 hours, cooled to room temperature and poured into ice-water (600 g). The aqueous suspension was extracted with ethyl ether (4×150 ml), the combined organic layers were washed with water (2×150 ml), dried and evaporated. The oily-solid residue was triturated with hexane-ether (8:2) yielding the product as a yellow solid.

b. 6-(3,4-dichlorophenyl)-2-(2'-pentynyl)-4,5-dihydropyridazinone

The 3,4-dichlorobenzoylpropionic acid was converted to the desired product using essentially the same procedures as described in Example 12d,e.

Compounds 23, 135 and 136 were made from the appropriate starting materials using essentially the same procedure.

Example 30: 6-(4-chlorophenyl-2-(2'-pentynyl)-4-phenyl-4,5-dihydropyridazinone To a mixture of the 3-(4-chlorobenzoyl)-2-phenylpropionitrile (0.037 moles) in 100 ml absolute ethanol there was cautiously added 10 ml of conc $H_2SO_4$ and the mixture was refluxed overnight. The ethanol was removed in vacuo and the residue was dissolved in 200 ml ethyl ether. The ether solution was washed with $H_2O$ (2×100 ml) and brine (100 ml), then dried over anhydrous $MgSO_4$ and stripped to yield 9.2 gms (79%) of a yellow oil. The keto ester was reacted as described in Example 11b-e(i) to obtain the desired compound.

Example 33: 6-(4-phenoxyphenyl)-2-(2'-pentynyl)-4,5-dihydropyridazinone a. 1-bromo-2-butyne The mesylate of 2-butyn-1-ol was prepared as described in Example 11a. To a solution of 27 g of the mesylate in 200 ml of dry tetrahydrofuran was added 70 g of anhydrous lithium bromide portionwise at room temperature. The mixture was stirred overnight at room temperature, then poured into 250 ml of dry ether and washed with water (2×100 ml) and brine (2×100 ml). The ether extract was dried over anhydrous magnesium sulfate and stripped to yield 21 g of 1-bromo-2-butyne as a yellow liquid.

b. 6-(4-phenoxyphenyl)-2-(2'-pentynyl)-4,5-dihydropyridazinone

The phenoxydihydropyridazinone was prepared from the corresponding ketoacid and alkylated as described in example 6 to yield 0.7 g of compound 33 as a tan solid.

Example 34: 6-(4-chlorophenyl)-2-(3'-methyl-2'-butynyl)-4,5-dihydropyridazinone a. 3-methyl-2-butyn-1-ol A solution of 3-methyl-1-butyne in 200 ml of dry THF was cooled to −78° C. and n-butyl lithium (0.160 mole) was added dropwise below 60° C. After stirring for 1 hour at −78° C., gaseous formaldehyde was introduced into the reaction by heating paraformaldehyde (7 g) to a melt and applying a positive pressure to the system to create a formaldehyde atmosphere. The reaction mixture was stirred for 1 hour and then allowed to warm to room temperature and quenched with 100 ml saturated ammonium chloride solution and extracted with ether (3×100 ml). The organic layers were combined, washed with brine (3×100 ml), dried over magnesium sulfate and evaporated in vacuo to yield 3-methyl-2-butyn-1-ol in 60% yield.

b. 6-(4-chlorophenyl)-2-(3'-methyl-2'-butynyl)-4,5-dihydropyridazinone

The alcohol was mesylated using essentially the procedure described in Example 11a and alkylated using essentially the procedure described in Example 6b to yield 1.1 g of Compound 34.

Compounds 45 and 46 were prepared following essentially the same procedure using isopropyl acetylene or 3,3-dimethyl-1-butyne in place of 2-methyl-1-butyne in part a.

Compound 50 was prepared following essentially the same procedure and preparing 1-chloro-5-hydroxy-2-pentyne from propargyl chloride and ethylene oxide.

Example 36: 6-(4-chlorophenyl)-2-(2'-thienylmethyl)-4,5-dihydropyridazinone a. 2-chloromethylthiophene A solution of 10 g of 2-thiophenemethanol, 9.3 g of triethylamine and 250 ml of ether was cooled to 5° C. and 11 g of thionyl chloride was added dropwise. The reaction mixture was stirred at 5°–10° C. for 30 minutes and then warmed to room temperature. The precipitated solid was filtered off and the ether solution was washed with 100 ml of 0.1M hydrochloric acid and then 100 ml of brine. The ether extract was dried over magnesium sulfate and evaporated in vacuo to yield the desired chloride in 75% yield.

b. 6-(4-chlorophenyl)-2-(2'-thienylmethyl)-4,5-dihydropyridazinone

Following essentially the procedure describe in Example 6b, the chloride was used to alkylate 6-4-chlorophenyl)-4,5-dihydropyridazinone to yield compound 36.

Example 37: 6-(3-chlorophenyl)-2-(2'-butynyl)-4,5-dihydropyridazinone a. 3-(3-chlorobenzoyl)propionic acid Sodium (11 g, spheres) was added to 200 ml ethanol with stirring. When the gas evolution ceased, methyl 3-chlorobenzoate (10 g, 0.057 mole) and dimethyl succinate (9.0 g, 0.615 mole) were added rapidly and the mixture was stirred for 5 minutes at room temperature. The mixture was slowly concentrated on a rotary evaporator to yield a greenish paste which was slurried in 100 ml ether and an additional 2 ml of dimethyl succinate was added. The reaction was evaporated to a paste, quenched with water and extracted with ether. The ether extracts were washed with water and brine, dried and evaporated in vacuo.

The starting material was distilled from the residue and the remaining material was refluxed in 6N hydrochloric acid for 2 days to yield 1.6 g of the desired ketoacid which was filtered off.

b. 6-(3-chlorophenyl)-2-(2'-butynyl)-4,5-dihydropyridazinone

The ketoacid from part a was reacted essentially as described in Example 6a and b to yield 0.75 g of compound 37 as a tan solid.

Compounds 38 and 140 were prepared using essentially the same procedure using ethyl 3,5-dichlorobenzoate or ethyl 2-thiophene-carboxylate in place of methyl 3-chlorobenzoate.

Example 39: 6-(4-chloro-3-nitrophenyl)-2-(2'-pentynyl)-4,5-dihydropyridazinone a. 4-chloro-3-nitrobenzoylpropionic acid To fuming nitric acid (150 ml) was added p-chlorobenzoylpropionic acid (20.0 g), slowly portionwise at 0° C. After the addition was completed the resulting mixture was stirred at 0° C. for 30 minutes and the resulting white solid was suction filtered and washed with water until the pH of the washing liquids was neutral, then dried to yield 3-(4-chloro-3-nitrobenzoyl)propionic acid as a white solid (13.0 g).

b. 6-(4-chloro-3-nitrophenyl)-2-(2'-pentynyl)-4,5-dihydropyridazinone

The 4-chloro-3-nitrobenzoylpropionic acid from step a was converted to the final product using essentially the procedure of Example 6a–b.

Example 44:
6-(3,5-dichloro-4-methylphenyl-2-(2'-pentynyl)-4,5-dihydropyridazinone a. 3-(3,5-dichloro-4-methylbenzoyl)propionic acid To a mixture of 3-(4-methylbenzoyl)propionic acid (7.5 g) and methylene chloride (250 ml) was added slowly portionwise aluminum chloride (15 g) at 0° C. After the addition was completed chlorine gas was bubbled in slowly at 0° C. After 6 hours the reaction mixture was poured into a mixture of hydrochloric acid and ice and extracted with methylene chloride (3×150 ml), the combined organic layers were washed with water, dried and evaporated under vacuum yielding 3-(3,5-dichloro-4-methylbenzoyl)propionic acid as a yellow solid (4.5 g).

b. 6-(3,5-dichlorophenyl-4-methylphenyl-2-(2'-pentynyl)-4,5-dihydropyridazinone

The 3-(3,5-dichloro-4-methylbenzoyl)propionic acid from step a was converted to the final product using essentially the procedures of Example 6a–b.

Compound 43 was prepared following essentially the same procedure.

Example 47:
6-(4-chlorophenyl)-2-(4'hydroxy-2'-pentynyl)-4,5-dihydropyridazinone a. 2-hydroxy-5-iodo-3-pentyne Propargyl chloride was hydroxyethylated with acetaldehyde and n-butyl lithium as described in Example 34a.

A solution of 2-hydroxy-5-chloro-3-pentyne (2.0 g) and anhydrous sodium iodide (12.6 g) in 100 ml of dry acetone was stirred overnight at room temperature. The acetone was evaporated in vacuo and the residue was extracted with ether (2×100 ml). The ether extracts were washed with water (2×100 ml) and brine (100 ml), dried and evaporated in vacuo to yield the iodide as a red liquid.

b. 6-(4-chlorophenyl)-2-(4'hydroxy-2'-pentynyl)-4,5-dihydropyridazinone

The iodide was used essentially as described in Example 6b, except that 2 equivalents of sodium hydride were used and the reaction mixture was acidified to pH 5 before extraction to obtain the desired product.

Example 48:
6-(4-chlorophenyl)-2-(4'methoxy-2'-pentynyl)-4,5-dihydropyridazinone To a solution of 100 milligrams of compound 47 and 20 ml of dry methanol, 4 ml of thionyl chloride was added dropwise over 25 minutes. Upon completion of the addition, the methanol solution was evaporated to dryness and the residue was dissolved in 100 ml of ether, washed with 100 ml of water, 100 ml of brine, dried over magnesium sulfate and evaporated in vacuo to yield 100 milligrams of compound 48 as a yellow oil.

Compound 55 was prepared from compound 54 following essentially the same procedure.

Example 49:
6-(4-chlorophenyl)-2-(4'acetoxy-2'-pentynyl)-4,5-dihydropyridazinone To a solution of 100 milligrams of compound 47 in 50 ml of methylene chloride there was added 54 miligrams of pyridine and 69 milligrams of acetic anhydride. The reaction mixture was stirred overnight and evaporated to dryness. The residue was dissolved in 200 ml of ether, washed with 100 ml of water, 100 ml of brine, dried over magnesium sulfate and evaporated to yield 100 milligrams of compound 49 as a colorless oil.

Example 51:
6-(4-chlorophenyl)-2-(5'-fluoro-2'-pentynyl)-4,5-dihydropyridazinone A solution of 120 milligrams of compound 50 and 50 ml of methylene chloride was cooled to 0° C. and a solution of 130 mg of diethylaminosulfurtrifluoride (DAST) in 15 ml of methylene chloride was added dropwise. The reaction mixture was stirred at 0°–5° C. for 1 hour and overnight at room temperature, then quenched with 100 ml of brine and extracted with methylene chloride (2×100 ml). The combined organic extracts were washed with brine (100 ml) and evaporated to yield a yellowish oil which was chromatographed on 50 g of silica (50/50 ethyl acetate/hexane) to yield 60 milligrams of compound 51.

Following essentially the same procedure, compounds 53 and 89 were prepared starting from compounds 47 and 88.

Example 54:
6-(4-chlorophenyl)-2-(3-carboxy-2'-propynyl)-4,5-dihydropyridazinone a. 3-carboxypropargyl chloride A solution of 10 g of propargyl chloride in 200 ml of dry ether was cooled to −70° C. and 100 ml of methyllithium (1.4 molar solution in hexane) was added dropwise in 30 minutes. The reaction mixture was stirred under a carbon dioxide atmosphere for 45 minutes at −60° C., then slowly warmed to room temperature, quenched with 100 ml of brine, acidified to pH 5 and extracted with ether (3×100 ml). The ether layers were combined, washed with 100 ml of water, 100 ml of brine, dried over magnesium sulfate and evaporated to yield a dark brown liquid which was fractionally distilled (0.4 mm Hg, 187°–190° C.) to yield 2.6 g of the acid.

b. 6-(4-chlorophenyl)-2-(3'-carboxy-2'-propynyl)-4,5-dihydropyridazinone

The acid from part a was used following essentially the procedure described for compound 47 to obtain compound 54 as a tan solid.

Example 56:
6-(4-chlorophenyl)-2-(3'-vinyl-2'-propynyl)-4,5-dihydropyridazinone A solution of 1.0 g of compound 6, 0.62 g of vinyl iodide and 100 ml of triethylamine was degassed with nitrogen and 50 milligrams each of copper(I)iodide and bis-triphenylphosphine palladium dichloride was added. After stirring overnight at 50° C., the triethylamine was evaporated and the residue was redissolved in 150 ml of ether, passed through 10 g of silica and evaporated to yield 1.0 g of compound 56 as a yellow oil.

Compound 67, 68, 78, 119, were prepared following essentially the same procedure using the appropriate starting material and substituting 2-iodothiophene, 1-chloro-4-iodobenzene or iodofluoroethylene in place of vinyl iodide when appropriate.

Compound 70 was prepared from compound 69 and 3-methylbutyne following essentially the same procedure.

Example 72: 6-(4-chlorophenyl)-2-(4'-chloro-2'-butynyl)-4,5-dihydropyridazinone To a solution of 2.5 g of 6-(4-chlorophenyl)-4,5-dihydropyridazinone in 100 ml of toluene there was added 100 milligrams of tetrabutylammonium hydrogen sulfate and with rapid stirring added 4.7 g of 50% aqueous sodium hydroxide. Then 1,4-dichloro-2-butyne (7.4 g) in 50 ml of toluene was added dropwise and the reaction mixture was heated to 50°–60° C. for 4 hours. The reaction mixture was cooled and poured into 200 ml of water. The organic phase was separated and the aqueous phase was extracted with ether (2×100 ml). The combined organic phases were washed with 100 ml of water, 100 ml of brine and dried over magnesium sulfate and evaporated to yield a crude product which was chromatographed to yield 1.9 g of compound 72.

Compound 128 was prepared following essentially the same procedure starting with 6-(4-chloro-3-fluorophenyl) pyridazinone and using powdered potassium hydroxide instead of sodium hydroxide.

Compound 100 was prepared following essentially the same procedure and using the mesylate prepared from 1-bromo-2-pentyn-4-ene described in example 33.

Example 74: 6-(4-chloro-3-fluorophenyl)-2-(2'-pentynyl)-4,5-dihydropyridazinone Method A a. 4-chloro-3-fluorobenzoic acid Method i 0.7 Gram-atom (17.0 g) of magnesium turnings was covered with 100 ml of dry ethyl ether and 0.05 mole (0.95 g) of 1,2-dibromoethane was added down the side of the flask in such a way that it did not mix with the ether but contacted the magnesium. The mixture was allowed to stand without stirring until bubbles formed around the turnings and the ether became cloudy. Then the mixture was stirred and warmed to mild reflux and 0.62 mole (130.0 g) of 4-chloro-3-fluorobromobenzene in 500 ml of dry ether was added to the flask at such a rate that there was a mild reflux. The refluxing and stirring were continued for 30 minutes after the addition of the halide was completed.

The reaction mixture was then cooled to −10° C. and dry $CO_2$ was bubbled in below −2° C. The reaction was complete when the temperature fell below −10° C. and did not rise when increasing the rate of flow of $CO_2$. To the cold mixture was added 150 ml of 25% HCl at 0° C. The layers were separated and the aqueous layer was washed with ether (3×150 ml). The combined organic layers were washed with water (2×200 ml), dried and evaporated to yield the product as a white solid. 98 g (91% yield).

Method ii

A mixture of 110 g of 98% $H_2SO_4$ and 192 g (0.97 mole) of 4-chloro-3-fluorobenzotrifluoride was stirred and then heated cautiously until the hydrogen fluoride evolution started (approx. 130° C.). The reaction mixture was heated at 130°–135° C. for 17 hours, and poured into 1 Kg of ice. The resulting white precipitate was filtered off and washed with water until the pH of the washing liquids was neutral, and the precipitate was dried to yield 165 g (98%) of the expected acid as a white solid.

b. 6-(4-chloro-3-fluorophenyl)-2-(2'-pentynyl)-4,5-dihydropyridazinone

The 4-chloro-3-fluorobenzoic acid was then converted to the corresponding acid chloride by standard means. The desired product was produced following essentially the procedures of Example 11b–e.

Method B a. 4-chloro-3-fluorobenzoylpropionic acid

To a solution of succinic anhydride (6.0 g) in tetrahydrofuran (60 ml) was added dropwise the Grignard prepared from 1.5 g (0.062 mole) of magnesium turnings and 10.5 g (0.05 mole) of 1-bromo-4-chloro-3-fluorobenzene using the procedure of part a. When the addition was completed, the resulting suspension was stirred for 2 hours at 45° C. after which water (100 ml) was added slowly and the resulting mixture was acidified with concentrated hydrochloric acid to pH=1. The ether layer was separated and extracted with 5% aqueous sodium hydroxide (3×100 ml). The combined aqueous solutions were washed with ether (1×100 ml). The combined basic aqueous layers were acidified with concentrated hydrochloric acid to pH 1 and extracted with ethyl acetate (3×150 ml). The combined organic extracts were washed with water (1×150 ml) and brine (1×150 ml), dried over anhydrous magnesium sulfate and evaporated in vacuo to give 7.1 g (62%) of the product as a yellow orange solid.

The resulting acid was converted to the desired product using the procedure of Example 11d–e.

Compound 83 was prepared following essentially the same procedure.

Example 76: 6-(4-chlorophenyl)-2-(4'-fluoro-2'-butynyl)-4,5-dihydropyridazinone a. 4-tetrahydropyranoxy-2-butyn-1-ol To a mixture of 5.0 g of 2-butyne-1,4-diol and 10 milligrams of p-toluenesulfonic acid and 150 ml of dry ether there was added dropwise with stirring at room temperature 4.9 g of 3,4-dihydro-2H-pyran. After stirring overnight at ambient temperature the ether was evaporated and the residue was poured into 200 ml of water. The aqueous solution was extracted with hexane (2×100 ml) and then re-extracted with ether (3×100 ml). The combined ether extracts were washed with 100 ml of brine, dried over magnesium sulfate and evaporated to yield 6.8 g of 4-tetrahydropyranoxy-2-butyn-1-ol.

b. 6-(4-chlorophenyl)-2-(4'-hydroxy-2'-butynyl)-4,5-dihydropyridazinone

The alcohol was converted to the mesylate using essentially the procedure described in Example 11a and the mesylate was used in the alkylation following essentially the procedure describe in Example 6b. The resulting compound was dissolved in 100 ml of methanol. Amberlite IR20® (2 g) resin was washed with 10 ml of methanol and added to the reaction mixture. After stirring for 1 hour, the resin was filtered off and the methanol was evaporated. The oily residue was triturated with hexane to yield 1.3 g of the desired alcohol as a tan solid.

c. 6-(4-chlorophenyl)-2-(4'-fluoro-2'-butynyl)-4,5-dihydropyridazinone

The alcohol from part b was treated with DAST following essentially the procedure described in Example 51. Silica gel chromatography (50:50 hexane/ethyl acetate) of the crude product yielded 300 milligrams of compound 76 as a pale yellow solid.

Example 77: 6-(4-chlorophenyl)-2-epoxymethyl-4,5-dihydropyridazinone

To a mixture of 1.0 g of compound 56 and 50 ml of methylene chloride, 1.3 g of m-chloroperbenzoic acid was added portionwise at room temperature. The reaction mixture was stirred overnight at ambient temperature then poured into 100 ml of methylene chloride and washed with saturated sodium bisulfite (2×100 ml), brine (100 ml), dried over magnesium sulfate and evaporated to yield a residue which was chromatographed on silica (50:50 ethyl acetate/hexane) to yield 350 milligrams of compound 77 as a white solid.

Example 86:
6-(4-chlorophenyl)-2-(4'-trimethylsilyl-2'-butynyl)-4,5-dihydropyridazinone The bromide of trimethylsilyl propargyl alcohol was prepared following essentially the procedures described in Examples 11a and 33a. To a mixture of 300 ml of dry tetrahydrofuran and 4.8 g of sodium hydride (60% in oil) there was added 25 g of 6-(4-chlorophenyl)-4,5-dihydropyridazinone dissolved in 200 ml of tetrahydrofuran. When the hydrogen gas evolution stopped, the solvent was removed in vacuo. The resulting solid was slurried in hexane and filtered off to yield 27.4 g of the sodium salt as a white non-hydroscopic solid.

A solution of 1.0 g of the sodium salt in 50 ml of dimethylformamide was cooled to 5° C. and 0.9 g of 1-bromo-3-trimethylsilyl-2-propyne was added dropwise. After stirring for 30 minutes at 5° C., the reaction mixture was warmed to room temperature, quenched with 100 ml of water and extracted with ether (3×100 ml). The ether extracts were combined, washed with 100 ml of water, 100 ml of brine, dried over magnesium sulfate and evaporated to yield the crude product which was chromatographed on silica gel (30:70 ethyl acetate/hexane) to yield 0.5 g of compound 86 as a white solid.

Compounds 96 and 124 were prepared using essentially the same alkylation procedure and the mesylate of 2-octyn-1-ol or 2,4-pentadiyn-1-ol (example 93).

Compound 105 was prepared following essentially the same procedure to form the sodium salt of 6-(4-chlorophenyl)pyridazinone which was alkylated with 3-chlorobenzyl bromide.

Compound 101 was prepared following essentially the same procedure and using the mesylate of 2-hexyn-4-ene-1-ol prepared following essentially the procedure described in example 56 starting from propargyl alcohol and 1-bromo-1-propene.

Compounds 102 and 103 were obtained from compound 101 by chromatography on an HPLC semiprep silica column eluting with 1:3 ethyl acetate/heptane.

Example 87:
6-(4-chlorophenyl)-2-(4'-aldehydo-2'-butynyl)-4,5-dihydropyridazinone, diethyl acetal a. 4-hydroxy-2-butynylaldehyde diethylacetal To a mixture of magnesium turnings (18.5 g) and 350 ml dry tetrahydrofuran, bromoethane (83 g) was added dropwise below 50° C. After all the magnesium had reacted, a solution of propargyl alcohol (20 g, 0.356 mole) in 100 ml of tetrahydrofuran was added dropwise. The mixture was refluxed for one hour and ethyl orthoformate (53 g, 0.356 mole) in 50 ml tetrahydrofuran was added dropwise, as rapidly as possible. The mixture was refluxed for 8 hours and stirred overnight at room temperature. The mixture was cautiously poured into 500 ml ice cold 20% aqueous ammonium acetate and extracted with 3×100 ml ethyl ether. The ether extract was washed with $H_2O$ (2×100 ml) and 100 ml brine, dried over anhydrous $MgSO_4$ and stripped to yield 42 g of the crude product which was distilled at 115°–120° C. (3 mm Hg) and 31 g pure product (56% yield) was isolated.

b. 6-(4-chlorophenyl)-2-(4-aldehydo-2'-butynyl)-4,5-dihydropyridazinone, diethyl acetal The hydroxy compound was converted to the corresponding mesylate then used to alkylate 6-(4-chlorophenyl)-4,5,-dihydropyridazinone as described in Examples 11a and 6b(i), respectively.

Example 88:
6-(4-chlorophenyl)-2-(4-aldehydo-2'-butynyl)-4,5-dihydropyridazinone A mixture of the diethylacetal (Compound 86) (4.0 g), formic acid (10 ml), and water (20 ml) was heated to 40° C. with stirring for three hours. The mixture was poured into 100 ml $H_2O$ and extracted with 3×100 ml ethyl ether and washed with 100 ml sodium bicarbonate (saturated) and 100 ml brine. The ether extract was dried over anhydrous $MgSO_4$ and stripped to yield 2.2 g of a tan solid characterized to be the aldehyde (80% yield).

Example 93:
6-(4-chlorophenyl)-2-(2',4'-pentadiynyl)-4,5-dihydropyridazinone a. 2,4-pentadiyn-1-ol To a suspension of sodamide (prepared from 20.5 g (0.89 gram atoms) of sodium and 500 ml liquid ammonia) was added dropwise at –40° C. 1,4-dichloro-2-butyne (37 g, 0.3 mole). After stirring at –40° C. for 30 minutes, a suspension of dry paraformaldehyde (9 g) was added portionwise in 100 ml anhydrous diethyl ether ($Et_2O$). After stirring for 1 hour at –40° C., ammonium chloride (40 g, 0.75 moles) was added portionwise as a solid followed by 200 ml of $Et_2O$. The ammonia was allowed to evaporate overnight and the solution was filtered through Celite®. The solids were washed with $Et_2O$ (100 ml) and the ether layer was washed with saturated brine. The ether layer was dried over anhydrous $MgSO_4$ and stripped to yield 16 g of 2,4-pentadiyn-1-ol as a red oil (67% yield).

b. 6-(4-chlorophenyl)-2-(2',4'-pentadiynyl)-4,5-dihydropyridazinone

The alcohol was converted to the mesylate following essentially the procedure described in Example 11 a. The mesylate was used in the alkylation as described in Example 86 to yield the expected product.

Compound 125 was prepared following essentially the same procedure and using the appropriate pyridazinone.

Example 94:
6-(4-chlorophenyl)-2-(3'-cyclohexyl-2'-propenyl)pyridazinone a. 3-cyclohexyl-2-propyn-1-ol To a solution of ethyl magesium bromide (prepared from 2.5 g of magnesium turning and 11.3 g of bromoethane) in ether was added dropwise a solution of 10.2 g of cyclohexylacetylene in ether and the reaction mixture was refluxed for 2 hours. The reaction mixture was cooled to ambient temperature and anhydrous formaldehyde (prepared from the thermal decomposition of 50 g of paraformaldehyde for 20 minutes) was bubbled into the mixture. After cooling, the reaction was quenched with saturated ammonium chloride and extracted with ether (2×100 ml). The combined ether extracts were washed with brine, dried over magnesium sulfate and evaporated to yield the product which was distilled under high vacuum at 68°–74° C. to yield 6.4 g as a colorless liquid.

b. 6-(4-chlorophenyl)-2-(3'-cyclohexyl-2'-propenyl)pyridazinone

Using the alcohol from part a and following essentially the procedures described in Examples 11 and 86, compound 94 was prepared.

Compound 95 was prepared following essentially the same procedure starting with 1-cyclohexyl-2-propyne.

Example 109:
6-(4-chlorophenyl)-2-(2'-pentynyl)pyridazinone a. 6-(4-chlorophenyl)pyridazinone To a solution of 6-(4-chlorophenyl)-4,5-dihydropyridazinone (11.75 g) and glacial acetic acid (100 ml) was added dropwise 3 ml of bromine and the mixture was heated at 60°–70° C. for 3 h. The resulting mixture was cooled and slowly poured into 400 ml of cold water. The resulting white solid was filtered and dried to yield 10.83 g (89%) of 6-(4-chlorophenyl)pyridazinone.

b. 6-(4-chlorophenyl)-2-(2'-pentynyl)pyridazinone

The pyridazinone obtained in part a above was alkylated as described in Example 6 to obtain 6-(4-chlorophenyl)-2-(2'-pentynyl)-pyridazinone.

Compounds 108, 110–118, 120, 121, 127 and 129–131 were prepared following essentially the same procedure starting with the appropriate dihydropyridazinone and alkylating agent.

Example 122: 6-(4-chlorophenyl)-4,5-difluoro-2-(2'-pentynyl)-pyridazinone a. 1,4-dichloro-1,2,2-trifluorocyclobut-3-ene To a solution of 1,1,2 trichloro-2,3,3-trifluorocyclobutane (55.5 g) in 100 ml of anhydrous ether, triethylamine (40 ml) was added dropwise over 30 min at room temperature, and the mixture was stirred overnight at ambient temperature. The mixture was then stirred with 120 ml $H_2O$ and 7.5 ml of concentrated HCl. The ether layer was washed with $H_2O$ (100 ml), brine (100 ml), dried over anhydrous $MgSO_4$, and evaporated in vacuo. The residue was distilled fractionally at atmospheric pressure from 64°–68° C. to yield 36 g (79%) of a colorless liquid as pure product.

b. 2-chloro-2,3,3-trifluorosuccinic acid

To potassium hydroxide (11.3 g) in 250 ml $H_2O$, potassium permanganate (56 g) was added in one portion and the mixture was stirred until everything was in solution. Then 1,4-dichloro-1,2,2-trifluorocylobutene-3-ene (31.1 g) was added dropwise at 15°–20° C. over 30 minutes. The mixture was stirred for 12 hours at room temperature, filtered through Celite® and washed with water. The aqueous solution was acidified with 23 ml concentrated $H_2SO_4$ (4×100 ml). The acid solution was extracted with ether and dried over anhydrous $MgSO_4$. The ether layer was stripped to yield the product as 26 g (71%) of a colorless liquid.

c. 2,2,3-trifluorosuccinic acid

To a stirring solution of the chlorotrifluorosuccinic acid (part b) (24.5 g) in 200 ml dioxane was added portionwise zinc metal (85 g) and the mixture was stirred at ambient temperature for 10 hours to yield a viscous liquid which was decanted from the unreacted zinc. Most of the dioxane was evaporated in vacuo. The residue was dissolved in 100 ml $H_2O$ and a solution of 7.7 ml of concentrated $H_2SO_4$ in 25 ml of water was added. The solution was extracted with ether (3×100 ml) and dried over anhydrous $MgSO_4$. The organic layer was stripped to yield 8.3 g (32%) of the product as a crystalline solid.

d. 2,2,3-trifluorosuccinic anhydride

A slurry of the succinic acid (part c) (8.0 g) and phosphorus pentoxide (14.7 g) was heated and the anhydride was distilled through a 6" Vigreux column at 15 mm Hg. The colorless liquid was collected at 60°–68° C. The product was isolated in 53% yield (3.0 g).

e. 6-(4-chlorophenyl)-4,5-difluoro-2-(2'-pentynyl)-pyridazinone

The anhydride was reacted with chlorobenzene as described in Example 26a to produce a mixture of fluorinated ketoacids. Cyclization with hydrazine yielded a single difluorodihydropyridazinone. Alkylation with 1-bromo-2-pentyne yielded 6-(4-chlorophenyl)- 4,5-difluoro-2-(2'-pentynyl)-pyridazinone.

Example 124:
6-(4-chlorophenyl)-2-(3'-tri-n-butyltin-2'-propynyl)-4,5-dihydropyridazinone A solution of 6.0 g of compound 118 in 50 ml of dry tetrahydrofuran was cooled to −78° C. and 17.4 ml of 1.6M n-butyllithium in hexane was added dropwise. The solution was stirred at −78° C. for 30 minutes and then a solution of 8.0 g of tributyltin chloride in 30 ml of dry tetrahydrofuran was added dropwise. The reaction mixture was allowed to warm to room temperature and stirred overnight, then quenched with 100 ml of brine and extracted with ether (3×100 ml). The ether extracts were combined, washed with 100 ml of water, 100 ml of brine, dried and evaporated to yield a residue which was chromatographed on silica (50:50 ethyl acetate/hexane) to yield 2.1 g of compound 124 as a yellow oil.

Example 134:
6-(1-naphthyl)-2-(2'-pentynyl)-4,5-dihydropyridazinone a. 3-(1-naphthoyl)propionic acid A mixture of naphthalene (40 g) and succinic anhydride (20 g) was added to a well stirred suspension of aluminum trichloride (55 g) in nitrobenzene (140 ml). The resulting mixture was stirred overnight at room temperature. The mixture was then poured slowly onto ice-water (600 g) and acidified with 6N-hydrochloric acid. The crude acid was filtered, washed with water until washings were neutral and recrystallized from ethanol yielding the product (m.p. 170°–172° C.).

b. 6-(1-naphthyl)-2-(2'-pentynyl)-4,5-dihydropyridazinone

The propionic acid from part a was reacted essentially as described in Example 6a–b to obtain the expected product.

Example 139:
2-(2-butynyl)-7-phenyl-1,2-diazapin-3-one a. 7-phenyl-1,2-diazapin-3-one To a mixture of 10 g (0.052 mole) of 4-benzoylbutyric acid in 300 ml of toluene, hydrazine was added in one portion and the reaction was heated to reflux until all water had ceased to azeotrope. The reaction mixture was cooled and the toluene was stripped off in vacuo. The residue was dissolved in 200 ml $Et_2O$ and washed with $H_2O$ (100 ml)

and brine (100 ml). The ether extract was dried over anhydrous MgSO$_4$, filtered and stripped to yield an orange semisolid which was triturated with ether to yield 3.8 g (39%) of the desired product as a yellow solid.

b. 2-(2-butynyl)-7-phenyl-1,2-diazapin-3-one

The product from part a was alkylated essentially as described in Example 6b to yield 1.1 g of the desired product as a yellow oil.

Example 143:
7-chloro-2,4,4a,5-tetrahydro-2-(2-pentyn-1-yl)-indeno[1,2-c]-pyridazin-3-one a. 2-carbomethoxy-5-chloroindanone To a mixture of sodium hydride (2.4 g, 60% in mineral oil, 0.06. mole) and 50 ml dry dimethoxyethane, 5-chloroindanone (50 g, 0.03 mole) in 50 ml dimethoxyethane was added dropwise at room temperature. The mixture was stirred at room temperature until hydrogen evolution ceased. Then dimethylcarbonate (27 g, 0.3 mole) was added dropwise at room temperature and the reaction was heated to 60° C. for one hour. The reaction was cooled to room temperature, quenched with 100 ml H$_2$O, acidified to pH 5 with concentrated HCl and extracted with ethyl ether (3×100 ml). The ether extract was washed with brine (100 ml), dried over anhydrous MgSO$_4$ and stripped to yield 3.0 g (45%) of the desired product as a tan solid.

b. 2-carbomethoxy-2-carbomethoxymethyl-5-chloroindanone

To a mixture of sodium hydride (0.44 g, 60% in mineral oil, 0.0111 mole) and 50 ml dry dimethylformanide (DMF), the indanone ester from part a (2.5 g, 0.0111 mole) in 50 ml DMF was added dropwise with cooling. The reaction mixture was stirred at 10° C. until all H$_2$ evolution ceased. Then methyl bromoacetate (1.9 g, 0.0122 mole) dissolved in 25 ml of DMF was added dropwise at 10° C. The reaction was stirred at 5°–10° C. for one hour and overnight at room temperature, then quenched with H$_2$O (100 ml) and extracted with ether (3×100 ml). The organic layers were combined and washed with H$_2$O (100 ml) and brine (100 ml), then dried over anhydrous MgSO$_4$ and stripped to yield 3.0 g of a tan solid.

c. 7-chloro-2,4,4a,5-tetrahydro-indeno[1,2-c]-pyridazin-3-one

A mixture of the diester (2.5 g, 0.0084 mole) from part c and 100 ml of 6N HCl was refluxed for 2 hours, until no starting material was detected by thin layer chromatography. The reaction mixture was cooled to room temperature and poured into 200 ml of ice/water. A precipitate was formed which was collected by vacuum filtration and washed with 200 ml H$_2$O. The precipitate was dried overnight in vacuo at 40° C. to yield 1.8 g, (95%) white solid.

d. 7-chloro-2,4,4a,5-tetrahydro-2-(2-pentyn-1-yl)-indeno[1,2-c]-pyridazin-3-one

The ketoacid was reacted as described in Example 6a–b to yield Compound 143. Compound 155 was prepared following essentially the same procedure and starting with 5-chloro-3-methylindanone.

Examples 145 and 146:
5-(4-chlorophenyl)-1-(2-pentyn-1-yl)-2-pyridinone and 5-(4-chlorophenyl)-3-cyano-1-(2-pentyn-1-yl)-2-pyridinone a. 2-(4-chlorophenyl)-3-dimethylaminopropenal Phosphorus oxychloride (92 g) was added dropwise to stirred DMF (78 ml) between 10°–15° C. To the resulting slurry was added 4-chlorophenylacetic acid (34.12 g). The resulting mixture was stirred at room temperature for one half hour and then heated to 70°–80° C. during 5.5 hours, during which time the mixture became effervescent. The reaction mixture was cooled and poured slowly onto cracked ice. The resulting suspension was brought to pH 10 with solid potassium carbonate. Ice was added intermittently during this addition to maintain the temperature below 15° C. Toluene (150 ml) was added and the resulting mixture heated at 100° C. for one hour. The mixture was cooled and allowed to stand overnight. The two resulting layers were separated and the aqueous layer extracted with toluene (2×100 ml). The combined organic layers were washed with water (5×200 ml) and dried over anhydrous sodium sulfate. The solvent was evaporated in vacuo and the resulting yellow solid was triturated with hexane to yield 26 g of 2-(4-chlorophenyl)-3-dimethylaminopropenal as a tan solid mp. 120°–125° C.

b. 3-cyano-5-(4-chlorophenyl)-2-pyridinone

To solution of sodium methoxide (7.52 g) in methanol (130 ml) was added cyanoacetamide (5.84 g) followed by 2-(4-chlorophenyl)-3-dimethylaminopropenal and the resulting suspension was refluxed overnight. During this time a yellow solid was formed. The mixture was cooled to room temperature and glacial acetic acid (50 ml) was added followed by water (100 ml). The resulting yellow orange solid was filtered off, washed several times with water and dried to yield 8.1 g of 3-cyano-5-(4-chlorophenyl)-2-pyridinone.

c. 5-(4-chlorophenyl)-2-pyridinone

A mixture of 3-cyano-5-(4-chlorophenyl)-2-pyridinone (4.6 g) and 85% H$_3$PO$_4$ (60 ml) was heated at reflux for 16 hours. The resulting mixture was cooled to room temperature, poured into ice/water and filtered yielding 3.1 g of 5-(4-chlorophenyl)-2-pyridinone as a yellow solid.

d. 5-(4-chlorophenyl)-1-(2-pentyn-1-yl)-2-pyridinone

To a suspension of NaH (60% in mineral oil, 200 mg) in dry DMF (50 ml) at 0° C. was added the preceding pyridinone and the mixture was stirred at 0° C. for one half hour. To the resulting suspension was added 1-bromo-2-pentyne dropwise. The resulting mixture was kept at 0° C. during one half hour and poured into saturated aqueous ammonium chloride (200 ml). The aqueous suspension was extracted with ether (3×100 ml) and the combined ether layers washed with brine and dried, yielding the crude product. After column chromatography (silica gel, hexane:ethyl acetate 8:2) the product was obtained as a white amorphous solid.

e. 5-(4-chlorophenyl)-3-cyano-1-(2-pentyn-1-yl)-2-pyridinone

3-Cyano-5-(4-chlorophenyl)-2-pyridinone was similarly alkylated to yield 5-(4-chlorophenyl)-3-cyano-1-(2-pentyn-1-yl)-2-pyridinone, Compound 146.

Example 149:
5-chloro-1-(2-pentyn-1-yl)-2-quinolinone a. N-(4-chlorophenyl)cinnamamide To a mixture of 4-chloroaniline (16.2 g), toluene (120 ml), and pyridine (11 ml) at 0° C., cinnamoyl chloride (20.0 g) in 120 ml of toluene was added dropwise. After stirring 15 minutes at 0° C. the reaction mixture was poured into a mixture of ethyl acetate: water (250 ml:250 ml). The organic layer was separated and extracted with 5% aqueous HCl (3×250 ml), water (1×250 ml), 5% aqueous sodium bicarbonate (3×250 ml), dried over anhydrous sodium sulfate and evaporated yielding the amide as a white solid.

b. 5-chloro-2-quinolinone

To a mixture of N-(4-chlorophenyl)cinnamamide (8.3 g), and chlorobenzene (60 ml) was added portionwise aluminum chloride (21.4 g) under nitrogen at room temperature and the reaction mixture was slowly warmed up to 125° C. and kept at that temperature for 3 hours. The reaction mixture was cooled down and poured over 400 g of ice. The product crystallized out as a pink solid which was filtered and dried.

c. 5-chloro-1-(2-pentyn-1-yl)-2-quinolinone

To a suspension of NaH (60% in mineral oil, 700 mg) in dry DMF (100 ml) at 0° C. was added the preceding quinolinone (2.05 g) and the mixture was stirred at 0° C. for one half hour. To the resulting suspension was added 1-bromo-2-pentyne (1.6 g) dropwise. The resulting mixture was kept at 0° C. for one half hour and poured into saturated aqueous ammonium chloride (200 ml). The aqueous suspension was extracted with ether (3×100 ml), the combined ether layers washed with brine and dried, yielding the crude product. Trituration with hexane yielded the product as a yellow solid (1 g).

Example 150:
5-(4-chlorophenyl-1-(2-pentyn-1-yl)-2-pyrimidinone a. 5-(4-chlorophenyl)-2-pyrimidinone A mixture of 2-(4-chlorophenyl)dimethylaminopropenal (Example 145a) (5.13 g), urea (2.4 g), concentrated HCl (10 ml), water (4 ml) and ethanol (150 ml) was refluxed for 4 hours. After cooling to room temperature concentrated ammonium chloride was added until the pH was 7. The resulting yellow solid was filtered off and dried yielding 1.5 g of 5-(4-chlorophenyl)-2-pyrimidinone.

b. 5-(4-chlorophenyl)-1-(2-pentyn-1-yl)-2-pyrimidinone

To a suspension of NaH (60% in mineral oil, 340 mg) in dry DMF (75 ml) at 0° C. was added the preceding pyridinone (1.0 g) and the mixture was stirred at 0° C. for one half hour. To the resulting suspension was added 1-bromo-2-pentyne (750 mg) dropwise. The resulting mixture was kept at 0° C. for one half hour and poured into saturated aqueous ammonium chloride (200 ml). The aqueous suspension was extracted with ether (3×100 ml), the combined ether layers washed with brine and dried, yielding the crude product. Trituration with hexane yielded the product as a yellow solid.

Example 151: 5,5'-[bis(pent-2-yn-1-yl)]-7-chloro-2, 5-dihydroindeno-[1,2-c ]-(2H)-pyridazin-3-one a. 7-chloro-2,5-dihydroindeno-[1,2-c]-(2H)-pyridazin-3-one To a mixture of 2,4,4a,5-tetrahydroindeno-[1,2-c]-pyridazin-3-one (4.5 g, Example 143c) and 100 ml of glacial acetic acid was added with stirring at room temperature, bromine (3.3 g) portionwise and the reaction mixture was refluxed for 3 hours. The reaction mixture was cooled to room temperature and poured in 200 ml of water to yield a white precipitate which was collected by vacuum filtration, washed with water and dried at 40° C. to yield 3.3 g of a tan solid.

b. 5,5'-[bis(pent-2-yn-1-yl)]-7-chloro-2,5-dihydroindeno-[1,2-c]-(2H)-pyridazin-3-one The product for part a was alkylated with 1-bromo-2-pentyne as described in Example 6b to yield a mixture of product and starting material which was purified by column chromatography (silica; 60% ethyl acetate/40% hexane).

Example 152:
6-(4-chlorophenyl)-3-(2-pentyn-1-thio)-pyridazine a. 6-(4-chlorophenyl)-pyridazinthione A mixture of 3.0 g of 6-(4-chlorophenyl)-pyridazinone, 50 ml of dry pyridine and 3.2 g of phosphorus pentasulfide was refluxed for 1 hour, evaporated to dryness and extracted with 200 ml of ether. The ether extract was washed with water (3×100 ml), brine (100 ml), dried over magnesium sulfate and evaporated to yield 3.0 g of 6-(4-chlorophenyl)-pyridazinthione as a yellow solid.

b. 6-(4-chlorophenyl)-3-(2-pentyn-1-thio)-pyridazine

The 6-(4-chlorophenyl)-pyridazinthione from part a was alkylated with 1-bromo-2-pentyne following essentially the procedure described in Example 6b to yield 1.1 g of compound 152 as a white solid.

Example 153: 6-(4-chlorophenyl)-2-(2'-pentynyl)-4,5-dihydropyridazinthione

A mixture of 6-(4-chlorophenyl)-2-(2'-pentynyl)-4,5-dihydropyridazinone (3.0 g, 0.011 mole) 50 ml dry pyridine, and 2.5 g (0.011 moles) of phosphorus pentasulfide was refluxed for one hour, cooled and the pyridine was evaporated in vacuo. The residue was dissolved in 200 ml of ethyl ether and washed with $H_2O$ (3×100) and brine (100 ml). The ether extract was dried over anhydrous $MgSO_4$, stripped to yield 2.6 g (82%) of the product as a yellow solid.

Example 156:
7-chloro-2,4,4a,5-tetrahydro-2-(2-pentyn-4-ene-1-yl)-indeno[1,2-c]-pyridazin-3-one a. 3-vinyl-2-propyn-1-ol To a mixture of potassium hydroxide (1.7 g, 87%, powdered), $FeCl_3$ (0.1 g), dimethyl sulfoxide (100 ml) and ether (100 ml) at 15° C. was added a solution of xylene-free vinyl acetylene (17 g) in 25 ml of ether. The reaction mixture was stirred at 10°–15° C. for 1 hour, then paraformaldehyde (4.5 g) was added in one portion and the mixture was stirred for an additional hour, then quenched with 100 ml of saturated brine and extracted with ether (2×100 ml). The ether extracts were washed with brine (100 ml), dried over magnesium sulfate and evaporated to yield 20 g of the alcohol as a colorless liquid.

b. 7-chloro-2,4,4a,5-tetrahydro-2-(2-pentyn-4-ene-1-yl)-indeno [1,2- c]-pyridazin-3-one The final product was obtained using the alcohol from part a and following essentially the procedures described in Examples 11a and 6b.

Example 157:
6-(4-chlorophenyl)-3-chloro-2-(2'-pentyn-1-yl)-2,5-dihydropyridazine To a solution of 6-(4-chlorophenyl)-2-(2'-pentynyl)pyridazinone (compound 109) (3.0 g, 0.011 mole) in 100 ml dry DMF was cooled to 5° C. and phosphoryl chloride (4.2 g, 0.0275 mole) was added dropwise. The solution immediately turned bright yellow. After stirring for 16 hours the reaction mixture was poured into 200 ml of cold water and stirred to yield a fluffy yellow solid which was filtered off and dried in vacuo at 30° C. to yield 3.0 g (93%) of the product as a yellow solid.

Compound 160 was prepared by the same method starting with phosphorus oxybromide in place of phosphorus oxychloride.

Example 158: 6-(4-chlorophenyl)-3-methoxy-2-(2'-pentyn-1-yl)-2,5-dihydropyridazine A mixture of compound 157 (1.0 g, 0.00342 mole), sodium metal (0.08 g, 0.00342 gram atoms) and 25 ml of anhydrous methanol was stirred at room temperature until all of the sodium metal reacted. The reaction mixture was stirred overnight at room temperature. The methanol was evaporated in vacuo and the residue was taken up in ethyl ether (100 ml). The ether solution was washed with brine (100 ml), dried over anhydrous $MgSO_4$ and stripped to yield 0.45 g of the product as a yellow solid (45% yield).

Compound 159 was prepared analogously using potassium triazole in place of sodium methoxide.

Example 161: 2-(4-chlorophenyl)-4-(2-pentyn-1-yl)-4H,6H-1,3,4-oxadiazin-5-one a. N'-chloroacetyl-4-chlorobenzoic hydrazide To a solution of p-chlorobenzoic hydrazide (11.2 g) in dioxane (100 ml) was added chloroacetyl chloride (6 ml). The resulting mixture was refluxed for three hours, cooled to room temperature and filtered. The resulting solid was washed with ethyl ether and dried to yield N'-chloroacetyl-4-chlorobenzoic hydrazide as white solid.

b. 5,6-dihydro-2-(4-chlorophenyl)-4H-1,3,4oxadiazin-5-one

A mixture of the previous compound (6 g), sodium hydroxide (1.5 g) in DMF (75 ml) was heated at 130° C. for 2 hours with stirring. The cooled reaction mixture was poured into water, and the resulting precipitate was filtered and recrystallized from ethanol/water yielding 5,6-dihydro-2-(4-chlorophenyl)-4H-1,3,4-oxadiazin- 5-one (2.3 g).

c. 2-(4-chlorophenyl)-4-(2-pentyn-1-yl)-4H,6H-1,3,4-oxadiazin-5-one

The previous compound (1.8 g) was added to a mixture of sodium hydride (1.3 g, 60% in mineral oil) and DMF (75 ml) with stirring at 0° C. under nitrogen. The resulting mixture was stirred at 0° C. for 30 minutes and 1-bromo-2-pentyne (1.45 g) was added dropwise with stirring at 0° C. The reaction mixture was stirred at 0° C. for 1 hour, poured into ice-water (150 g), and filtered to yield the product as a yellow solid.

Example 162: 2-(4-chlorophenyl)-3-(2-pentyn-1-yl)-3H,6H-1,3,4-oxadiazin-2-one a. 4-chloro-α-hydroxy-acetophenone Iodobenzene diacetate (67.33 g) was added during 15 minutes to a stirred solution of p-chloroacetophenone (32.2 g) and potassium hydroxide (68.5 g) in methanol (400 ml) which was kept at 0° C., and the mixture was allowed to warm up to room temperature, stirred for 3 hours and then evaporated to dryness under reduced pressure. The residue was shaken with water (300 ml) and ethyl ether (300 ml) and the ether solution was separated, dried over magnesium sulfate and evaporated to dryness. A mixture of the residue, ethanol (70 ml) and aqueous 2N hydrochloric acid (70 ml) was stirred at room temperature overnight and then filtered, and the solid product was recrystallized from methanol to yield 4-chloro-α-hydroxy-acetophenone (17.5 g).

b. 4-chloroacetophenone ethoxycarbonylhydrazone

A mixture of the above compound (16.4 g), ethyl carbazate (10.5 g) and ethanol (400 ml) was stirred at room temperature for five days and then concentrated to small volume by evaporation. The residue was heated until a clear solution was obtained, and then cooled and filtered yielding 4-chloroacetophenone ethoxycarbonylhydrazone as a white solid (16.0 g).

c. 5-(4-chlorophenyl)-3H, 6H-1,3,4-oxadiazin-2-one

Sodium hydride (0.5 g, 60% in mineral oil) was added to a stirred solution of the above compound (11.4 g) in ethanol (250 ml) and the mixture was stirred at room temperature overnight and then filtered. The solid product formed was filtered and dried to yield 5-(4-chlorophenyl)-3H,6H-1,3,4-oxadiazin-2-one as a white solid (8.2 g).

d. sodium salt of 5-(4-chlorophenyl)-3H,6H-1,3,4-oxadiazin-2-one

Sodium hydride (2.0 g, 60% in mineral oil) was added to a stirred solution of the above compound (8.2 g) in tetrahydrofuran (300 ml). The resulting mixture was stirred at room temperature until the gas evolution stopped, the solvent was evaporated under vacuum and the residue was triturated with hexane yielding the sodium salt of 5-(4-chlorophenyl)-3H, 6H-1,3,4-oxadiazin-2-one as a white solid (10.4 g).

e. 2-(4-chlorophenyl)-3-(2-pentyn-1-yl)-3H, 6H-1,3,4-oxadiazin-2-one

The previous compound (2.0 g) was dissolved in DMF (75 ml) with stirring at 0° C. under nitrogen. To the resulting mixture was added 1-bromo-2-pentyne (1.5 g) dropwise with stirring at 0° C. The reaction mixture was stirred at 0° C. during 1 hour, poured into ice-water (150 g), and filtered to yield the product as a yellow solid (2.5 g).

Compounds 163 and 164 were prepared using essentially the same procedure.

Example 165: 5-(4-chlorophenyl)-3-(2-pentyn-1-yl)-3H,6H-1,3,4-thiadiazin-2-one a. 5-(4-chlorophenyl)-3H,6H-1,3,4-thiadiazin-2-one A mixture of 2-bromo-p-chloroacetophenone (9.16 g), methoxythiocarbonylhydrazine (13.0 g) and acetonitrile (75 ml) was refluxed overnight and then cooled and filtered. The light yellow solid was washed with hexane and dried yielding 5-(4-chlorophenyl)-3H,6H-1,3,4-thiadiazin-2-one (4.3 g).

b. salt of 5-(4-chlorophenyl)-3H,6H-1,3,4-thiadiazin-2-one

Sodium hydride (0.5 g, 60% in mineral oil) was added to a stirred solution of the above compound (2.0 g) in THF (100 ml). The resulting mixture was stirred at room temperature until the gas evolution stopped, the solvent was evaporated under vacuum and the residue was triturated with hexane yielding the sodium salt of 5-(4-chlorophenyl)-3H,6H- 1,3,4-thiadiazin-2-one.

c. 5-(4-chlorophenyl)-3-(2-pentyn-1-yl)-3H,6H-1,3,4-thiadiazin-2-one

The previous compound was dissolved in DMF (75 ml) with stirring at 0° C. under nitrogen. To the resulting mixture was added 1-bromo-2-pentyne (1.5 g) dropwise with stirring at 0° C. The reaction mixture was stirred at 0° C. during 2 hours, poured into ice-water (150 g) and filtered to yield the product as a yellow solid.

Example 200:
4,4a,5,6-tetrahydro-8-chloro[h]-cinnolin-2 -(2'-pentynyl)-3-one a. 4-(3-chlorophenyl)-butyric acid To a 300 ml round-bottomed flask equipped with magnetic stirrer and reflux condenser was charged 23.7 g of 87% potassium hydroxide and 150 ml of diethyleneglycol, With stirring, 23 g of 3-(3-chlorobenzoyl)-propionic acid was added followed by 24 g of 85% hydrazine. The mixture was heated to reflux for 2 hours when 50 ml of solvent was azeotroped off into a Dean-Stark trap. The reaction was refluxed for an additional 2 hours, cooled, and poured into 500 g of ice with 50 ml of con. hydrochloric acid. A white precipitate was formed which was extracted into 400 ml of ethyl ether, and washed with 100 ml of water and 100 ml of saturated sodium chloride solution. The ether extract was dried over anhydrous magnesium sulfate, filtered, and stripped to yield 19.5 g of product as a white solid.

b. 4-(3-chlorophenyl)-butyryl chloride

To a dry 100 ml flask equipped with a magnetic stirrer and reflux condenser was charged the product from part a and 20 ml of thionyl chloride. The solution was refluxed for 2 hours, cooled, and stripped to yield 18 g of product as a yellow oil.

c. 6-chlorotetralone

To a dry 500 ml flask equipped with side-arm addition funnel, thermometer, nitrogen inlet, and magnetic stirrer, was charged 33 g of anhydrous aluminum chloride and 200 ml of dry carbon disulfide. The product from part b (18 g) was added dropwise to the mixture and the reaction was refluxed for 2.5 hours. The reaction was then cooled and poured into 300 g of ice-water and extracted with 3×100 ml of ethyl ether. The ether extract was washed with 100 ml of water and 100 ml of saturated sodium chloride solution, dried over anhydrous magnesium sulfate, filtered, and stripped to yield 7.5 g of product as a yellow liquid.

d. 6-chloro-2-(carboxymethylidene)-tetralone

To a dry 250 ml flask equipped with side-arm addition funnel, thermometer, and magnetic stirrer was charged 6.7 g of sodium metaperiodate in 40 ml of water. The solution was cooled to 5° C. and treated with 0.6 ml of con. sulfuric acid followed by a solution of 4.7 g of D-tartaric acid in 9 ml of water, and 20 ml of absolute ethanol. The mixture was stirred for 16 hours at room temperature, warmed to 80° C. for 10 minutes, cooled, and diluted with 150 ml of water. The basic solution was washed once with 100 ml of ethyl ether, and acidified to pH 4 with 1N hydrochloric acid. The resulting precipitate was collected by vacuum filtration and dried overnight in vacuo at 30° C. to yield 7.2 g of product as a white solid.

e. 6-chloro-2-(carboxylmethylene)-tetralone

To a dry 100 ml flask equipped with magnetic stirrer was charged 7.2 g of the product from part d, 20 ml of water, 50 ml of glacial acetic acid, and 3.8 g of zinc dust. The reaction was warmed to 50° C. for 1 hour and stirred overnight at ambient temperature. The reaction was then poured into 100 ml of ethyl acetate, filtered, and washed with 100 ml of water and 100 ml of saturated sodium chloride solution. The ethyl acetate extract was dried over anhydrous magnesium sulfate, filtered, and stripped to yield 6.0 g of product as a white solid.

f. 4,4a,5,6-tetrahydro-8-chlorobenzo[h]cinnolin-3-(2H)-one

The product from part e was treated with hydrazine using essentially the same procedure described for 12 d to yield 5.7 g of product as a tan solid.

g. 4,4a,5,6-tetrahydro-8-chlorobenzo[h]cinnolin-2-(2'-pentynyl)-3-one

The product was prepared from the product in part f using essentially the same procedure described for example 12 e.

Example 201:
6-(4-chlorophenyl)-2-methyl-4,5-dihydropyridazinone

To a 250 ml flask equipped with magnetic stirrer and reflux condenser was charged 10 g of 3-(4-chlorobenzoyl)-propionic acid, 250 ml of absolute ethanol, and 2.5 ml of methyl hydrazine. The reaction was refluxed for 3 hours and cooled to yield a solid which was collected by vacuum filtration, washed with 50 ml of hexane, and air dried. Isolated 9.5 g of product as a white solid.

Example 202:
5,6-dihydro-8-chlorobenzo[h]cinnolin-3-(2'-pentynyl)-one

The product from 200, part f, was oxidized and alkylated using essentially the same procedures described for example 109 a,b.

Example 203:
6-(4-chlorophenyl)-4-(2'-pentynyl)-2-methyl-4,5-dihydropyridazinone To a dry 250 ml flask equipped with nitrogen inlet, side-arm addition funnel, thermometer, and magnetic stirrer, was charged 3.0 g of compound 201 and 75 ml of anhydrous ethyl ether. The solution was cooled to −78° C. with a dry ice acetone bath and 8.4 ml of 1.6M n-butyl lithium was added dropwise. The reaction was stirred at −78° C. for 0.5 hours and 1.98 g of pentynyl bromide was then added dropwise in 25 ml of ether. The reaction was stirred at −70° C. for 1 hour and overnight at ambient temperature. The reaction was then quenched with 100 ml of water and extracted with 3×100 ml of ethyl ether. The ether extract was washed with 100 ml of water and 100 ml of saturated sodium chloride solution, dried over anhydrous magnesium sulfate, filtered, and stripped to yellow oil which was chromatographed on silica gel with 30% ethyl acetate, hexane. Isolated 0.7 g of product as a white solid.

Example 204: 6-(4-chlorophenyl)-2-(5-methyl-2-furanylmethylene)-pyridazinone a. 2-chloromethyl-5-methylfuran To a dry 200 ml flask equipped with reflux condenser, magnetic stirrer, nitrogen inlet, and side-arm addition funnel was charged 10 g of 2-dimethylaminomethyl-5-methylfuran and 50 ml of hexane. At room temperature, 7.8 g of ethyl chloroformate was added dropwise, and the solution was then refluxed for 2 hours. Vacuum distillation (0.5 mm Hg, 60°–65° C.), afforded 1 g of pure product.

b. 6-(4-chlorophenyl)-2-(5-methyl-2-furanylmethylene)-pyridazinone

The product was prepared from the product in part a using essentially the same procedure described for example 12 e.

Example 205:
6-(4-chlorostyryl)-2-(2'-pentynyl)-4,5-dihydropyridazinone a. 3-(4-chlorocinnamoyl)-propionic acid To a dry 250 ml flask equipped with a magnetic stirrer, Dean-Stark trap, and reflux condenser was charged 15 g of 4-chlorobenzaldehyde, 12.4 g levulenic acid, 5.7 ml of piperidine, and 100 ml of toluene. The reaction was refluxed for 3 hours, after which no water was observed to azeotrope from the solution. The reaction was cooled and stripped to yield a reddish-brown liquid which was triturated with hexane to yield 11.2 g of product as a yellow solid.

b. 6-(4-chlorostyryl)-2-(2'-pentynyl)-4,5-dihydropyridazinone

The product from part a was cyclized with hydrazine and alkylated with pentynyl mesylate using essentially the same procedures described for example 12 d–e.

Example 206: 6-(4-chlorophenethyl)-2-(2'-pentynyl)-4,5-dihydropyridazinone a. 6-(4-chlorophenethyl)-2(H)-4,5-dihydropyridazinone 4.5 g of 6-(4-chlorostyryl)-2(H)-4,5-dihydropyridazinone was dissolved in 200 ml of methoxyethanol and charged to a 500 ml Parr® hydrogenation bottle. 1 g of 10% palladium on carbon was added as a slurry in methoxyethanol and the reaction was treated with hydrogen on a Parr® apparatus at 50 psi and ambient temperature. When the theoretical amount of hydrogen was consumed (35 min.) the hydrogenation was stopped and the catalyst was filtered off. The organic solvent was stripped off and the residue was chromatographed on silica gel with 50% ethyl acetate, hexane to yield 3.2 g of the product as a yellow solid.

b. 6-(4-chlorophenethyl)-2-(2'-pentynyl)-4,5-dihydropyridazinone

The product from part a was alkylated with pentynyl mesylate using essentially the same procedure described for example 12 d.

Example 207: 6-(3,4-methylenedioxyphenyl)-2-(2'-pentynyl)-4,5-dihydropyridazinone The product was prepared from piperonylic acid using essentially the same procedures described for example 12 b–e.

Example 208: 6-(4-chlorophenyl)-2-(1-methyl-2-pentynyl)-4,5-dihydropyridazinone a. 3-hexyn-2-yl-methyl sulfonate The mesylate of 3-hexyn-2-ol was prepared using essentially the same procedure described for example 11 a.

b. 6-(4-chlorophenyl)-2-(1-methyl-2-pentynyl)-4,5-dihydropyridazinone 6-(4-chlorophenyl)-4,5-dihydropyridazinone was alkylated with the product from part a using essentially the same procedure described for example 6 b.

Example 209: 6-(2-fluorophenyl)-2-(2'-pentynyl)-4,5-dihydropyridazinone

The product was prepared from 2-fluorobenzoyl chloride using essentially the same procedures described for example 12 b–e.

Example 210: 6-(2-methylphenyl)-2-(2'-pentynyl)-4,5-dihydropyridazinone

The product was prepared from 2-methylbenzoyl chloride using essentially the same procedures described for example 12 b–e.

Example 211: 6-(2-chlorophenyl)-2-(2'-pentynyl)-4,5-dihydropyridazinone

The product was prepared from 2-chlorobenzoyl chloride using essentially the same procedures described for example 12 b–e.

Example 212: 6-(2-methoxyphenyl)-2-(2'-pentynyl)-4,5-dihydropyridazinone

The product was prepared from 2-methoxybenzoyl chloride using essentially the same procedures described for example 12 b–e.

Example 213: 6-(3-trifluoromethylphenyl)-2-(2'-pentynyl)-4,5-dihydropyridazinone The product was prepared from 3-trifluoromethylbenzoyl chloride using essentially the same procedures described for example 12 b–e.

Example 214: 6-(3-fluorophenyl)-2-(2'-pentynyl)-4,5-dihydropyridazinone

The product was prepared from 3-fluorobenzoyl chloride using essentially the same procedures described for example 12 b–e.

Example 215: 6-(3-methylphenyl)-2-(2'-pentynyl)-4,5-dihydropyridazinone

The product was prepared from 3-methylbenzoyl chloride using essentially the same procedures described for example 12 b–e.

Example 216: 6-(3-chlorophenyl)-2-(2'-pentynyl)-4,5-dihydropyridazinone

The product was prepared from 3-chlorobenzoyl chloride using essentially the same procedures described for example 12 b–e.

Example 217: 6-(3-cyanophenyl)-2-(2'-pentynyl)-4,5-dihydropyridazinone

The product was prepared from 3-cyanobenzoyl chloride using essentially the same procedures described for example 12 b–e.

Example 218: 6-(3-nitrophenyl)-2-(2'-pentynyl)-4,5-dihydropyridazinone

The product was prepared from 3-nitrobenzoyl chloride using essentially the same procedures described for example 12 b–e.

Example 219: 6-(3-methoxyphenyl)-2-(2'-pentynyl)-4,5-dihydropyridazinone

The product was prepared from 3-methoxybenzoyl chloride using essentially the same procedures described for example 12 b–e.

Example 220:
6-(3-methoxy-4-methylphenyl)-2-(2'-pentynyl)-4,5-dihydropyridazinone The product was prepared from 3-methoxy-4-methyl benzoic acid using essentially the same procedures described for example 12 b–e.

Example 221:
6-(3-chloro-4-methoxyphenyl)-2-(2'-pentynyl)-4,5-dihydropyridazinone The product was prepared from 3-chloro-4-methoxy benzoic acid using essentially the same procedures described for example 12 b–e.

Example 222:
6-(3-bromo-4-fluorophenyl)-2-(2'-pentynyl)-4,5-dihydropyridazinone The product was prepared from 3-bromo-4-fluorobenzoic acid using essentially the same procedures described for example 12 b–e.

Example 223:
6-(3-nitro-4-methoxyphenyl)-2-(2'-pentynyl)-4,5-dihydropyridazinone The product was prepared from 3-nitro-4-methoxy benzoic acid using essentially the same procedures described for example 12 b–e.

Example 224: 6-(3,4-difluorophenyl)-2-(2'-pentynyl)-4,5-dihydropyridazinone

The product was prepared from 3,4 difluoro benzoic acid using essentially the same procedures described for example 12 b–e.

Example 225:
6-(3-fluoro-4-methylphenyl)-2-(2'-pentynyl)-4,5-dihydropyridazinone The product was prepared from 3-fluoro-4-methyl benzoic acid using essentially the same procedures described for example 12 b–e.

Example 226:
6-(3-nitro-4-methoxyphenyl)-2-(2'-pentynyl)-4,5-dihydropyridazinone a. 3-nitro-4-methoxy benzoic acid To a 500 ml erlenmeyer flask with magnetic stirrer was charged 10.3 g of 3-nitro-4-methoxy-methylbenzoate, 400 ml tetrahydrofuran, and 3.2 g of 86% potassium hydroxide. The reaction was stirred for 12 hours at ambient temperature, after which the resulting solid was collected by vacuum filtration and washed with 2×100 ml of ethyl ether. The solid was dissolved in 200 ml of water and acidified to pH 4 with 6N hydrochloric acid. The resulting precipitate was collected by vacuum filtration, washed with 200 ml water, and dried overnight in vacuo at 30° C. Isolated 7.4 g of product as a white solid.

b. 6-(3-nitro-4-methoxyphenyl)-2-(2'-pentynyl)-4,5-dihydropyridazinone

The product from part a was converted to the product using essentially the same procedures described for example 12 b–e.

Example 227: 6-(9,10-dihydro-2-phenanthrene)-2-(2'-pentynyl)-4,5-dihydropyridazinone The product was prepared from 9,10-dihydro-omega-oxo-2-phenanthrene butyric acid using essentially the same procedures described for example 6 a–b.

Example 228:
5,6-diphenyl-4-cyano-2-(2'-pentynyl)-pyridazinone

The product was prepared from 2,3-dihydro-3-oxo-5,6-diphenyl-4-pyridazine carbonitrile using essentially the same procedure described for example 12 e.

Example 229: 6-(2-quinoline)-2-(2'-pentynyl)-4,5-dihydropyridazinone

The product was prepared from 2-quinoline carboxylic acid using essentially the same procedure described for example 12 b–e.

Example 230: 6-(2-quinoxaline)-2-(2'-pentynyl)-4,5-dihydropyridazinone

The product was prepared from 2-quinoxaloyl chloride using essentially the same procedure described for example 12 b–e.

Example 231:
6-(4-chlorophenyl)-2-(3,5-dimethyl-4-isoxolylmethyl)-4,5-dihydropyridazinone The product was prepared from 4-(chloromethyl)-3,5-dimethylisoxozole using essentially the same procedure described for example 6 b.

Example 232:
8-(2'-pentynyl)-acenaphtho[1,2c]pyridazin-9-one a. methyl(Z)-(1,2-dihydro-2-oxo-1-acenaphthyleneylidene)-acetate To a 500 ml flask equipped with magnetic stirrer, thermometer, nitrogen inlet, and side-arm addition funnel was charged 8.4 g methyl-(triphenylphosphoranylidene)-acetate and 200 ml of absolute ethanol. A precipitate formed immediately. The reaction was stirred at ambient temperature for 2 hours, and the precipitate was then collected by vacuum filtration. Isolated 4.4 g of product as a yellow solid.

b. 8-(H)-acenaphtho[1,2c]pyridazin-9-one

To a 200 ml flask equipped with magnetic stirrer and reflux condenser was charged 2.5 g of the product from part a and 100 ml of chloroform. At room temperature, 0.45 ml of 85% hydrazine was added and the reaction was refluxed for a total of 2 hours. Upon cooling, a precipitate was formed which was collected by vacuum filtration. Isolated 0.5 g of the product as a yellow solid.

c. 8-(2'-pentynyl)-acenaphtho[1,2c]pyridazin-9-one

The product from part b was alkylated with pentynyl mesylate using essentially the same conditions described for example 12 e.

Example 233: 6-(4-chlorophenyl)-2-(acetyl hydrazide)-4,5-dihydropyridazinone a. 6-(4-chlorophenyl)-2-(ethylacetyl)-4,5-dihydropyridazinone To a dry 100 ml flask equipped with magnetic stirrer and reflux condenser was charged 10 g of (4-chlorobenzoyl)-propionic acid, 50 ml absolute ethanol, and 5.3 g triethyl amine. With stirring, 7.3 g of ethyl hydrazinoacetate hydrochloride was added portionwise and the reaction was refluxed for 3 hours. Upon cooling, a white crystalline solid formed which was collected by vacuum filtration, and washed with 100 ml hexane. Isolated 13.3 g of product as a white solid.

b. 6-(4-chlorophenyl)-2-(acetyl hydrazide)-4,5-dihydropyridazinone

To a 100 ml flask equipped with magnetic stirrer and reflux condenser was charged the product from part a (10.2 g), 10 ml water, and 6.1 ml of 85% hydrazine. The reaction was heated to 70° C. for 6 hours, cooled, and diluted with 200 ml of cold water. The resulting solid was collected by vacuum filtration and dried overnight in vacuo at 40° C. to yield 9.6 g of product as a white solid.

Example 234:
6-(4-chlorophenyl)-2-[N-acetylhydrazide-(N'-2,4-pentanedione-hydrazone)]-4,5-dihydropyridazinone To a dry 100 ml flask equipped with magnetic stirrer and reflux condenser was charged 1 g of compound 233, 30 ml of absolute ethanol, and 0.4 ml of 2,4-pentanedione. After refluxing for 1 hour, the solvent was stripped off and the residue was triturated with hexane to yield 0.7 g of product as a pale yellow solid.

Example 235:
6-(3-thianaphthene)-2-(2'-pentynyl)-4,5-dihydropyridazinone a. 3-thianaphtheneoyl acrylic acid To a 250 ml flask equipped with Dean-Stark trap, reflux condenser, and magnetic stirrer, was charged 5 g of 3-acetyl thianaphthene, 100 ml of toluene, and 3.9 g of glyoxylic acid hydrate. The reaction was refluxed and azeotroped for 2.5 hours after which the toluene was removed by vacuum distillation. The resulting residue was washed with hexane to yield a solid which was collected by vacuum filtration to yield 6 g of product as a yellow solid.

b. 6-(3-thianaphthene)-2[H]-4,5-dihydropyridazinone

The product from part a was charged to a 100 ml flask equipped with magnetic stirrer and reflux condenser. 60 ml of glacial acetic acid and 20 ml of water was added followed by 2.5 g of zinc dust. The reaction was heated to 50° C. for 2 hours, cooled, and poured into 150 ml of ethyl acetate. The insoluble material was filtered off and the ethyl acetate extract was washed with 100 ml of water, 100 ml of saturated sodium chloride solution, dried over anhydrous magnesium sulfate, filtered and stripped. The residue was redissolved in 50 ml of absolute ethanol and treated with 0.75 ml of 85% hydrazine. After refluxing for 3 hours, the reaction was cooled to yield a solid which was collected by vacuum filtration. Isolated 3.7 g of product as a yellow solid.

c. 6-(3-thianaphthene)-2-(2'-pentynyl)-4,5-dihydropyridazinone

The product from part b was alkylated with pentynyl mesylate with essentially the same procedure described for example 12 c.

Example 236:
6-(3-thianaphthene)-2-(2'-pentynyl)-pyridazinone

The product was isolated from the silica gel column chromatography (30% ethyl acetate,hexane) of the crude product from compound 235.

Example 237:
6-(4-chlorophenyl)-2-(3,5-dimethyl-1-pyrazoylmethylene)-4,5-dihydropyridazinone The product was prepared from compound 233 using essentially the same procedure used to prepare compound 234 with 0.5 ml of 6N hydrochloric acid as a catalyst. Isolated 0.9 g of product as a white solid.

Example 238:
6-(4-chlorophenyl)-2-(1,3,4-oxadiazin-2-one-5-yl-methylene)-4,5-dihydropyridazinone To a 100 ml flask equipped with magnetic stirrer, side-arm addition funnel, thermometer, and nitrogen inlet was charged 1.5 g of compound 233 and 30 ml of methylene chloride. At room temperature, a solution of 0.54 g triphosgene in 30 ml of methylene chloride was added dropwise. The reaction was refluxed for 1 hour, cooled, and stripped to yield a white solid which was slurried in hexane and collected by vacuum filtration. Isolated 1.55 g of product as a white solid.

Example 239:
6-(4-chlorophenyl)-2-[1,3,4-oxadiazin-2-one-3-(2'-pentynyl)-5-yl-methylene]-4,5-dihydropyridazinone To a dry 100 ml flask equipped with magnetic stirrer, side-arm addition funnel, thermometer, and reflux condenser was charged 0.5 g compound 238, 0.45 g potassium carbonate, and 50 ml of dry acetone. The reaction was stirred for 1 hour at room temperature and 0.3 g of pentynyl mesylate was added dropwise in 5 ml of acetone. The reaction was refluxed for 1 hour, cooled, and filtered. The filtrate was stripped. to yield a yellow solid which was dissolved in 100 ml of ethyl acetate and washed with 100 ml of water and 100 ml of saturated sodium chloride solution. The ethyl acetate extract was the dried over anhydrous magnesium sulfate, filtered, and stripped to yield 0.6 g of product as a white solid.

Example 240: 6-(4-chlorophenyl)-2-[N-acetylhydrazide-(N'-3,5-dichloro-2-hydroxy-phenylhydrazone)]-4,5-dihydropyridazinone To a dry 100 ml erlenmeyer flask was charged 0.65 g compound 233, 25 ml ethanol, and 0.45 g of 3,5-dichloro salicylaldehyde. To the stirring solution was the added 5 drops of glacial acetic acid. The reaction was stirred for 2 hours at room temperature, after which the resulting precipitate was collected by filtration and washed with 50 ml of hexane. Isolated 0.9 g of product as a yellow solid.

Example 241:
6-(4-chlorophenyl)-2-[1,3,4-oxadiazin-2-one-3-(3'-iodopropargyl)-5-yl-methylene]-4,5-dihydropyridazinone a. 6-(4-chlorophenyl)-2-[1,3,4-oxadiazin-2-one-3-(propargyl)- 5-yl-methylene-4,5-dihydropyridazinone Compound 238 was alkylated with propargyl bromide using essentially the same procedure used to prepare compound 239.

b. 6-(4-chlorophenyl)-2-[1,3,4-oxadiazin-2-one-3-(3'-iodopropargyl)- 5-yl-methylene]-4,5-dihydropyridazinone To a dry 100 ml flask equipped with magnetic stirrer and reflux condenser was charged 0.5 g of the product from part a, 0.4 g of N-iodosuccinimide, 10 mg of silver nitrate, and 40 ml of dry acetone. The reaction was stirred for 16 hours at ambient temperature, poured into 100 ml of acetone, and filtered to remove solids. The acetone flitrate was stripped and the residue was redissolved in 150 ml of ethyl acetate. The ethyl acetate extract was washed with 100 ml of water, 100 ml of saturated sodium chloride solution, dried over anhydrous magnesium sulfate, filtered, and stripped to yield 0.5 g of the product as a yellow viscous liquid.

The compounds of the present invention have fungitoxic activity, particularly against phytopathogenic fungi. They are active against fungi of a number of classes including Deuteromycetes (Fungi Imperfecti), Basidiomycetes and Ascomycetes. More particularly, the method of this invention provides for activity against organisms including *Pyricularia oryzae, Pyrenophora trichostoma, Fusarium species, Erysiphe graminis, Puccinia recondita, alsa leucostoma, Colletotrichum lagenarium, Nectria galligena, Cochliobolus miyabeanus, Thanatephorus cucumeris, Pseudocercosperella herpotrichioides, Helminthosporium species, Monilinia fructicola, Sclerotium rolfsii, Venturia inequalis, Botryotinia fuckeliana, Diaporthe citri, Rhizopus stolonifer, Verticillium albo-atrum, Phytophthora capsici, Alternaria solani, Ustilago maydis, Pythium ultimum, Leptosphaeria nodorum, Schlerotinia species, Sphaerotheca fuliginea, Gymnosporangium asiaticum, Alternaria alternata, Uncinula necator,* and *Podosphaera leucotricha.* More particularly, rice diseases are controlled by the method of the invention. Examples of such rice diseases are seedborne diseases such as those incited by *Cochliobolus miyabeanus* and *Pyricularia oryzae,* soilborne diseases such as *Fusarium species, Rhizoctonia species,* and *Rhizopus species,* and seedling box and field diseases such as those incited by *Pyricularia oryzae, Thanatephorus cucumeris* and *Cochliobolus miyabeanus.* Additional diseases include powdery mildew incited by *Sphaerotheca fulignea* (e.g., cucurbit powdery mildew), *Uncinula necator* (e.g., grape powdery mildew), and *Podosphaera leucotricha* (e.g., apple powdery mildew).

The compounds of the invention also control wood decay fungi such as *Gleophyllum trabeum, Phialophora mutabilis, Poria palcenta* and *Trametes versicolor.* Accordingly, the present invention also encompasses the use of the compounds as wood preservatives.

The compounds of the invention can be applied as fungicidal sprays by methods commonly employed, such as conventional high-gallonage hydraulic sprays, low-gallonage sprays, air-blast, aerial sprays and dusts. Such use conveniently permits treatment of fungal infestations in crops such as vegatables, fruits, ornamentals, seeds, turf, cereal and vines among other plants. The dilution and rate of application will depend upon the type of equipment employed, the method and frequency of application desired and diseases to be controlled, but the effective amount is usually from about 0.01 kilogram (kg) to about 20 kg, of active ingredient (a.i.) per hectare. As a foliar fungicide, the pyridazinone is usually applied to growing plants at a rate of about 0.1 to about 5 and preferably from about 0.125 to about 0.5 kg per hectare.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare.

The compounds of the present invention are useful for the control of fungi and can be utilized at various loci such as the seed, the water surface, the soil or the foliage. For such purposes, these compounds can be used in the technical or pure form as prepared, as solutions or as formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and when desired suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in *McCutcheon's Emulsifiers and Detergents, McCutcheon's Emulsifiers and Detergents/Functional Materials* and *McCutcheon's Functional Materials* all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds of the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates; this can be as high as 75%.

Wettable powders suitable for spraying can be prepared by admixing the compound with finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of 6-(4-chlorophenyl)-2-(2'-pentynyl)-4,5-dihydropyridazinone, 45 parts of a synthetic precipitated hydrated silicon dioxide sold under the trademark Hi-Sil® and 5 parts of sodium lignosulfonate (Marasperse® N-22). In another preparation of a Kaolin type, (Barden) clay is used in place of the Hi-Sil in the above-wettable powder and in another such preparation 25% of the Hi-Sil is replaced with a synthetic sodium silicoaluminate sold under the trademark Zeolex® 7.

Dusts are prepared by mixing the compounds of the invention with finely divided inert solids which can be organic or inorganic in nature. Materials useful for this purpose include botanical flours, silicas, silicates, carbonates and clays. One convenient method for preparing a dust is to dilute a wettable powder with a finely divided carrier. Dust concentrates containing 20% to 80% of the active ingredient are commonly made and are subsequently diluted to 1% to 10% use concentration.

The compounds of the present invention may be utilized in combination with other fungicides such as:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2ochlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol,flutriafol, fiusilazole, propiconazole, ectaconazole, myclobutanil, fenbuconazole {i.e., alpha-[2-(4-chlorophenyl)ethyl]-alpha-phenyl-1H- 1,2,4-triazole-1-propanenitrile}, hexaconazole, cyproconazole, terbuconazole, diniconazole, fiuoroimide, pyridine-2-thiol-1-oxide, 8-hydroxyquinoline sulfate and metal salts thereof, 2,3-dihydro-5-carboxanilido- 6-methyl-1,4-oxathiin-4,4-dioxide, 2,3-dihydro-5-carboxanilido-6-methyl-1,4-oxathiin, cis-N-[(1,1,2,2-tetra-chloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N- (2'-methoxyacetyl) alanine methyl ester, D,L-methyl-N-(2,6-dimethylphenyl)-N-chloroacetyl-D,L-2 aminobutyrolactone, D,L-N-(2,6-dimethylphenyl)-N-(phenylacetyl) alanine methyl ester, 5-methyl-5-vinyl-3-(3, 5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chlorothalonil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) miscellaneous fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edifenphos, isoprothiolane, probenazole, iprobenfos, tricyclazole, and pyroquilon.

It is particularly advantageous to utilize the present invention in combination with a dithiocarbamate, e.g., mancozeb or maneb, for added control of non-phycomycetes fungi.

The compounds of examples 1–165 and 200–241 were tested for their fungicidal activity. The compounds were tested in vivo and/or in vitro against the following organisms: *Pyricularia oryzae, Pyrenophora trichostoma, Fusarium species, Erysiphe graminis, Puccinia recondita, Valsa leucostoma, Colletotrichum lagenarium, Nectria galligena, Cochliobolus toiyabeanus, Thanatephorus cucumeris, Pseudocercosperella herpotrichioides, Helminthosporium species, Monilinia fructicola, Sclerotium rolfsii, Venturia inequalis, Botryotinia fuckeliana, Diaporthe citri, Rhizopus stolonifer, Verticitlium albo-atrum, Phytophthora capsici, Alternaria solani, Ustilago maydis, Pythium ultimum, Leptosphaeria nodorum, Schlerotinia species, Sphaerotheca fuliginea, Gyrnnosporangium asiaticum, Alternaria alternata, Uncinula necator,* and *Podosphaera leucotricha,* according to the following methods:

I. In Vitro Tests—Fungitoxicity Assay

Compounds were assayed for activity by the broth-dilution (BD) method or the agar-dilution (AD) method. In the agar-dilution method, potato dextrose agar was amended with a solution of the test compounds, solubilized in dimethyl sulfoxide or similar solvent at the concentration indicated in Table VI, then inoculated with a 6 mm plug of fungal mycelium. The radial growth was measured for each sample, and corrected for inoculum size. The percent growth inhibition is equal to the radial growth of the control sample (A) minus the radial growth of the treated sample (B) divided by the radial growth of the control sample (A) times 100 as seen by the following equation.

$$\text{Percent Growth Inhibition} = \frac{A-B}{A} \times 100 \text{ Inhibition}$$

In the broth-dilution method, test compounds dissolved in dimethyl sulfoxide were added at the concentration indicated in Table VI to YD broth (2% dextrose, 0.4% yeast extract) and incubated with fungal inoculum for 48 hours at 28° C. in an environmental shaker, at 200 rpm. Growth inhibition was determined by dry weight measurement according to the following formula:

$$\text{Percent growth Inhibition} = \frac{\text{Dry weight Control(mg)} - \text{Dry weight Treated (mg)}}{\text{Dry weight Control (mg)}} \times 100$$

The results of the in vitro tests are reported in Table VI.

TABLE VI

| Cmpd No. | ppm | % growth inhibition | test* | Cmpd No. | ppm | % growth inhibition | test* |
|---|---|---|---|---|---|---|---|
| 1. | 5 | 92.7 | BD | 33. | 100 | 27.6 | BD |
| 2. | 100 | 0 | BD | 34. | 10 | 100.0 | BD |
| 3. | 100 | 53.6 | BD | 35. | 50 | 85.0 | BD |
| 4. | 100 | 26.7 | BD | 36. | 50 | 100.0 | BD |
| 5. | 100 | 75.0 | BD | 37. | 100 | 100.0 | BD |
| 6. | 100 | 91.5 | BD | 38. | 100 | 75.2 | BD |
| 7. | 100 | 94.4 | BD | 39. | 50 | 94.6 | BD |
| 8. | 100 | 96.2 | BD | 40. | 5 | 95.7 | BD |
| 9. | 100 | 94.4 | BD | 41. | 10 | 89.2 | BD |
| 10. | 100 | 100.0 | BD | 42. | 10 | 91.7 | BD |
| 11. | 10 | 87.7 | BD | 43. | 10 | 22.3 | BD |
| 12. | 1 | 96.0 | BD | 44. | 5 | 87.0 | BD |
| 13. | 10 | 87.0 | BD | 45. | 10 | 100.0 | BD |
| 14. | 50 | 100.0 | BD | 46. | 100 | 100.0 | BD |
| 15. | 50 | 37.1 | BD | 47. | 50 | 100.0 | BD |
| 16. | 50 | 12.7 | BD | 48. | 50 | 100.0 | BD |
| 17. | 25 | 91.9 | BD | 49. | 50 | 100.0 | BD |
| 18. | 5 | 88.4 | BD | 50. | 50 | 100.0 | BD |

TABLE VI-continued

IN VITRO BIOLOGICAL DATA

| Cmpd No. | ppm | % growth inhibition | test* | Cmpd No. | ppm | % growth inhibition | test* |
|---|---|---|---|---|---|---|---|
| 19. | 100 | 96.8 | BD | 51. | 50 | 100.0 | BD |
| 20. | 10 | 100.0 | BD | 52. | 50 | 93.7 | BD |
| 21. | 100 | 45.8 | BD | 53. | 50 | 100.0 | BD |
| 22. | 100 | 99.7 | BD | 54. | 200 | 71.4 | AD |
| 23. | 5 | 100.0 | BD | 55. | 50 | 100.0 | BD |
| 24. | 200 | 6.1 | AD | 56. | 1 | 100.0 | BD |
| 25. | 50 | 100.0 | BD | 57. | 100 | 95.7 | BD |
| 26. | 50 | 96.3 | BD | 58. | 10 | 39.8 | BD |
| 27. | 50 | 100.0 | BD | 59. | 10 | 100.0 | BD |
| 28. | 1 | 100.0 | BD | 60. | 10 | 100.0 | BD |
| 29. | 1 | 86.1 | BD | 61. | 10 | 95.3 | BD |
| 30. | 50 | 41.2 | BD | 62. | 1 | 100.0 | BD |
| 31. | 5 | 92.4 | BD | 63. | 200 | 100.0 | AD |
| 32. | 100 | 100.0 | BD | 64. | 25 | 100.0 | AD |
| 65. | 50 | 84.0 | AD | 103. | 1 | 100.0 | AD |
| 66. | 25 | 100.0 | AD | 104. | 5 | 100.0 | AD |
| 67. | 5 | 83.6 | BD | 105. | 10 | 33.3 | AD |
| 68. | 5 | 10.4 | BD | 106. | 50 | 81.0 | AD |
| 69. | 50 | 100.0 | BD | 107. | 200 | 83.7 | AD |
| 70. | 5 | 100.0 | BD | 108. | 5 | 100.0 | BD |
| 71. | 50 | 92.6 | BD | 109. | 1 | 100.0 | AD |
| 72. | 0.5 | 96.2 | BD | 110. | 10 | 100.0 | BD |
| 73. | 50 | 94.4 | BD | 111. | 25 | 100.0 | BD |
| 74. | 1 | 100.0 | AD | 112. | 10 | 100.0 | BD |
| 75. | 100 | 100.0 | AD | 113. | 10 | 64.3 | BD |
| 76. | 10 | 100.0 | AD | 114. | 5 | 100.0 | BD |
| 77. | 10 | 89.2 | BD | 115. | 50 | 93.7 | BD |
| 78. | 0.5 | 100.0 | BD | 116. | 50 | 82.5 | BD |
| 79. | 50 | 17.0 | AD | 117. | 200 | 34.7 | BD |
| 80. | 2.5 | 100.0 | AD | 118. | 200 | 100.0 | AD |
| 81. | 2.5 | 95.8 | AD | 119. | 5 | 99.3 | BD |
| 82. | 2.5 | 100.0 | AD | 120. | 1 | 100.0 | AD |
| 83. | 0.5 | 81.3 | AD | 121. | 1 | 100.0 | AD |
| 84. | 50 | 75.8 | BD | 122. | 100 | 84.6 | AD |
| 85. | 100 | 100.0 | AD | 123. | 100 | 100.0 | AD |
| 86. | 100 | 80.0 | AD | 124. | 10 | 100.0 | BD |
| 87. | 100 | 100.0 | AD | 125. | 0.5 | 89.5 | AD |
| 88. | 100 | 80.0 | AD | 126. | 10 | 100.0 | AD |
| 89. | 10 | 100.0 | AD | 127. | 1 | 100.0 | AD |
| 90. | 1 | 100.0 | AD | 128. | 0.156 | 100.0 | AD |
| 91. | 1 | 100.0 | AD | 129. | 1 | 100.0 | AD |
| 92. | 1 | 100.0 | BD | 130. | 1 | 100.0 | AD |
| 93. | 0.5 | 100.0 | AD | 131. | 1 | 100.0 | AD |
| 94. | 10 | 22.2 | AD | 132. | 200 | 91.8 | AD |
| 95. | 10 | 22.2 | AD | 133. | 200 | 67.4 | AD |
| 96. | 10 | 94.5 | AD | 134. | 50 | 66.5 | BD |
| 97. | 1 | 100.0 | AD | 135. | 94.4 | 94.4 | BD |
| 98. | 10 | 40.0 | AD | 136. | 1 | 84.6 | BD |
| 99. | 1 | 100.0 | AD | 137. | 200 | 18.4 | AD |
| 100. | 0.16 | 100.0 | AD | 138. | 100 | 64.6 | BD |
| 101. | 1 | 100.0 | AD | 139. | 100 | 65.0 | BD |
| 102. | 1 | 100.0 | AD | 140. | 100 | 37.8 | BD |
| 141. | 100 | 23.9 | BD | 154. | 10 | 16.0 | AD |
| 142. | 50 | 100.0 | BD | 155. | 10 | 92.0 | AD |
| 143. | 1 | 100.0 | AD | 156. | 1 | 100.0 | AD |
| 144. | 1 | 100.0 | AD | 157. | 10 | 100.0 | AD |
| 145. | 1 | 96.0 | BD | 158. | 10 | 100.0 | AD |
| 146. | 10 | 5.0 | BD | 159. | 1 | 100.0 | AD |
| 147. | 50 | 98.1 | BD | 160. | 1 | 100.0 | AD |
| 148. | 10 | 0 | BD | 161. | 1 | 75.9 | AD |
| 149. | 50 | 51.5 | BD | 162. | 10 | 96.9 | AD |
| 150. | 50 | 48.2 | BD | 163. | 10 | 12.7 | AD |
| 151. | 100 | 80.6 | BD | 164. | 100 | 14.2 | AD |
| 152. | 10 | 18.2 | AD | 165. | 100 | 100.0 | AD |
| 153. | 10 | 90.9 | AD | | | | |
| 200. | 10 | 100 | AD | 224. | 50 | 100 | AD |
| 201. | 10 | 10 | AD | 225. | 50 | 100 | AD |
| 202. | 10 | 100 | AD | 226. | 50 | 100 | AD |
| 203. | 10 | 100 | AD | 227. | 10 | 30 | AD |
| 204. | 10 | 100 | AD | 228. | 10 | 50 | AD |
| 205. | 10 | 100 | AD | 229. | 5 | 100 | AD |
| 206. | 1 | 14.3 | AD | 230. | 10 | 30 | AD |
| 207. | 1 | 100 | AD | 231. | 10 | 36 | AD |
| 208. | 1 | 28.6 | AD | 232. | 5 | 45.5 | AD |
| 209. | 50 | 85.7 | AD | 233. | 100 | 21 | AD |
| 210. | 50 | 35 | AD | 234. | 100 | 42 | AD |
| 211. | 50 | 30 | AD | 235. | 100 | 100 | AD |
| 212. | 50 | 35 | AD | 236. | 100 | 100 | AD |
| 213. | 50 | 100 | AD | 237. | 100 | 58 | AD |
| 214. | 50 | 100 | AD | 238. | 100 | 31.6 | AD |
| 215. | 50 | 100 | AD | 239. | 100 | 100 | AD |
| 216. | 50 | 100 | AD | 240. | 100 | 14 | AD |
| 217. | 50 | 100 | AD | 241. | 100 | 100 | AD |
| 218. | 50 | 100 | AD | | | | |
| 219. | 50 | 100 | AD | | | | |
| 220. | 50 | 100 | AD | | | | |

*AD = agar dilution, BD = broth dilution

II InVivo Tests

Compounds were tested at 200 ppm as a twenty-four hour preapplication protectant test prior to inoculation.

a) Rice Blast (RB) *Pyricularia Oryzae*

Two week old M201 rice plants were inoculated with 250,000 spores per pot of *Magnaporthe grisea* (*Pyricularia oryzae*) by spraying the leaves and stems with an atomizer. The inoculated plants were incubated in a mist cabinet at 80° F. for 48 hours, then placed in a greenhouse environment (70°–80° F.). Six days after inoculation the plants were evaluated for percent disease control compared to check plants with the aid of standard area disease diagrams.

b) Rice Sheath Blight (RSB)

*Thanatephorus cucumeris* (*Rhizoctonia solani*) mycelia were grown for six days in potato dextrose broth in shake culture. Drained mycelial mats were blended with an approximately equal weight of rice flour and five parts water. This slurry was dispensed onto the soil surface of pots containing rice seedlings previously treated with experimental compounds. The plants were placed in a mist chamber at 25°–28° C. for 48 hours. Following two more days at 25° C. and 70–90% relative humidity the plants were evaluated for percent disease control compared to check plants.

The results of the in vivo tests are reported in Table VII.

TABLE VII

IN VIVO BIOLOGICAL RESULTS at 200 ppm

| Cmpd No. | % Control RB | % Control RSB | Cmpd No. | % Control RB | % Control RSB | Cmpd No. | % Control RB | % Control RSB |
|---|---|---|---|---|---|---|---|---|
| 1. | 90 | 0 | 34. | 90 | — | 71. | 0 | — |
| 2. | 0 | 0 | 35. | 75 | — | 72. | 90 | — |
| 3. | 0 | 0 | 36. | 90 | — | 73. | 95 | — |
| 4. | 0 | 0 | 37. | 90 | — | 74. | 75 | — |
| 5. | 0 | 50 | 38. | 75 | — | 75. | 0 | — |
| 6. | 0 | 0 | 39. | 0 | — | 76. | 0 | — |
| 7. | 0 | 0 | 40. | 0 | — | 77. | 0 | — |
| 8. | 0 | 0 | 41. | 0 | — | 78. | 0 | — |
| 9. | 0 | 0 | 43. | 0 | — | 79. | 100 | 75 |
| 10. | —[a] | 80 | 45. | 0 | — | 80. | 99 | 0 |
| 11. | 0 | 0 | 46. | 0 | — | 81. | 95 | — |
| 12. | 99 | 50 | 47. | 0 | — | 82. | 0 | — |
| 13. | 50 | 50 | 48. | 90 | — | 83. | 90 | — |
| 14. | 0 | — | 49. | 90 | — | 84. | 95 | 0 |
| 15. | 0 | 50 | 50. | 0 | — | 85. | 0 | — |
| 16. | 0 | 50 | 51. | 100 | — | 86. | 0 | — |
| 17. | 0 | 80 | 52. | 0 | — | 87. | 75 | — |
| 18. | 0 | 0 | 53. | 100 | — | 88. | 0 | — |
| 19. | 50 | 0 | 54. | 0 | — | 89. | 95 | 0 |

TABLE VII-continued

IN VIVO BIOLOGICAL RESULTS
at 200 ppm

| Cmpd No. | % Control RB | % Control RSB | Cmpd No. | % Control RB | % Control RSB | Cmpd No. | % Control RB | % Control RSB |
|---|---|---|---|---|---|---|---|---|
| 20. | 0 | 0 | 55. | 0 | — | 90. | 0 | 95 |
| 21. | 0 | 0 | 56. | 100 | — | 91. | 90 | — |
| 22. | 75 | — | 57. | 0 | — | 92. | 90 | — |
| 23. | 50 | — | 58. | 0 | — | 93. | 0 | — |
| 24. | 0 | — | 59. | 0 | — | 94. | 0 | — |
| 25. | 50 | — | 60. | 50 | — | 95. | 0 | — |
| 26. | 95 | — | 61. | 90 | — | 96. | 0 | — |
| 27. | 0 | — | 62. | 99 | — | 99. | 0 | — |
| 28. | 95 | — | 63. | 0 | — | 100. | 100 | 0 |
| 29. | 95 | — | 64. | 0 | — | 101. | 75 | 0 |
| 31. | 90 | — | 65. | 0 | — | 102. | 99 | 0 |
| 32. | 0 | — | 66. | 0 | — | 103. | 95 | 0 |
| 33. | 0 | — | 70. | 0 | — | 104. | 0 | 0 |
| 105. | 75 | 0 | 123. | 99 | — | 145. | 95 | 0[a] |
| 106. | 0 | — | 124. | 0 | — | 146. | 0 | — |
| 107. | 0 | 0 | 125. | 0 | — | 148. | 0 | — |
| 108. | 95 | 50 | 127. | 0 | — | 149. | 100 | — |
| 109. | 99 | 100 | 128. | 95 | 0 | 150. | 99 | 95 |
| 110. | 0 | — | 129. | 0 | 0 | 151. | 0 | — |
| 111. | 0 | — | 132. | 0 | 0 | 152. | 0 | — |
| 112. | 90 | — | 133. | 0 | — | 153. | 0 | — |
| 113. | 95 | — | 134. | 0 | — | 154. | 50 | 0 |
| 114. | 50 | — | 135. | 0 | — | 155. | 100 | 90 |
| 115. | 50 | — | 136. | 99 | — | 156. | 100 | 95 |
| 116. | 0 | — | 137. | 0 | — | 157. | 10 | 0 |
| 117. | 0 | — | 138. | 0 | — | 158. | 0 | — |
| 118. | 0 | — | 139. | 0 | — | 159. | 0 | 0 |
| 119. | 95[a] | 0[a] | 140. | 75 | — | 160. | 0 | 95 |
| 120. | 99 | — | 141. | 0 | — | 161. | 99 | 0 |
| 121. | 95 | — | 142. | 50 | — | | | |
| 122. | 0 | — | 143. | 99 | — | | | |

"—" means not tested
*Tested at 100 ppm

The compounds of the invention are also active against *Candida albicans*. Accordingly, the compounds of this invention can be used to control *Candida albicans* and dermatophytes, such as *Trichophyton species*, for example in humans by application in a known pharmaceutically acceptable carrier by means known to one skilled in the art.

The activity against *Candida albicans* was determined using the following test protocol.

1. Inoculum preparation

Conidia and mycelium from the *Candida albicans* culture maintained on potato dextrose agar plates were lightly scraped off into yeast extract-dextrose broth (YDB) so that mostly conidia was used as inoculum. The conidial suspension was strained through a double layer of cheesecloth to remove mycelial clumps. The inoculum mixture was placed in microtiter plates using a 12-tipped pipet. 175 microliters were placed in each well of the microtiter plates and the plates were placed in the refrigerator overnight. There were two replications.

2. Addition of the compounds

The compounds to be tested were dissolved in 1:1 acetone:methanol and 100 ppm of the compound solution were placed in a well of the prepared microtiter plates.

3. Incubation and rating

The microtiter plates were incubated for 7 days at room temperature after addition of the compounds. Percent control was visually estimated using a microtiter plate reading mirror. Readings were made at 1, 2, 3, and/or 7 days after treatment.

The results are listed in Table VIII.

TABLE VIII

| Cmpd | ppm | % CONTROL OF GROWTH +1 | +2 | +3 | +7 |
|---|---|---|---|---|---|
| 12 | 100 | 100 | 100 | 100 | 100 |
| 109 | 100 | 100 | 100 | 100 | 100 |
| 119 | 100 | 100 | 100 | 100 | 100 |
| 56 | 100 | 100 | 100 | 100 | |
| 120 | 100 | 100 | 100 | 100 | |
| 76 | 100 | 100 | 100 | 100 | |
| 34 | 100 | 100 | 100 | 100 | |
| 161 | 100 | 100 | 100 | 100 | |
| 121 | 100 | 100 | 100 | 100 | |
| 127 | 100 | 100 | 100 | 100 | |
| 153 | 100 | 100 | 100 | 100 | |
| 156 | 100 | 100 | 100 | 100 | |
| 100 | 100 | 100 | 100 | 100 | |
| 128 | 100 | 100 | 100 | 100 | |
| 130 | 100 | 100 | 100 | 100 | |
| 131 | 100 | 100 | 100 | 100 | |
| 229 | 100 | 100 | 100 | 100 | |

It has been found unexpectedly that compositions comprising certain compounds of the present invention in admixture with certain known fungicidal compounds have an enhanced fungicidal activity which is greater than the expected additive sum of the activities of the individual components of the composition. The expected activity, E, for a given combination of active fungicidal components can be calculated in accordance with the Colby formula:

$$E = X + Y - (X*Y/100),$$

wherein

X=disease control action (in percent) of a first fungicide,
Y=disease control action (in percent) of a second fungicide, and
E=expected action of the first and second fungicide in admixture. [ See Colby, L. R., "Calculating synergistic and antagonistic responses of herbicide combinations", *Weeds*, 15. pp. 20–22 (1967) and Limpel et al., "Weeds control by certain combinations", Proc. NEWCL, 16, pp. 48–53 (1962).]

The ratio of the fungicidal components of the composition having this enhanced property can vary over a range of ratios dependent upon the particular components and conditions of use. In general, such a composition will comprise at least a sufficient amount of each component in an effective ratio to produce compositional fungicidal activity greater than the expected additive sum of the activities of the individual components of the composition. Preferably, the observed, actual fungicidal activity is at least about one-half percent (0.5%) greater than, more preferably at least about five percent (5%) greater than the expected additive sum of the activities of the individual components of the composition. When properly measured, there is an observed E value greater than, preferably significantly greater than, the expected Colby formula-calculated E value, i.e.—(Actual E/Expected E) greater than 1; preferably (Actual E/Expected E) greater than 1.005; and more preferably (Actual E/Expected E) greater than 1.05.

The present invention also embodies a composition having enhanced fungicidal properties and comprising
(i) one or more compounds having the formula 6-(3-A-4-B-phenyl)-2-(C)-pyridazinone, wherein A represents a hydrogen or fluoro substituent; B represents a hydrogen, chloro, or bromo substituent; and C represents a 2'-pentynyl, a 3'-vinyl-2'-propynyl, a 4'-fluoro-2'-pentynyl or a 5'-fluoro-2'-pentynyl substituent; or 6-(3-A'-4-B'-phenyl)-2(C')-4,5- dihydropyridazinone, wherein A' represents a hydrogen or fluoro substituent; B' represents a hydrogen, bromo, or chloro substituent; and C' represents a 2'-pentynyl, a 3'-vinyl-2'-propynyl, a 4'-fluoro-2'-pentynyl or a 5'-fluoro-2'-pentynyl substituent; and (ii) one or more fungicidal compounds selected from mancozeb, maneb, iprodione, chlorothalonil, probenazole, pyroquilon and fenbuconazole.

A preferred composition having enhanced fungicidal properties includes one or more compositions having the formula 6-(3-A-4-B-phenyl)-2-(C)-pyridazinone is 6-(3-A-4-chlorophenyl)-2-(C)-pyridazinone wherein A is either a fluoro or hydrogen substituent and C is either a 2'-pentynyl or a 3'-vinyl-2'-propynyl substituent. More preferred is 6-(4-chlorophenyl)-2-(2'-pentynyl)-pyridazinone, 6-(3-fluoro-4-chlorophenyl)-2-(2'-pentynyl)-pyridazinone, 6-(4-chlorophenyl)-2-(3'-vinyl-2'-propynyl)-pyridazinone, or 6-(3-fluoro-4-chlorophenyl)-2-(3'-vinyl-2'-propynyl)-pyridazinone.

A preferred compound having enhanced fungicidal properties includes one or more compositions having the formula 6-(3-A'-4-B'-phenyl)-2-(C')-4,5-dihydropyridazinone is 6-(3-A'-4-chlorophenyl)-2-(C')-4,5-dihydropyridazinone wherein A' is either a fluoro or hydrogen substituent and C' is either a 2'-pentynyl or a 3'-vinyl-2'-propynyl substituent. More preferred is 6-(4-chlorophenyl)-2-( 2'-pentynyl)-4,5-dihydropyridazinone, 6-(3-fluoro-4-chlorophenyl)-2-(2'-pentynyl)-4,5-dihydropyridazinone, 6-(4-chlorophenyl)-2-(3'-vinyl-2'-propynyl)-4,5-dihydropyridazinone, or 6-(3-fluoro-4-chlorophenyl)-2-(3'-vinyl-2'-propynyl)-4,5-dihydropyridazinone.

Preferred combinations having enhanced properties include (i) 6-(4-chlorophenyl)-2-(2'-pentynyl)-pyridazinone, (ii) 6-(3-fluoro-4-chlorophenyl)-2-(2'-pentynyl)-pyridazinone, or (iii) 6-(4-chlorophenyl)-2-(2'-pentynyl)-4,5-dihydropyridazinone, in combination with mancozeb, probenazole, pyroquilon, iprodione, fenbuconazole, or chlorothalonil.

More preferred combinations are 6-(4-chlorophenyl)-2-(2'-pentynyl)-pyridazinone in combination with mancozeb, probenazole, pyroquilon, iprodione, or fenbuconazole; and 6-(4-chlorophenyl)-2-(2'-pentynyl)-4,5-dihydropyridazinone in combination with chlorothalonil.

Preferably, in such combinations having enhanced properties, the ratio of either pyradizinone or the dihydro pyradizinone compound to the other fungicide compound can range from about 25/1 to about 1/25. Illustrative preferred approximate ratios are as follows:

(i) When Component I is 6-(4-chlorophenyl)-2-(2'-pentynyl) pyridazinone in combination with

| Component II | preferred ratio of I/II (by ppm) | more preferred ratio of I/II |
|---|---|---|
| (1) mancozeb | 20/1 to 1/20 | 4/1 to 1/4 |
| (2) probenazole | 20/1 to 1/20 | 16/1 to 1/16 |
| (3) pyroquilon | 25/1 to 1/25 | 16/1 to 1/16 |
| (4) iprodione | 10/1 to 1/10 | 4/1 to 1/4 |
| (5) fenbuconazole | 10/1 to 1/10 | 4/1 to 1/4 |

(ii) When component I is 6-(4-chlorophenyl)-2-(2'-pentynyl)-4,5-dihydropyridazinone in combination with chlorothalonil, a preferred ratio is 20/1 to 1/20, more preferably a ratio of 4/1 to 1/4.

The methods of use of the compositions of the present invention having enhanced activity include those methods described above for the fungicides when used alone. Benefits can be obtained from the use of these compositions having enhanced activity since lesser amounts of the fungicides can be utilized for particular applications as compared to the use of the individual compound alone or greater spectrum and length of activity at the same or lesser concentrations than those combinations of fungicides which do not have enhanced activities.

The following experiments are illustrative of the compositions having enhanced activity and activities of the present invention described above, but are not intended to be limitations on the scope of these combinations:

EXPERIMENTAL PROCEDURES

The experiments below were performed using the relevant following procedures.

Experimental compounds and commercial fungicides were tank mixed and mechanically sprayed at varying concentrations in a 1:1:2 mixture of acetone, methanol and water. Protective or preventive sprays were applied one day before spore inoculation. Curative or post-infection sprays were applied one day after spore inoculation. The spraying system utilized delivered a 200 ppm dose at the rate of 1458 liters per hectare. The following details were applicable for the specified diseases:

Rice Blast Pyricularia Experiments

M-201 rice plants were inoculated with *Pyricularia oryzae* conidia. The spore concentration was 300,000 to 500,000 conidia per milliliter in water. An atomizer was used to apply twenty milliliters of inoculum to twenty plants per flat. The plants were placed in a humidity cabinet at 100% relative humidity for 48 hours and then placed in a greenhouse. Evaluations were made 7–8 days after inoculation.

Wheat Septoria Experiments

Fielder wheat plants were inoculated with *Septoria nodorum* conidia. The spore concentration was approximately 3,000,000 conidia per milliliter in water. An atomizer was used to apply twenty milliliters of inoculum to twenty plants per flat. The plants were placed in a humidity cabinet at 100% relative humidity for 72 hours and then placed in a greenhouse. Evaluations were made 10 days after inoculation.

Tomato Botrytis Experiments

Three week-old "Pixie" tomato plants were inoculated with *Boytrytis cinerea* conidia. The plants were held in dim light for two days prior to inoculation. The spore concentration was 500,000 to 650,000 conidia per milliliter of dextrose solution. An atomizer was used to apply the conidial suspension in a heavy coating to near runoff to both the upper and lower leaf surfaces and to the plant stem. The plants were kept in a continuous mist chamber with a day-night cycle and at 20 degrees centigrade for 5 days.

"Disease control" was recorded as percent control based on a comparison of the unsprayed, inoculated controls and the treated, inoculated plants. The rates of application are indicated in the Tables.

TABLE IX

Rice Blast Protectant Using 6-(4-chlorophenyl)-2-(2'-pentynyl)-pyridazinone (component "A") and mancozeb (component "B")

| Rate ppm | | % Disease Control | |
|---|---|---|---|
| A | B | Calculated | Observed |
| 0 | 0 | — | 0 |
| 200 | — | — | 99 |
| 50 | — | — | 0 |

TABLE IX-continued

Rice Blast Protectant Using 6-(4-chlorophenyl)-2-(2'-pentynyl)-pyridazinone (component "A") and mancozeb (component "B")

| Rate ppm | | % Disease Control | |
|---|---|---|---|
| A | B | Calculated | Observed |
| 12 | — | — | 0 |
| — | 200 | — | 99 |
| — | 50 | — | 75 |
| 200 | 50 | 99 | 99 |
| 50 | 50 | 75 | 99 |
| 12 | 50 | 75 | 99 |

TABLE X

Rice Blast Curative Using 6-(4-chlorophenyl)-2-(2'-pentynyl)-pyridazinone (component "A") and mancozeb (component "B")

| Rate ppm | | % Disease Control | |
|---|---|---|---|
| A | B | Calculated | Observed |
| 0 | 0 | — | 0 |
| 200 | — | — | 80 |
| 50 | — | — | 50 |
| 12 | — | — | 0 |
| — | 200 | — | 0 |
| — | 50 | — | 0 |
| — | 200 | 80 | 90 |
| 50 | 200 | 50 | 80 |
| 12 | 200 | 0 | 50 |

TABLE XI

Rice Blast Protectant Using 6-(4-chlorophenyl)-2-(2'-pentynyl)-4,5-dihydropyridazinone (component "A") and chlorothalonil (component "B")

| Rate ppm | | % Disease Control | |
|---|---|---|---|
| A | B | Calculated | Observed |
| 0 | 0 | — | 0 |
| 200 | — | — | 50 |
| 50 | — | — | 50 |
| 12 | — | — | 0 |
| — | 200 | — | 99 |
| — | 50 | — | 0 |
| — | 12 | — | 0 |
| 200 | 50 | 50 | 90 |
| 50 | 50 | 50 | 75 |
| 12 | 50 | 0 | 75 |

TABLE XII

Rice Blast Protectant Using 6-(4-chlorophenyl)-2-(2'-pentynyl)-pyridazinone (component "A") and probenazole (component "B")

| Rate ppm | | % Disease Control | |
|---|---|---|---|
| A | B | Calculated | Observed |
| 0 | 0 | — | 0 |
| 200 | — | — | 80 |
| 50 | — | — | 0 |
| 12 | — | — | 0 |
| — | 200 | — | 0 |
| — | 50 | — | 0 |
| 200 | 200 | 80 | 90 |
| 50 | 200 | 0 | 80 |
| 12 | 200 | 0 | 50 |

TABLE XIII

Rice Blast Protectant Using 6-(4-chlorophenyl)-2-(2'-pentynyl)-pyridazinone (component "A") and pyroquilon (component "B")

| Rate ppm | | % Disease Control | |
|---|---|---|---|
| A | B | Calculated | Observed |
| 0 | 0 | — | 0 |
| 200 | — | — | 80 |
| 50 | — | — | 0 |
| 12 | — | — | 0 |
| — | 200 | — | 85 |
| — | 50 | — | 0 |
| — | 12 | — | 0 |
| 200 | 200 | 97 | 90 |
| 50 | 200 | 85 | 90 |
| 12 | 200 | 85 | 90 |
| 200 | 50 | 80 | 90 |
| 50 | 50 | 0 | 90 |
| 12 | 50 | 0 | 0 |
| 200 | 12 | 80 | 85 |
| 50 | 12 | 0 | 50 |
| 12 | 12 | 0 | 50 |

TABLE XIV

Wheat Septoria Preventative Using 6-(4-chlorophenyl)-2-(2'-pentynyl)-pyridazinone (component "A") and iprodione (component "B")

| Rate ppm | | % Disease Control | |
|---|---|---|---|
| A | B | Calculated | Observed |
| 0 | 0 | — | 0 |
| 200 | — | — | 50 |
| 50 | — | — | 50 |
| 12 | — | — | 0 |
| — | 200 | — | 50 |
| — | 50 | — | 0 |
| — | 12 | — | 0 |
| 200 | 50 | 50 | 90 |
| 50 | 50 | 50 | 80 |
| 12 | 50 | 0 | 80 |

TABLE XV

Tomato Botrytis Protective Using 6-(4-chlorophenyl)-2-(2'-pentynyl)-pyridazinone (component "A") and fenbuconazole (component "B")

| Rate ppm | | % Disease Control | |
|---|---|---|---|
| A | B | Calculated | Observed |
| 0 | 0 | — | 0 |
| 200 | — | — | 75 |
| 50 | — | — | 0 |
| — | 50 | — | 75 |
| — | 25 | — | 75 |
| — | 6 | — | 50 |
| 200 | 50 | 93 | 90 |
| 50 | 50 | 75 | 90 |
| 12 | 50 | 75 | 90 |

What is claimed is:

1. A method for controlling phytopathogenic fungus which comprises applying to the fungus or its habitat a fungicidally-effective amount of the formula

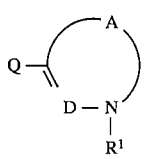

wherein when the compound is a five member ring
A is —CHR⁷—Z—, or S—Z—;
D is nitrogen
Q is an aromatic group selected from

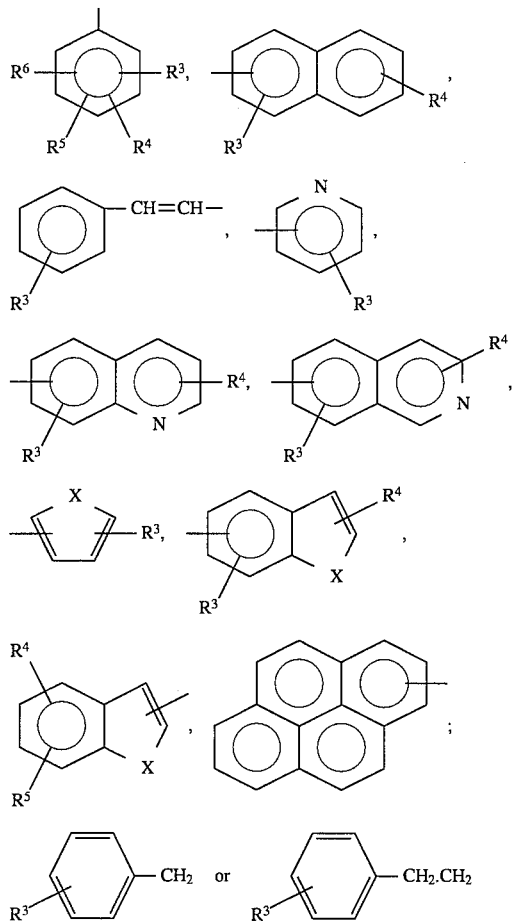

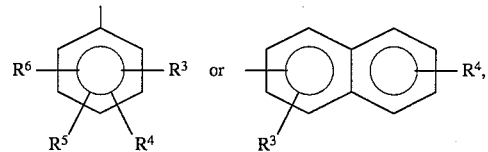

X is oxygen (O) or sulfur (S);

Z is carbonyl (C=O) or thiocarbonyl (C=S);

$R^1$ is alkyl, hydroxyalkyl, cyanoalkyl, hydrazidal, phenylcarbonyl, alkenyl, haloalkenyl, alkynylalkenyl, alkynyl, haloalkynyl, dialkynyl, cydoalkylalkynyl, alkenylalkynyl, hydroxyalkynyl, alkoxyalkynyl, alkanoyloxyalkynyl, formylalkynyl, trialkyisilylalkynyl, trialkyllinalkynyl, haloalkenylalkynyl, carboxyalkynyl, or alkoxycarbonylalkynyl;

$R^3$ and $R^6$ are each independently hydrogen, alkoxy or halo;

$R^4$ is hydrogen, halo, alkoxy or nitro;

$R^5$ is hydrogen, halo, nitro, alkyl alkoxy, alkylthio, haloalkyl, haloalkoxy, haloalkylthio, phenyl, phenoxy or cyano;

$R^7$ is hydrogen, $(C_1-C_3)$alkyl, phenyl, cyano, halo, alkynyl, alkynylalkenyl, dialkynyl, haloalkynyl or alkenylalkynyl;

$R^8$ is hydrogen, $(C_1-C_3)$alkyl, phenyl, cyano or halo;

provided when Q is phenyl, D is nitrogen, A is —CHR⁷—Z— wherein Z is C=O and $R^7$ is hydrogen, $(C_1-C_3)$alkyl or phenyl and $R^1$ is phenylalkyl or heterocyclylalkyl, the alkyl portion of the $R^1$ moiety must be a straight chain; when Q is $R^1$ is alkyl, A is —CHR⁷—Z— and Z is C=O, $R^3$, $R^4$, $R^5$, $R^6$, and $R^7$ cannot all be hydrogen; and when A is S—Z—, $R^1$ cannot be haloalkynyl;

and agronomically acceptable salts thereof.

* * * * *